(12) United States Patent
Hagerty et al.

(10) Patent No.: US 7,482,327 B2
(45) Date of Patent: Jan. 27, 2009

(54) METHODS FOR TREATING IMMUNE DISORDERS ASSOCIATED WITH GRAFT TRANSPLANTATION WITH SOLUBLE CTLA4 MUTANT MOLECULES

(75) Inventors: David Hagerty, Pennington, NJ (US); James Rusnak, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/399,666

(22) Filed: Apr. 6, 2006

(65) Prior Publication Data

US 2007/0009511 A1 Jan. 11, 2007

Related U.S. Application Data

(60) Provisional application No. 60/668,774, filed on Apr. 6, 2005.

(51) Int. Cl.
*A61K 38/16* (2006.01)
(52) U.S. Cl. ...................... 514/12; 424/134.1
(58) Field of Classification Search ................. None
See application file for complete search history.

(56) References Cited

U.S. PATENT DOCUMENTS

| | | | |
|---|---|---|---|
| 4,399,216 A | 8/1983 | Axel et al. | |
| 5,434,131 A | 7/1995 | Linsley et al. | |
| 5,637,481 A | 6/1997 | Ledbetter et al. | |
| 5,773,253 A | 6/1998 | Linsley et al. | |
| 5,844,095 A | 12/1998 | Linsley et al. | |
| 5,851,795 A | 12/1998 | Linsley et al. | |
| 5,885,796 A | 3/1999 | Linsley et al. | |
| 6,051,228 A | 4/2000 | Aruffo et al. | |
| 6,090,914 A | 7/2000 | Linsley et al. | |
| 6,444,792 B1 | 9/2002 | Gray et al. | |
| 6,750,334 B1 | 6/2004 | Gray et al. | |
| 2002/0114814 A1 | 8/2002 | Gray et al. | |
| 2002/0182211 A1 | 12/2002 | Peach et al. | |
| 2003/0007968 A1* | 1/2003 | Larsen et al. ........... | 424/144.1 |
| 2004/0151725 A1 | 8/2004 | Gray et al. | |
| 2005/0019859 A1 | 1/2005 | Schilling et al. | |
| 2005/0084933 A1 | 4/2005 | Schilling et al. | |

FOREIGN PATENT DOCUMENTS

| | | |
|---|---|---|
| WO | WO 97/28267 | 8/1997 |
| WO | WO 02/094202 A | 11/2002 |
| WO | WO 03/088991 A | 10/2003 |
| WO | WO 2004/058944 | 7/2004 |
| WO | WO 2006/030220 | 3/2006 |

OTHER PUBLICATIONS

Vincenti, F et al. "Costimulation Blockade with Belatacept in Renal Transplantation", The New England J. of Medicine, vol. 353(8), pp. 770-781 (2005).
Abrams, J.R., et al., "CTLA4Ig-mediated blockade of T-cell costimulation in patients with *Psoriasis vulgaris*", The Journal of Clinical Investigation, vol. 103(9), pp. 1243-1252 (1999).
Adams, A.B., et al., "Calcineurin Inhibitor-Free CD28 Blockade-Based Protocol Protects Allogeneic Islets in Nonhuman Primates", Diabetes, vol. 51, pp. 265-270 (2002).
Adams, A.B., et al., "Development of a Chimeric Anti-CD40 Monoclonal Antibody that Synergizes with LEA29Y to Prolong Islet Allograft Survival[1]", The Journal of Immunology, vol. 174, pp. 542-550 (2005).
Bennett, MD. William M., "Posttransplant Acute Renal Failure", Renal Failure, vol. 19(2), pp. 225-226 (1997).
Broach, James R., "Construction of High Copy Yeast Vectors Using 2-μm Circle Sequences", Methods in Enzymology, vol. 101, pp. 307-325 (1983).
Byrn, R.A. et al., "Characterization of In Vitro Inhibition of Human Immunodeficiency virus by Purified Recombinant CD4", Journal of Virology, vol. 63(10), pp. 4370-4375 (1989).
Clarke, L. et al., "Selection Procedure for Isolation of Centromere DNAs from *Saccharomcyes cerevisiae*", Methods in Enzymology, vol. 101, pp. 300-307 (1983).
Cockroft, D. et al., "Prediction of Creatinine Clearance from Serum Creatinine[1]", Nephron, vol. 16, pp. 31-41 (1976).
Cohen, S. et al., "Nonchromosomal Antibiotic Resistance in Bacteria: Genetic Transformation of *Escherichia coli* by R-Factor DNA*", Proc. Nat. Acad. Sci., vol. 69(8), pp. 2110-2114 (1972).
Danovitch, G.M., "Immunosuppressive medications for renal transplantation: A multiple choice question", Kidney International, vol. 59, pp. 388-402 (2001).
Dash, B. et al., "Deletion of a single *N*-linked glycosylation site from the transmembrane envelope protein of human immunodeficiency virus type 1 stops cleavage and transport of gp160 preventing *env*-mediated fusion", J. of General Virology, vol. 75, pp. 1389-1397 (1994).
Falk, K. et al., "Both human and mouse cells expressing H-2K$^b$ and Ovalbumin Process the same Peptide, SIINFEKL", Cellular Immunology, vol. 150, pp. 447-452 (1993).
Fiers, W. et al., "Complete nucleotide sequence of SV40 DNA", Nature, vol. 273, pp. 113-120 (1978).
Fujikawa, K. et al., "Nuclear localization and transforming activity of Human Papillomavirus Type 16 E7-β-Galactosidse Fusion Protein: Characterization of the Nuclear Localization Sequence", Virology, vol. 204, pp. 789-793 (1994).
Gerard, C. et al., "Production and Characterization of Polyclonal Antibodies recognizing the Intracytoplasmic Third Loop of the 5-Hydroxytryptamine Receptor", Neuroscience, vol. 62(3), pp. 721-739 (1994).
Goeddel, D. et al., "Synthesis of human fibroblast interferon by *E. coli*", Nucleic Acids Research, vol. 8(18), pp. 4057-4074 (1980).
Greene, J. et al., "Covalent Dimerization of CD28/CTLA-4 and Oligomerization of CD80/CD86 Regulate T Cell Costimulatory Interactions8", The Journal of Biological Chemistry, vol. 271(43), pp. 26762-26771 (1996).

(Continued)

*Primary Examiner*—Ilia Ouspenski
(74) *Attorney, Agent, or Firm*—Nickki L. Parlet

(57) ABSTRACT

The present invention provides use of soluble CTLA4 mutant molecules which bind with greater avidity to the CD80 and/or CD86 antigen than wild type CTLA4 or non-mutated CTLA4Ig in the treatment of immune disorders associated with graft transplantation.

25 Claims, 13 Drawing Sheets

OTHER PUBLICATIONS

Hariharan, S. et al., "Post-transplant renal function in the first year predicts long-term kidney transplant survival", Kidney International, vol. 62, pp. 311-318 (2002).

Hartley, R.D., et al.,, "Toxic Metabolites of *Aspergillus Flavus*", Nature, vol. 198, pp. 1056-1058 (1963).

Hess, B. et al., "Cooperation of Glycolytic Enzymes", Adv. Enzyme Reg., vol. 7, pp. 149-167 (1968).

Hitzeman, R. et al., "Isolation and Characterization of the Yeast 3-Phosphoglycerokinase Gene (*PGK*) by an Immunological Screening Technique*", The Journal of Biological Chemistry, vol. 255(2), pp. 12073-12080 (1980).

Holland, M. et al., "Isolation and Identification of Yeast Messenger Ribonucleic Acids Coding for Enolase, Glyceraldehyde-3-phosphate Dehydrogenase, and Phosphoglycerate Kinase", Biochemistry, vol. 17(23) 1978.

Ikeda, T. et al., "Isolation of a cDNA encoding the chicken p50B/p97 (Lyt-10) transcription factor", Gene, vol. 138, pp. 193-196 (1994).

Jelliffe,R.W. "Creatinine Clearance: Bedside Estimate", Annals of Internal Medicine, vol. 79(4), pp. 604 (1973).

Johnsson, B. et al., "Immobilization of Proteins to a Carboxymethyldextran-Modified Gold Surface for Biospecific Interaction Analysis in surface Plasmon Resonance Sensors", Analytical Biochemistry, vol. 198, pp. 268-277 (1991).

Jones, N. et al., "Isolation of complementary DNA clones encoding the human lymphocyte glycoprotein T1/Leu-1", Nature, vol. 323, pp. 346-349 (1986).

Karin, M. et al., "Human metallothionein genes-primary structure of the metallothioein-II gene and a related processed gene", Nature, vol. 299, pp. 797-802 (1982).

Khilko, S. et al., "Direct Detection of Major Histocompatibility Complex Class I Binding to Antigenic Peptides using Surface Plasmon Resonance", The J. of Biological Chemistry, vol. 268(21), pp. 15425-15434 (1993).

Kolhekar, A. et al., "Peptidylglycine α-Hydroxylating Monooxygenase: Active Site Residues, Disulfide Linkages, and a Two-Domain Model of the Catalytic Core", Biochemistry, vol. 36, pp. 10901-10909 (1997).

Kremer, J. et al., "Treatment of Rheumatoid Arthritis by Selective Inhibition of T-Cell Activation with Fusion Protein CTLA4Ig", The New England Journal of Medicine, vol. 349(20), pp. 1907-1915 (2003).

Larsen, C. et al., "Rational Development of LEA29Y (belatacept), a High-Affinity Variant of CTLA4-Ig with Potent Immunosuppresive Properties", American Journal of Transplantation, vol. 5, pp. 443-453 (2005).

Lasky, L. et al., "Neutralization of the AIDS Retrovirus by Antibodies to a Recombinant envelope Glycoprotein", Science, vol. 233, pp. 209-212 (1986).

Lenschow, D. et al., "CD28/B7 System of T Cell Costimulation", Annu. Rev. Immunol., vol. 14, pp. 233-258 (1996).

Levey, A. et al., "A More Accurate Method to estimate Glomerular Filtration Rate from Serum Creatinine: A New Prediction Equation", Annals of Internal Medicine, vol. 130(6), pp. 461-470 (1999).

Linsley, P. et al., "Coexpression and Functional Cooperation of CTLA-4 and CD28 on activated T Lymphocytes", J. Exp. Med., vol. 176, pp. 1595-1604 (1992).

Linsley, P. et al., "Binding Stoichiometry of the Cytotoxic T Lymphocyte-associated Molecule-4 (CTLA-4)", The Journal of Biological Chemistry, vol. 270(25), pp. 15417-15424 (1995).

Linsley, P. et al., "Human B7-1 (CD80) and B7-2 (CD86) Bind with similar Avidities but Distinct Kinetics to CD28 and CTLA-4 Receptors", Immunity, vol. 1, pp. 793-801 (1994).

Linsley, P. et al., "The Role of the CD28 Receptor During T Cell Responses to Antigen", Annu. Rev. Immunol., vol. 11, pp. 191-212 (1993).

Malik. N. et al., "Molecular Cloning, Sequence Analysis, and Functional Expression of a Novel Growth Regulator, Oncostatin M", Molecular and Cellular Biology, vol. 9(7), pp. 2847-2853 (1989).

Martin, P. et al., "Preincubation of Donor Done Marrow Cells with a Combination of Murine Monoclonal Anti-T-Cell Antibodies without Complement does not prevent Graft-Versus-Host Disease after Allogeneic Marrow Transplantation", Journal of Clinical Immunology, vol. 4(1), pp. 18-22 (1984).

Metzler, W. et al., "Solution structure of human CTLA-4 and delineation of a CD80/CD86 binding site conserved in CD28", Nature Structural Biology, vol. 4(7), pp. 527-531 (1997).

Nankivell, B. et al., "Predicting Glomerular Filtration rate after Kidney Transplantation", Transplantation, vol. 59(12), pp. 1683-1689 (1995).

Oosterwegel, M. et al., "CTLA-4 and T cell activation", Current Opinion in Immunology, vol. 11, pp. 294-300 (1999).

O'Shannessy, D. et al., "Determination of Rate and Equilibrium Binding constants for Macromelecular Interactions using surface plasmon resonance: Use of Nonlinear least squares analysis methods", Analytical Biochemistry, vol. 212, pp. 457-468 (1993).

Paul, Leendert C., "Chronic allograft nephropathy-a model of impaired repair from injury?", Nephrol Dial Transplant, vol. 15, pp. 149-151 (2000).

Peach, R. et al., "Complementarity determining Region 1 (CDR1)- and CDR3-analogous Regions in CTLA-4 and CD28 determine the binding to B7-1", J. Exp. med., vol. 180, pp. 2049-2058 (1994).

Racusen, L. et al., "The Banff 97 working classification of renal allograft pathology", Kidney International, vol. 55, pp. 713-723 (1999).

Sambrook, J. et al. "Molecular Cloning: A Laboratory Manual", Cold Spring Harbor Laboratory Press, Second Edition (1989).

Sayegh, M. et al., "The Role of T-Cell Costimulatory Activation Pathways in Transplant Rejection", The New England Journal of Medicine, vol. 338(25), pp. 1813-1821 (1998).

Shimatake, H. et al., "Purified λ regulatory protein cII positively activates promoters for lysogenic development", Nature, vol. 292, pp. 128-132 (1981).

Smith, d. et al., "Blocking of HIV-1 Infectivity by a Soluble, Secreted form of the CD4 Antigen", Science, vol. 238, pp. 1704-1707 (1987).

Stinchcomb, D.T. et al., "Isolation and characterization of a yeast chromosomal replicator", Nature, vol. 282, pp. 39-43 (1979).

Toyama, R. et al., "Human chorionic gonadotropin α and human cytomegalovirus promoters are extremely active in the fission yeast *Schizosaccharomyces pombe*", FEBS, vol. 268(1), pp. 217-221 (1990).

Tschumper, G. et al., "Sequence of a yeast DNA fragment containing a chromosomal replicator and the *TRP1* gene", Gene, vol. 10, pp. 157-166 (1980).

Urlaub, G. et al., "Effect of Gamma Rays at the Dihydrofolate Reductase Locus: Deletions and Inversions", Somatic Cell and Molecular Genetics, vol. 12(6), pp. 555-566 (1986).

Wiecek, A. et al., "Acute failure of the transplanted kidney-athophysiology, diagnosis and prevention", Annals of Transplantation, vol. 1(4), pp. 5-9 (1996).

\* cited by examiner

FIG. 7

```
ATGGGTGTACTGCTCACACAGAGGACGCTGCTCAGTCTGGTCCTTGCACTCCTGTTTCCA      -19
M--G--V--L--L--T--Q--R--T--L--L--S--L--V--L--A--L--L--P--P--      -7

AGCATGGCGAGCATGGCAATGCACGTGGCCCAGCCTGCTGTGGTACTGGCCAGCAGCCGA      +42
S--M--A--S--M--A--M--H--V--A--Q--P--A--V--V--L--A--S--S--R--     +14
                    +1

GGCATCGCTAGCTTTGTGTGTGAGTATGCATCTCCAGGCAAATATACTGAGGTCCGGGTG     +102
G--I--A--S--F--V--C--E--Y--A--S--P--G--K--Y--T--E--V--R--V--     +34

ACAGTGCTTCGGCAGGCTGACAGCCAGGTGACTGAAGTCTGTGCGGCAACCTACATGATG     +162
T--V--L--R--Q--A--D--S--Q--V--T--E--V--C--A--A--T--Y--M--M--     +54

GGGAATGAGTTGACCTTCCTAGATGATTCCATCTGCACGGGCACCTCCAGTGGAAATCAA     +222
G--N--E--L--T--F--L--D--D--S--I--C--T--G--T--S--S--G--N--Q--     +74

GTGAACCTCACTATCCAAGGACTGAGGGCCATGGACACGGGACTCTACATCTGCAAGGTG     +282
V--N--L--T--I--Q--G--L--R--A--M--D--T--G--L--Y--I--C--K--V--     +94

GAGCTCATGTACCCACCGCCATACTACGAGGGCATAGGCAACGGAACCCAGATTTATGTA     +342
E--L--M--Y--P--P--P--Y--Y--E--G--I--G--N--G--T--Q--I--Y--V--    +114

ATTGATCCAGAACCGTGCCCAGATTCTGATCAGGAGCCCAAATCTTCTGACAAAACTCAC     +402
I--D--P--E--P--C--P--D--S--D--Q--E--P--K--S--S--D--K--T--H--    +134

ACATCCCCACCGTCCCCAGCACCTGAACTCCTGGGGGATCGTCAGTCTTCCTCTTCCCC     +462
T--S--P--P--S--P--A--P--E--L--L--G--G--S--S--V--F--L--F--P--    +154

CCAAAACCCAAGGACACCCTCATGATCTCCCGGACCCCTGAGGTCACATGCGTGGTGGTG     +522
P--K--P--K--D--T--L--M--I--S--R--T--P--E--V--T--C--V--V--V--    +174

GACGTGAGCCACGAAGACCCTGAGGTCAAGTTCAACTGGTACGTGGACGGCGTGGAGGTG     +582
D--V--S--H--E--D--P--E--V--K--F--N--W--Y--V--D--G--V--E--V--    +194

CATAATGCCAAGACAAAGCCGCGGGAGGAGCAGTACAACAGCACGTACCGTGTGGTCAGC     +642
H--N--A--K--T--K--P--R--E--E--Q--Y--N--S--T--Y--R--V--V--S--    +214

GTCCTCACCGTCCTGCACCAGGACTGGCTGAATGGCAAGGAGTACAAGTGCAAGGTCTCC     +702
V--L--T--V--L--H--Q--D--W--L--N--G--K--E--Y--K--C--K--V--S--    +234

AACAAAGCCCTCCCAGCCCCCATCGAGAAAACCATCTCCAAAGCCAAAGGGCAGCCCCGA     +762
N--K--A--L--P--A--P--I--E--K--T--I--S--K--A--K--G--Q--P--R--    +254

GAACCACAGGTGTACACCCTGCCCCCATCCCGGGATGAGCTGACCAAGAACCAGGTCAGC     +822
E--P--Q--V--Y--T--L--P--P--S--R--D--E--L--T--K--N--Q--V--S--    +274

CTGACCTGCCTGGTCAAAGGCTTCTATCCCAGCGACATCGCCGTGGAGTGGGAGAGCAAT     +882
L--T--C--L--V--K--G--F--Y--P--S--D--I--A--V--E--W--E--S--N--    +294

GGGCAGCCGGAGAACAACTACAAGACCACGCCTCCCGTGCTGGACTCCGACGGCTCCTTC     +942
G--Q--P--E--N--N--Y--K--T--T--P--P--V--L--D--S--D--G--S--F--    +314

TTCCTCTACAGCAAGCTCACCGTGGACAAGAGCAGGTGGCAGCAGGGGAACGTCTTCTCA    +1002
F--L--Y--S--K--L--T--V--D--K--S--R--W--Q--Q--G--N--V--F--S--    +334

TGCTCCGTGATGCATGAGGCTCTGCACAACCACTACACGCAGAAGAGCCTCTCCCTGTCT    +1062
C--S--V--M--H--E--A--L--H--N--H--Y--T--Q--K--S--L--S--L--S--    +354

CCGGGTAAATGA
P--G--K--*
```

FIG. 8

```
ATGGGTGTACTGCTCACACAGAGGACGCTGCTCAGTCTGGTCCTTGCACTCCTGTTTCCA      -19
M--G--V--L--L--T--Q--R--T--L--L--S--L--V--L--A--L--L--F--P--      -7

AGCATGGCGAGCATGGCAATGCACGTGGCCCAGCCTGCTGTGGTACTGGCCAGCAGCCGA      +42
S--M--A--S--M--A--M--H--V--A--Q--P--A--V--V--L--A--S--S--R--      +14
          +1

GGCATCGCTAGCTTTGTGTGTGAGTATGCATCTCCAGGCAAAGCCACTGAGGTCCGGGTG     +102
G--I--A--S--F--V--C--E--Y--A--S--P--G--K--A--T--E--V--R--V--      +34

ACAGTGCTTCGGCAGGCTGACAGCCAGGTGACTGAAGTCTGTGCGGCAACCTACATGATG     +162
T--V--L--R--Q--A--D--S--Q--V--T--E--V--C--A--A--T--Y--M--M--      +54

GGGAATGAGTTGACCTTCCTAGATGATTCCATCTGCACGGGCACCTCCAGTGGAAATCAA     +222
G--N--E--L--T--F--L--D--D--S--I--C--T--G--T--S--S--G--N--Q--      +74

GTGAACCTCACTATCCAAGGACTGAGGGCCATGGACACGGGACTCTACATCTGCAAGGTG     +282
V--N--L--T--I--Q--G--L--R--A--M--D--T--G--L--Y--I--C--K--V--      +94

GAGCTCATGTACCCACCGCCATACTACCTGGGCATAGGCAACGGAACCCAGATTTATGTA     +342
E--L--M--Y--P--P--P--Y--Y--L--G--I--G--N--G--T--Q--I--Y--V--     +114

ATTGATCCAGAACCGTGCCCAGATTCTGATCAGGAGCCCAAATCTTCTGACAAAACTCAC     +402
I--D--P--E--P--C--P--D--S--D--Q--E--P--K--S--S--D--K--T--H--     +134

ACATCCCCACCCGTCCCCAGCACCTGAACTCCTGGGTGGATCGTCAGTCTTCCTCTTCCCC    +462
T--S--P--P--S--P--A--P--E--L--L--G--G--S--S--V--F--L--F--P--     +154

CCAAAACCCAAGGACACCCTCATGATCTCCCGGACCCCTGAGGTCACATGCGTGGTGGTG     +522
P--K--P--K--D--T--L--M--I--S--R--T--P--E--V--T--C--V--V--V--     +174

GACGTGAGCCACGAAGACCCTGAGGTCAAGTTCAACTGGTACGTGGACGGCGTGGAGGTG     +582
D--V--S--H--E--D--P--E--V--K--F--N--W--Y--V--D--G--V--E--V--     +194

CATAATGCCAAGACAAAGCCGCGGGAGGAGCAGTACAACAGCACGTACCGGGTGGTCAGC     +642
H--N--A--K--T--K--P--R--E--E--Q--Y--N--S--T--Y--R--V--V--S--     +214

GTCCTCACCGTCCTGCACCAGGACTGGCTGAATGGCAAGGAGTACAAGTGCAAGGTCTCC     +702
V--L--T--V--L--H--Q--D--W--L--N--G--K--E--Y--K--C--K--V--S--     +234

AACAAAGCCCTCCCAGCCCCCATCGAGAAAACCATCTCCAAAGCCAAAGGGCAGCCCCGA     +762
N--K--A--L--P--A--P--I--E--K--T--I--S--K--A--K--G--Q--P--R--     +254

GAACCACAGGTGTACACCCTGCCCCCATCCCGGGATGAGCTGACCAAGAACCAGGTCAGC     +822
E--P--Q--V--Y--T--L--P--P--S--R--D--E--L--T--K--N--Q--V--S--     +274

CTGACCTGCCTGGTCAAAGGCTTCTATCCCAGCGACATCGCCGTGGAGTGGGAGAGCAAT     +882
L--T--C--L--V--K--G--F--Y--P--S--D--I--A--V--E--W--E--S--N--     +294

GGGCAGCCGGAGAACAACTACAAGACCACGCCTCCCGTGCTGGACTCCGACGGCTCCTTC     +942
G--Q--P--E--N--N--Y--K--T--T--P--P--V--L--D--S--D--G--S--F--     +314

TTCCTCTACAGCAAGCTCACCGTGGACAAGAGCAGGTGGCAGCAGGGGAACGTCTTCTCA    +1002
F--L--Y--S--K--L--T--V--D--K--S--R--W--Q--Q--G--N--V--F--S--     +334

TGCTCCGTGATGCATGAGGCTCTGCACAACCACTACACGCAGAAGAGCCTCTCCCTGTCT    +1062
C--S--V--M--H--E--A--L--H--N--H--Y--T--Q--K--S--L--S--L--S--     +354

CCGGGTAAATGA
P--G--K--*
```

FIG. 9

```
ATGGGTGTACTGCTCACACAGAGGACGCTGCTCAGTCTGGTCCTTGCACTCCTGTTTCCA        -19
M---G---V---L---L---T---Q---R---T---L---L---S---L---V---L---A---L---L---F---P--   -7

AGCATGGCGAGCATGGCAATGCACGTGGCCCAGCCTGCTGTGGTACTGGCCAGCAGCCGA        +42
S---M---A---S---M---A---M---H---V---A---Q---P---A---V---V---L---A---S---S---R--  +14
              +1

GGCATCGCTAGCTTTGTGTGTGAGTATGCATCTCCAGGCAAAGCCACTGAGGTCCGGGTG       +102
G---I---A---S---F---V---C---E---Y---A---S---P---G---K---A---T---E---V---R---V--  +34

ACAGTGCTTCGGCAGGCTGACAGCCAGGTGACTGAAGTCTGTGCGGCAACCTACATGATG       +162
T---V---L---R---Q---A---D---S---Q---V---T---E---V---C---A---A---T---Y---M---M--  +54

GGGAATGAGTTGACCTTCCTAGATGATTCCATCTGCACGGGCACCTCCAGTGGAAATCAA       +222
G---N---E---L---T---F---L---D---D---S---I---C---T---G---T---S---S---G---N---Q--  +74

GTGAACCTCACTATCCAAGGACTGAGGGCCATGGACACGGGACTCTACATCTGCAAGGTG       +282
V---N---L---T---I---Q---G---L---R---A---M---D---T---G---L---Y---I---C---K---V--  +94

GAGCTCATGTACCCACCGCCATACTACGAGGGCATAGGCAACGGAACCCAGATTTATGTA       +342
E---L---M---Y---P---P---P---Y---Y---E---G---I---G---N---G---T---Q---I---Y---V-- +114

ATTGATCCAGAACCGTGCCCAGATTCTGATCAGGAGCCCAAATCTTCTGACAAAACTCAC       +402
I---D---P---E---P---C---P---D---S---D---Q---E---P---K---S---S---D---K---T---H-- +134

ACATCCCCACCGTCCCCAGCACCTGAACTCCTGGGGGGATCGTCAGTCTTCCTCTTCCCC       +462
T---S---P---P---S---P---A---P---E---L---L---G---G---S---S---V---F---L---F---P-- +154

CCAAAACCCAAGGACACCCTCATGATCTCCCGGACCCCTGAGGTCACATGCGTGGTGGTG       +522
P---K---P---K---D---T---L---M---I---S---R---T---P---E---V---T---C---V---V---V-- +174

GACGTGAGCCACGAAGACCCTGAGGTCAAGTTCAACTGGTACGTGGACGGCGTGGAGGTG       +582
D---V---S---H---E---D---P---E---V---K---F---N---W---Y---V---D---G---V---E---V-- +194

CATAATGCCAAGACAAAGCCGCGGGAGGAGCAGTACAACAGCACGTACCGTGTGGTCAGC       +642
H---N---A---K---T---K---P---R---E---E---Q---Y---N---S---T---Y---R---V---V---S-- +214

GTCCTCACCGTCCTGCACCAGGACTGGCTGAATGGCAAGGAGTACAAGTGCAAGGTCTCC       +702
V---L---T---V---L---H---Q---D---W---L---N---G---K---E---Y---K---C---K---V---S-- +234

AACAAAGCCCTCCCAGCCCCCATCGAGAAAACCATCTCCAAAGCCAAAGGGCAGCCCCGA       +762
N---K---A---L---P---A---P---I---E---K---T---I---S---K---A---K---G---Q---P---R-- +254

GAACCACAGGTGTACACCCTGCCCCCATCCCGGGATGAGCTGACCAAGAACCAGGTCAGC       +822
E---P---Q---V---Y---T---L---P---P---S---R---D---E---L---T---K---N---Q---V---S-- +274

CTGACCTGCCTGGTCAAAGGCTTCTATCCCAGCGACATCGCCGTGGAGTGGGAGAGCAAT       +882
L---T---C---L---V---K---G---F---Y---P---S---D---I---A---V---E---W---E---S---N-- +294

GGGCAGCCGGAGAACAACTACAAGACCACGCCTCCCGTGCTGGACTCCGACGGCTCCTTC       +942
G---Q---P---E---N---N---Y---K---T---T---P---P---V---L---D---S---D---G---S---F-- +314

TTCCTCTACAGCAAGCTCACCGTGGACAAGAGCAGGTGGCAGCAGGGGAACGTCTTCTCA      +1002
F---L---Y---S---K---L---T---V---D---K---S---R---W---Q---Q---G---N---V---F---S-- +334

TGCTCCGTGATGCATGAGGCTCTGCACAACCACTACACGCAGAAGAGCCTCTCCCTGTCT      +1062
C---S---V---M---H---E---A---L---H---N---H---Y---T---Q---K---S---L---S---L---S-- +354

CCGGGTAAATGA
P---G---K---*
```

FIG. 13

ONCOSTATIN M SIGNAL PEPTIDE

```
 M   G   V   L   L   T   Q   R   T   L   L   S   L   V   L
ATG GGT GTA CTG CTC ACA CAG AGG ACG CTG CTC AGT CTG GTC CTT    45
                                    ← -1 +1

A   L   L   F   P   S   M   A   S   M   A   M   H   V   A
GCA CTC CTG TTT CCA AGC ATG GCG AGC ATG GCA ATG CAC GTG GCC    90

Q   P   A   V   V   L   A   S   S   R   G   I   A   S   F
CAG CCT GCT GTG GTA CTG GCC AGC AGC CGA GGC ATC GCC AGC TTT   135

V   C   E   Y   A   S   P   G   K   A   T   E   V   R   V
GTG TGT GAG TAT GCA TCT CCA GGC AAA GCC ACT GAG GTC CGG GTG   180

T   V   L   R   Q   A   D   S   Q   V   T   E   V   C   A
ACA GTG CTT CGG CAG GCT GAC AGC CAG GTG ACT GAA GTC TGT GCG   225

A   T   Y   M   M   G   N   E   L   T   F   L   D   D   S
GCA ACC TAC ATG ATG GGG AAT GAG TTG ACC TTC CTA GAT GAT TCC   270

I   C   T   G   T   S   S   G   N   Q   V   N   L   T   I
ATC TGC ACG GGC ACC TCC AGT GGA AAT CAA GTG AAC CTC ACT ATC   315

Q   G   L   R   A   M   D   T   G   L   Y   I   C   K   V
CAA GCA CTG AGG GCC ATG GAC ACG GGA CTC TAC ATC TGC AAG GTG   360
                                                GLYCOSYLATION SITE
 E   L   M   Y   P   P   P   Y   Y   L   G   I   G   N   G
GAG CTC ATG TAC CCA CCG CCA TAC TAC CTG GGC ATA GGC AAC GGA   405

T   Q   I   Y   V   I   D   P   E   P   C   P   D   S   D
ACC CAG ATT TAT GTA ATT GAT CCA GAA CCG TGC CCA GAT TCT GAC   450

F   L   L   W   I   L   A   A   V   S   S   G   L   F   F
TTC CTC CTC TGG ATC CTT GCA GCA GTT AGT TCG GGG TTG TTT TTT   495

Y   S   F   L   L   T   A   V   S   L   S   K   M   L   K
TAT AGC TTT CTC CTC ACA GCT GTT TCT TTG AGC AAA ATG CTA AAG   540

K   R   S   P   L   T   T   G   V   Y   V   K   M   P   P
AAA AGA AGC CCT CTT ACA ACA GGG GTC TAT GTG AAA ATG CCC CCA   585

T   E   P   E   C   E   K   Q   F   Q   P   Y   F   I   P
ACA GAG CCA GAA TGT GAA AAG CAA TTT CAG CCT TAT TTT ATT CCC   630

I   N
ATC AAT                                                        636
```

METHODS FOR TREATING IMMUNE DISORDERS ASSOCIATED WITH GRAFT TRANSPLANTATION WITH SOLUBLE CTLA4 MUTANT MOLECULES

RELATED APPLICATION

This application claims priority benefit under Title 35 §119 (e) of U.S. provisional Application No. 60/668,774, filed Apr. 6, 2005, the contents of which are herein incorporated by reference.

Throughout this application various publications are referenced. The disclosures of these publications in their entireties are hereby incorporated by reference into this application in order to more fully describe the state of the art to which this invention pertains.

FIELD OF THE INVENTION

The present invention relates to the use of soluble CTLA4 mutant molecules, with increased binding avidity to CD80 (B7-1) and CD86 (B7-2) compared with wild type CTLA4, in the treatment of immune disorders associated with graft transplantation.

BACKGROUND OF THE INVENTION

Given the central role of T-cells in transplant rejection, a common goal among current immunosuppressive therapies is to block T-cell activation and function (Sayegh M H, Turka L A. The role of T-cell costimulatory activation pathways in transplant rejection. N Engl J Med 1998;338(25):1813-21). T-cells require both an antigen-specific (Signal 1) and co-stimulatory signal (Signal 2) for full activation (Lenschow D J, Walunas T L, Bluestone J A. CD28/B7 system of T cell costimulation. Annu Rev Immunol 1996;14:233-58). One of the best-characterized co-stimulatory pathways involves the CD28-CD80/86 (B7-1/2) interaction (Linsley P S, Ledbetter J A. The role of the CD28 receptor during T cell responses to antigen. Annu Rev Immunol 1993; 11:191-212). Cytotoxic T-lymphocyte antigen 4 (CTLA4) binds to CD80/86 with higher avidity than CD28, and is transiently expressed on T-cells following their activation, where it interrupts the interaction between CD28 and CD80/86 (Oosterwegel M A, Greenwald R J, Mandelbrot D A, Lorsbach R B, Sharpe A H. CTLA-4 and T cell activation. Curr Opin Immunol 1999;11 (3):294-300.). This creates a negative feedback signal for T-cell activation.

Intervention in this pathway has been previously pursued with CTLA4Ig. CTLA4Ig has been successfully used as a strategy to treat T-cell-mediated autoimmune disorders such as rheumatoid arthritis (Kremer J M, Westhovens R, Leon M, et al. Treatment of rheumatoid arthritis by selective inhibition of T-cell activation with fusion protein CTLA4Ig. N Engl J Med 2003;349(20):1907-15) and psoriasis (Abrams J R, Lebwohl M G, Guzzo C A, et al. CTLA4Ig-mediated blockade of T-cell costimulation in patients with psoriasis vulgaris. J Clin Invest 1999; 103(9):1243-52).

LEA29Y has been studied in non-human primate transplant models alone and in combination with other immunosuppressive agents. Christian Larsen et al (C. Larsen, T. Pearson, A. Adams, P. Tso, N. Shirasugi, E. Strobert, D. Anderson, S. Cowan, K. Price, J. Naemura, J. Emswiler, J. Greene, L. A. Turk, J. Bajorath, R. Townsend, D. Hagerty, P. Linsley and R. Peach; Rational Development of LEA29Y (belatacept), a High-Affinity Variant of CTLA4-Ig with Potent Immunosuppressive Properties; American Journal of Transplantation; Vol. 5, Issue 3, March 2005, p. 443) have shown the enhanced immunosuppressive activity of LEA29Y when compared to CTLA4-Ig in a non-human primate model utilized to study renal allograft rejection. LEA29Y was administered intraoperatively (10 mg/kg intravenously), on day 4 (15 mg/kg) and on post-operative days 14, 28, 42, 56 and 70 (20 mg/kg intravenously). CTLA4Ig (16 mg/kg) was administered intraoperatively and on post-operative days 4, 8, 11 and 16. The treatment regimen also included MMF (15 mg/kg bid s.c. on days 0-14, qd on days 15-180), methylprednisolone (subcutaneouse injection according to the following schedule, day 0: 20 mg, day 1: 16 mg, day 3: 8 mg, day 4: 4mg, day 5-14: 3mg, day 15-180: 1 mg) and basiliximab (0.3 gm/kg i.v. on day 0 and 4). Survival of renal allograft recipients treated with LEA29Y was clearly superior to that of a group treated with CTLA4-Ig despite comparable serum concentrations. Control recipients treated with albumin showed a similar median survival time to the group treated with CTLA4-Ig. However, despite ongoing treatment with LEA29Y, all recipients experienced a significant decline in renal function (rise in serum creatinine).

Andrew Adams et al (A. Adams, N. Shirasugi, T. Jones, M. Durham, E. Strobert, S. Cowan, P. Rees, R. Hendrix, K. Price, N. Kenyon, D, Hagerty, R. Townsend, D. Hollenbaugh, T. Pearson and C. Larsen; Development of a Chimeric Anti-CD40 Monoclonal Antibody That Synergizes with LEA29Y to Prolong Islet Allograft Survival; The Journal of Immunology; January 2005; 174; p. 542) have shown that the combination of LEA29Y and Chi220 (a chimeric anti-human CD40 mab) act synergistically in a non-human primate model of pancreatic islet transplantation to prolong allograft survival. LEA29Y was administered intravenously intra-operatively (20 mg/kg);on postoperative days 4, 7 and 14; then every 2 weeks until day 100. Additional doses (20 mg/kg) were administered monthly through 6 months. Four protocols were tested: 1) LEA29Y alone, 2) Chi220 (anti-CD40), 3)LEA29Y combined with Chi220, and 4) LEA29Y combined with anti-CD20.

Andrew Adams et al (A. Adams, N. Shirasugi, M. Durham, E. Strobert, D. Anderson, P. Rees, S. Cowan, H. Xu, Y. Blinder, M. Cheung, D. Hollenbaugh, N. Kenyon, T. Pearson and C. Larsen; Calcineurin Inhibitor-Free CD28 Blockade-Based Protocol Protects Allogeneic Islets in Nonhuman Primates; Diabetes, Vol. 51(2), February 2002, p. 265) have shown that the combination of LEA29Y, rapamycin, and anti-IL-2R mAb significantly prolonged islet allograft survival. in a non-human primate model of pancreatic islet transplantation. LEA29Y was administered intravenously intra-operatively (10 mg/kg) and on postoperative day 4 (15 mg/kg). Additional does of 20 mg/kg were given on postoperative day 14 and every 2 weeks until postoperative day 154.

During 2003 more than 25,000 organs were transplanted in the US. Kidney transplantation represented approximately 60% of the solid organ transplants followed by liver transplants at 21%, heart at 8%, lung at 4% and the remaining 7% represented other organ transplants such as pancreas and intestine. (OPTN/SRTR Annual Report 2004 at www.optn.org)

Renal transplantation is the most effective treatment for end-stage renal disease. It provides improved survival and quality of life (QoL). Maintenance of a functioning renal transplant mandates lifelong immunosuppressive therapy to prevent immune destruction of the graft. Current immunosuppressive regimens yield 1-year survival rates of 89% for cadaveric and 94% for living-donor grafts. Over time, however, there is progressive loss of both subjects and grafts.

Five-year survival for cadaveric and living-related donor renal transplants is 66% and 79%, respectively.(United Network for Organ Sharing Renal Transplant Registry 2003 at www.unos.org)

The most common causes of long-term subject and graft loss are cardiovascular disease and chronic allograft nephropathy (CAN), respectively.(L. C. Paul, Chronic allograft nephropathy—A model of impaired repair rom injury? Nephrol Dial Transplant 2000;15:149-151) Paradoxically, the principal therapies for renal transplantation, the calcineurin inhibitors (CNIs), CsA and tacrolimus, directly contribute to long-term allograft loss and subject death, since they are inherently nephrotoxic, and also cause or exacerbate cardiovascular risks, including hypertension, hypercholesterolemia, and diabetes mellitus. Nonetheless, these agents form the cornerstone of all conventional immunosuppressive regimens for renal transplantation.

At present, there are no approved agents that can replace CNIs as cornerstone maintenance immunosuppressant therapy in a broad range of subjects. One agent, sirolimus (rapamycin, Rapamune® from Wyeth/Ayerst), has been approved for use in a CNI-sparing regimen. CNIs, however, must still be used with sirolimus for at least 3 months post-transplantation. More importantly, sirolimus has been approved as a CNI-sparing agent in this setting only for subjects at low to moderate risk of graft loss. Thus, for those at higher risk of graft loss, in whom avoidance of the nephrotoxic effects of CNIs would be of greatest benefit, there is no approved alternative to CNIs.

Therefore, there is an unmet medical need for immunosuppressive agents that can provide acceptable control of the alloimmune response comparable to standard of practice therapies without toxicities that contribute to long-term subject death and graft loss. Ideally, the agent would be useful not only in low-risk subjects, but also in subjects at higher risk of graft loss.

SUMMARY OF INVENTION

The present invention provides methods for treating immune disorders associated with graft transplantation by administering CTLA4 mutant molecules which bind with greater avidity to the CD80 and/or CD86 antigen than wild type CTLA4 or non-mutated CTLA4Ig. The CTLA4 molecules have a first amino acid sequence comprising the extracellular domain of CTLA4, where certain amino acid residues within the S25-R33 region and M97-G107 region are mutated. The mutant molecules of the invention may also include a second amino acid sequence which increases the solubility of the mutant molecule.

One example of a CTLA4 mutant molecule is L104EA29YIg (FIG. 7, SEQ ID NOS: 3 and 4), as described herein. Another example of a CTLA4 mutant molecule is L104EIg (FIG. 8, SEQ ID NOS: 5 and 6), as described herein. L104EA29YIg and L104EIg bind CD80 and CD86 more avidly than CTLA4Ig.

Administration of the CTLA4 mutant molecules of the invention may be performed over various times. Typically, administration regimens included an early phase, in which doses are higher and the frequency of administration is increased during the period of greatest immunologic risk, followed by a maintenance phase. The early phase may range from the first 3 to 6 months post-transplantation. The administration regimen during early phase may vary depending on the status of the recipient/graft.

In one embodiment the present invention provides a method for treating an immune disorder associated with graft transplantation by administering to a subject an effective dose of a CTLA4 mutant molecule with an extracellular domain of CTLA4 as shown in SEQ ID NO:8 beginning with alanine at position 26 or methionine at position 27 and ending with aspartic acid at position 50, or a portion thereof. Additionally, in the extracellular domain or portion thereof an alanine at position 55 is substituted with a tyrosine, and a leucine at position 130 is substituted with a glutamic acid. Further the administration regimen comprises an early phase regimen, wherein the early phase regimen may range from the first 3 to 6 months post-transplantation and involves administration that initially is more frequent than monthly.

In another embodiment the present invention provides a method for treating an immune disorder associated with graft transplantation by administering to a subject an effective dose of a CTLA4 mutant molecule with an amino acid sequence beginning with methionine at position 27 and ending with aspartic acid at position 150 of SEQ ID NO:4, or with an amino acid sequence beginning with alanine at position 26 and ending with aspartic acid at position 150 of SEQ ID NO:4. Further the CTLA4 mutant molecule administration regimen comprises an early phase regimen, wherein the early phase regimen may range from the first 3 to 6 months post-transplantation and involves administration that initially is more frequent than monthly.

BRIEF DESCRIPTION OF THE FIGURES

FIG. 7 (SEQ ID NOS: 3 and 4) depicts a nucleotide and amino acid sequence of a CTLA4 mutant molecule ("L104EA29YIg") comprising a signal peptide; a mutated extracellular domain of CTLA4 starting at methionine at position +1 and ending at aspartic acid at position +124, or starting at alanine at position −1 and ending at aspartic acid at position +124; and an Ig region as described in Example 1, infra. SEQ ID NOS: 3 and 4 depict a nucleotide and amino acid sequence, respectively, of a CTLA4 mutant molecule ("L104EA29YIg") comprising a signal peptide; a mutated extracellular domain of CTLA4 starting at methionine at position +27 and ending at aspartic acid at position +150, or starting at alanine at position +26 and ending at aspartic acid at position +150; and an Ig region.

FIG. 8 (SEQ ID NOS: 5 and 6) depicts a nucleotide and amino acid sequence of a CTLA4 mutant molecule ("L104EIg") comprising a signal peptide; a mutated extracellular domain of CTLA4 starting at methionine at position +1 and ending at aspartic acid at position +124, or starting at alanine at position −1 and ending at aspartic acid at position +124; and an Ig region as described in Example 1, infra. SEQ ID NOS: 5 and 6 depict a nucleotide and amino acid sequence, respectively, of a CTLA4 mutant molecule ("L104EIg") comprising a signal peptide; a mutated extracellular domain of CTLA4 starting at methionine at position +27 and ending at aspartic acid at position +150, or starting at alanine at position +26 and ending at aspartic acid at position +150; and an Ig region.

FIG. 9 (SEQ ID NOS: 7 and 8) depicts a nucleotide and amino acid sequence of a CTLA4Ig having a signal peptide; a wild type amino acid sequence of the extracellular domain of CTLA4 starting at methionine at position +1 to aspartic acid at position +124, or starting at alanine at position −1 to aspartic acid at position +124; and an Ig region. SEQ ID NOS: 7 and 8 depict a nucleotide and amino acid sequence, respectively, of a CTLA4Ig comprising a signal peptide; a wild type amino acid sequence of the extracellular domain CTLA4 starting at methionine at position +27 and ending at aspartic acid at position +150, or starting at alanine at position +26 and ending at aspartic acid at position +150; and an Ig region.

FIG. 11B shows an expanded view of the S25-R33 region and the MYPPPY region indicating the location and side-chain orientation of the avidity enhancing mutations, L104 and A29.

FIG. 13 depicts nucleotide and amino acid sequence of CTLA4 receptor (SEQ ID NOS: 9 and 10).

DETAILED DESCRIPTION OF THE INVENTION

Definitions

Figure 1:
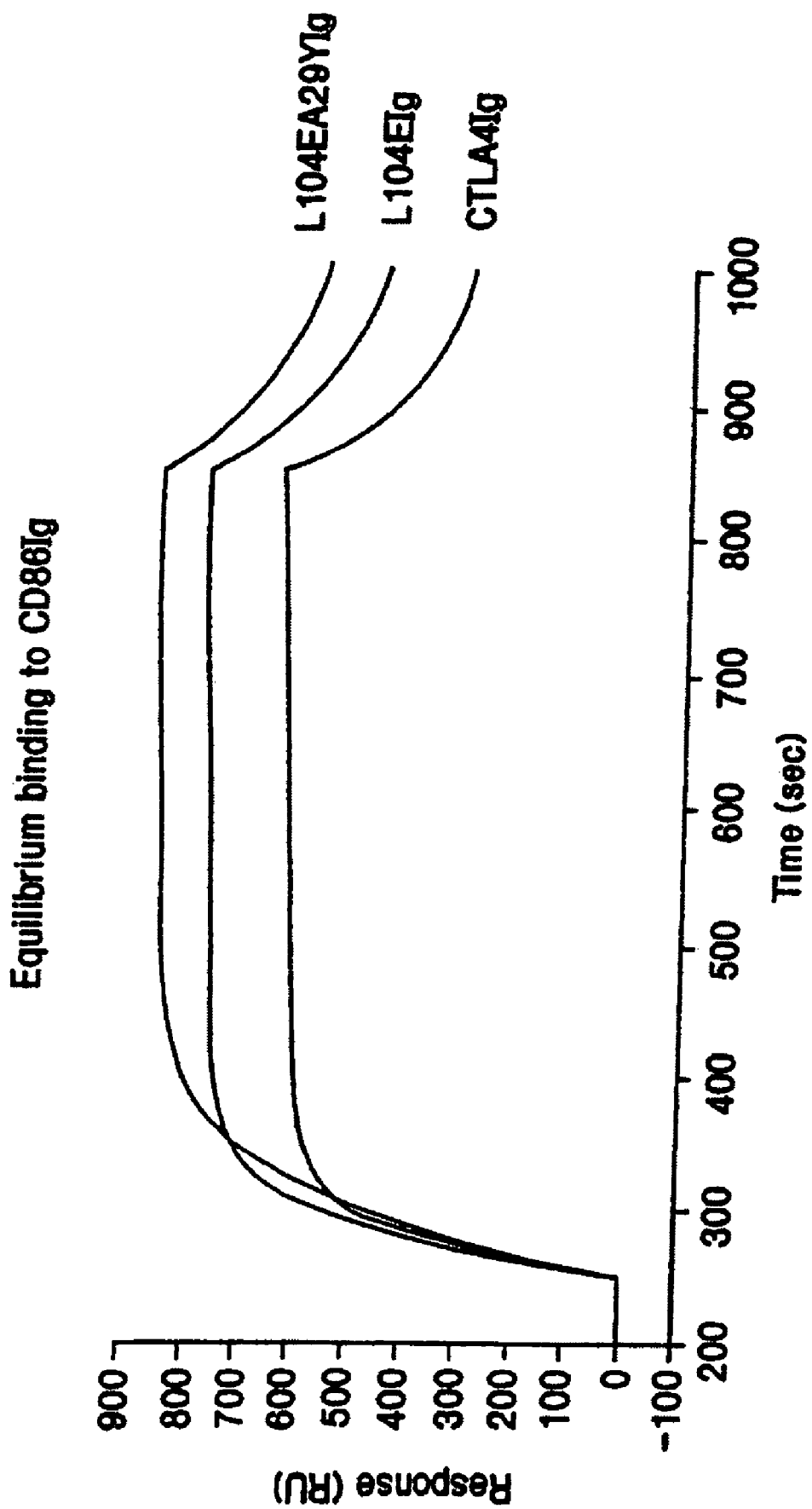
FIG. 1 shows the equilibrium binding analysis of L104EA29YIg, L104EIg, and wild-type CTLA4Ig to CD86Ig.

All scientific and technical terms used in this application have meanings commonly used in the art unless otherwise specified. As used in this application, the following words or phrases have the meanings specified.

As used herein, "ligand" refers to a molecule that specifically recognizes and binds another molecule, for example, a ligand for CTLA4 is a B7 molecule.

As used herein "wild type CTLA4" or "non-mutated CTLA4" has the amino acid sequence of naturally occurring, full length CTLA4 as shown in FIG. 13 (SEQ ID NOS: 9 and 10; also as described U.S. Pat. Nos. 5,434,131, 5,844,095, 5,851,795), or any portion or derivative thereof, that recognizes and binds a B7 or interferes with a B7 so that it blocks binding to CD28 and/or CTLA4 (e.g., endogenous CD28 and/or CTLA4). In particular embodiments, the extracellular domain of wild type CTLA4 begins with methionine at position +1 and ends at aspartic acid at position +124, or the extracellular domain of wild type CTLA4 begins with alanine at position −1 and ends at aspartic acid at position +124. Wild type CTLA4 is a cell surface protein, having an N-terminal extracellular domain, a transmembrane domain, and a C-terminal cytoplasmic domain. The extracellular domain binds to target molecules, such as a B7 molecule. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. Alternatively, the signal peptide may not be removed completely, generating molecules that begin before the common starting amino acid methionine. Thus, the mature CTLA4 protein may start at methionine at position +1 or alanine at position −1. The mature form of the CTLA4 molecule includes the extracellular domain or any portion thereof, which binds to B7.

"CTLA4Ig" is a soluble fusion protein comprising an extracellular domain of wildtype CTLA4 joined to an Ig tail, or a portion thereof that binds a B7. A particular embodiment comprises the extracellular domain of wild type CTLA4 (as shown in FIG. 9, SEQ ID NOS: 7 and 8) starting at methionine at position +1 and ending at aspartic acid at position +124; or starting at alanine at position −1 to aspartic acid at position +124; a junction amino acid residue glutamine at position +125; and an immunoglobulin portion encompassing glutamic acid at position +126 through lysine at position +357 or glycine at position +356 (DNA encoding CTLA4Ig was deposited on May 31, 1991 with the American Type Culture Collection (ATCC), 10801 University Blvd., Manassas, Va. 20110-2209 under the provisions of the Budapest Treaty, and has been accorded ATCC accession number ATCC 68629; Linsley, P., et al., 1994 *Immunity* 1:793-80. CTLA4Ig-24, a Chinese Hamster Ovary (CHO) cell line expressing CTLA4Ig was deposited on May 31, 1991 with ATCC identification number CRL-10762). The soluble CTLA4Ig molecules may or may not include a signal (leader) peptide sequence.

As used herein, a "fusion protein" is defined as one or more amino acid sequences joined together using methods well known in the art and as described in U.S. Pat. Nos. 5,434,131 or 5,637,481. The joined amino acid sequences thereby form one fusion protein.

As used herein, "soluble" refers to any molecule, or fragments and derivatives thereof, not bound or attached to a cell, i.e., circulating. For example, CTLA4, B7 or CD28 can be made soluble by attaching an immunoglobulin (Ig) moiety to the extracellular domain of CTLA4, B7 or CD28, respectively. Alternatively, a molecule such as CTLA4 can be rendered soluble by removing its transmembrane domain.

As used herein "the extracellular domain of CTLA4" is the portion of CTLA4 that recognizes and binds CTLA4 ligands, such as B7 molecules. For example, an extracellular domain of CTLA4 comprises methionine at position +1 to aspartic acid at position +124 (FIG. 13, SEQ ID NOS: 9 and 10). Alternatively, an extracellular domain of CTLA4 comprises alanine at position −1 to aspartic acid at position +124 (FIG. 13, SEQ ID NOS: 9 and 10). The extracellular domain includes fragments or derivatives of CTLA4 that bind a B7 molecule. The extracellular domain of CTLA4 as shown in FIG. 13 (SEQ ID NOS: 9 and 10) may also include mutations that change the binding avidity of the CTLA4 molecule for a B7 molecule.

As used herein, a "CTLA4 mutant molecule" means wild-type CTLA4 as shown in (SEQ ID NOS: 9 and 10) or any portion or derivative thereof, that has a mutation or multiple mutations (preferably in the extracellular domain of wildtype CTLA4). A CTLA4 mutant molecule has a sequence that it is similar but not identical to the sequence of wild type CTLA4 molecule, but still binds a B7. The mutations may include one or more amino acid residues substituted with an amino acid having conservative (e.g., substitute a leucine with an isoleucine) or non-conservative (e.g., substitute a glycine with a tryptophan) structure or chemical properties, amino acid deletions, additions, frameshifts, or truncations. CTLA4 mutant molecules may include a non-CTLA4 molecule therein or attached thereto. The mutant molecules may be soluble (i.e., circulating) or bound to a cell surface. Additional CTLA4 mutant molecules include those described in U.S. patent application Ser. Nos. 09/865,321, 60/214,065 and 60/287,576; in U.S. Pat. Nos. 6,090,914 5,844,095 and 5,773,253; and as described by Peach, R. J., et al., in *J Exp Med* 180:2049-2058 (1994)). CTLA4 mutant molecules can be made synthetically or recombinantly.

"L104EA29YIg" is a fusion protein that is a soluble CTLA4 mutant molecule comprising an extracellular domain of wildtype CTLA4 with amino acid changes A29Y (a tyrosine amino acid residue substituting for an alanine at position 29) and L104E (a glutamic acid amino acid residue substituting for a leucine at position +104), or a portion thereof that binds a B7 molecule, joined to an Ig tail (included in FIG. 7, SEQ ID NOS: 3 and 4; DNA encoding L104EA29YIg was deposited on Jun. 20, 2000 with ATCC number PTA-2104; copending in U.S. patent application Ser. Nos. 09/579,927, 60/287,576 and 60/214,065, incorporated by reference herein). The soluble L104EA29YIg molecules used in the methods and/or kits of the invention may or may not include a signal (leader) peptide sequence. Typically, in the methods and/or kits of the invention, the molecules do not include a signal peptide sequence.

As used herein, the term "mutation" means a change in the nucleotide or amino acid sequence of a wildtype molecule, for example, a change in the DNA and/or amino acid sequences of the wild-type CTLA4 extracellular domain. A mutation in DNA may change a codon leading to a change in the amino acid sequence. A DNA change may include substitutions, deletions, insertions, alternative splicing, or truncations. An amino acid change may include substitutions, deletions, insertions, additions, truncations, or processing or cleavage errors of the protein. Alternatively, mutations in a nucleotide sequence may result in a silent mutation in the amino acid sequence as is well understood in the art. In that regard, certain nucleotide codons encode the same amino acid. Examples include nucleotide codons CGU, CGG, CGC, and CGA encoding the amino acid, arginine (R); or codons GAU, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid    | Symbol | One Letter Symbol | Codons                  |
| ------------- | ------ | ----------------- | ----------------------- |
| Alanine       | Ala    | A                 | GCU, GCC, GCA, GCG      |
| Cysteine      | Cys    | C                 | UGU, UGC                |
| Aspartic Acid | Asp    | D                 | GAU, GAC                |
| Glutamic Acid | Glu    | E                 | GAA, GAG                |
| Phenylalanine | Phe    | F                 | UUU, UUC                |
| Glycine       | Gly    | G                 | GGU, GGC, GGA, GGG      |
| Histidine     | His    | H                 | CAU, CAC                |
| Isoleucine    | Ile    | I                 | AUU, AUC, AUA           |
| Lysine        | Lys    | K                 | AAA, AAG                |
| Leucine       | Leu    | L                 | UUA, UUG, CUU, CUC, CUA, CUG |
| Methionine    | Met    | M                 | AUG                     |
| Asparagine    | Asn    | N                 | AAU, AAC                |

-continued

| Amino Acid | Symbol | One Letter Symbol | Codons              |
| ---------- | ------ | ----------------- | ------------------- |
| Proline    | Pro    | P                 | CCU, CCC, CCA, CCG  |
| Glutamine  | Gln    | Q                 | CAA, CAG            |
| Arginine   | Arg    | R                 | CGU, CGC, CGA, CGG, AGA, AGG |
| Serine     | Ser    | S                 | UCU, UCC, UCA, UCG, AGU, AGC |
| Threonine  | Thr    | T                 | ACU, ACC, ACA, ACG  |
| Valine     | Val    | V                 | GUU, GUC, GUA, GUG  |
| Tryptophan | Trp    | W                 | UGG                 |
| Tyrosine   | Tyr    | Y                 | UAU, UAC            |

The mutant molecule may have one or more mutations.

As used herein, a "non-CTLA4 protein sequence" or "non-CTLA4 molecule" means any protein molecule that does not bind B7 and does not interfere with the binding of CTLA4 to its target. An example includes, but is not limited to, an immunoglobulin (Ig) constant region or portion thereof. Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos. 5,637,481, 5,844,095 and 5,434,131).

As used herein, a "fragment" or "portion" is any part or segment of a CTLA4 molecule, preferably the extracellular domain of CTLA4 or a part or segment thereof, that recognizes and binds its target, e.g., a B7 molecule. The extracellular domain of CTLA4 may include mutations that change the binding avidity of the CTLA4 molecule for a B7 molecule.

As used herein, "B7" refers to the B7 family of molecules including, but not limited to, B7-1 (CD80), B7-2 (CD86) and B7-3 that may recognize and bind CTLA4 and/or CD28.

As used herein, "B7-positive cells" are any cells with one or more types of B7 molecules expressed on the cell surface.

As used herein, a "derivative" is a molecule that shares sequence homology and activity of its parent molecule. For example, a derivative of CTLA4 includes a soluble CTLA4 molecule having an amino acid sequence at least 70% similar to the extracellular domain of wildtype CTLA4, and which recognizes and binds B7 e.g., CTLA4Ig or soluble CTLA4 mutant molecule L104EA29YIg.

As used herein, to "regulate" an immune response is to activate, stimulate, up-regulate, inhibit, block, down-regulate or modify the immune response. The autoimmune diseases described herein, may be treated by regulating an immune response e.g., by regulating functional CTLA4- and/or CD28-positive cell interactions with B7-positive cells. For example, a method for regulating an immune response comprises contacting the B7-positive cells with a soluble CTLA4 molecule of the invention so as to form soluble CTLA4/B7 complexes, the soluble CTLA4 molecule interfering with reaction of an endogenous CTLA4 and/or CD28 molecule with said B7 molecule.

As used herein, to "block" or "inhibit" a receptor, signal or molecule means to interfere with the activation of the receptor, signal or molecule, as detected by an art-recognized test. Blockage or inhibition may be partial or total. For example, blockage of a cell-mediated immune response can be detected by determining the functionality of the transplant, such as the serum creatinine concentrations following renal transplantation.

As used herein, "blocking B7 interaction" means to interfere with the binding of B7 to its ligands, such as CD28 and/or CTLA4, thereby obstructing T-cell and B7-positive cell interactions. Examples of agents that block B7 interactions include, but are not limited to, molecules such as an antibody (or portion or derivative thereof) that recognizes and binds to the any of CTLA4, CD28 or B7 molecules (e.g., B7-1, B7-2); a soluble form (or portion or derivative thereof) of the molecules such as soluble CTLA4; a peptide fragment or other small molecule designed to interfere with the cell signal through the CTLA4/CD28/B7-mediated interaction. In a preferred embodiment, the blocking agent is a soluble CTLA4 mutant molecule, such as L104EA29YIg (ATCC PTA-2104).

As used herein, "treat" or "treating" a disorder or disease means to manage a disease or disorder by medicinal or other therapies. Treatment of a disease or disorder may suppress immune-mediated events associated with a disease, ameliorate the symptoms of a disease or disorder, reduce the severity of a disease or disorder, alter the course of disease or disorder progression and/or ameliorate or cure the basic disease or disorder problem. For example, to treat an immune disorder associated with graft transplantation may be accomplished by regulating an immune response e.g., by regulating functional CTLA4- and/or CD28-positive cell interactions with B7-positive cells. Alternatively, treating an immune disease or disorder may be accomplished by preventing or inhibiting the disease or disorder from occurring or progressing through the use of the compositions described herein. For example, treating renal transplant rejection includes inhibition of renal transplant rejection as measured by glomerular filtration rate (GFR). For example treating immune disorders associated with graft transplantation includes prophylaxis of organ rejection by administration of L104EA29YIg. Further, treating immune disorders associated with graft transplantation may prolong the survival of the host and transplanted organ.

As used herein, "immune system disease" includes any disease mediated by T-cell interactions with B7-positive cells including, but not limited to, autoimmune diseases, immunoproliferative diseases, and immune disorders associated with graft transplantation.

As used herein, "immune disorders associated with graft transplantation" means any transplant related disease mediated by T-cell interactions with B7-positive cells including, but not limited to, immune disorders associated with graft transplantation rejection, graft related disorders, graft versus host disease (GVHD) (e.g., such as may result from bone marrow transplantation, or in the induction of tolerance), rejection of the graft or transplant including acute rejection of the graft or transplant and chronic rejection of the graft or transplant. The graft may be solid organ allografts or xenografts, tissue or cell allografts or xenografts or external anatomy allografts or xenografts, including but not limited to skin, islet cells (also known as islets), muscles, hepatocytes, neurons, heart, liver, kidney, lung, appendages, limbs, nose, ear or face.

As used herein, immunoproliferative diseases include, but are not limited to, T cell lymphoma; T cell acute lymphoblastic leukemia; testicular angiocentric T cell lymphoma; and benign lymphocytic angiitis.

As used herein autoimmune diseases include, but are not limited to diseases such as lupus (e.g., lupus erythematosus, lupus nephritis), psoriasis; Hashimoto's thyroiditis, primary myxedema, Graves' disease, pernicious anemia, autoimmune atrophic gastritis, Addison's disease, diabetes (e.g., insulin dependent diabetes mellitus, type I diabetes mellitus, type II diabetes mellitus), good pasture's syndrome, myasthenia gravis, pemphigus, Crohn's disease, inflamatory bowl disease (IBD), sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjogren's syndrome, rheumatic diseases (e.g., rheumatoid arthritis, psoriatic arthritis), polymyositis, scleroderma, and mixed connective tissue disease.

In order that the invention herein described may be more fully understood, the following description is set forth.

Compositions and Methods of the Invention

The present invention provides a new class of immunosuppressive therapy for transplantation. It is a fusion protein that binds to the B7 molecules on the surface of antigen-presenting cells (APCs) inhibiting requisite co-stimulation for T-cell activation. The soluble CTLA4 mutant molecules of the invention differ from existing immunosuppressants in the restricted distribution of its molecular target and the specificity of its effect. The present invention provides soluble CTLA4 mutant molecules that recognize and bind CD80 and/or CD86. In some embodiments, the soluble CTLA4 mutants have a higher avidity to CD80 and/or CD86 than CTLA4Ig. For example, L104EA29YIg binds approximately 2-fold more avidly than wild type CTLA4Ig (hereinafter referred to as CTLA4Ig) to CD80 and approximately 4-fold more avidly to CD86. This stronger binding results in L104EA29YIg being more affective than CTLA4Ig at blocking immune responses.

One embodiment of the present invention provides methods for treating immune system diseases. The methods comprise administering a therapeutic composition, comprising soluble CTLA4 mutant molecules disclosed herein, to a subject in an amount effective to relieve at least one of the symptoms associated with immune system diseases. Additionally, the soluble CTLA4 mutant molecules disclosed herein may provide long-term therapy for immune system diseases by blocking the T-cell/B7-positive cell interactions, thereby blocking T-cell activation/stimulation by co-stimulatory signals such as B7 binding to CD28, leading to induction of T-cell anergy or tolerance. Immune system diseases include, but are not limited to, autoimmune diseases, immunoproliferative diseases, and immune disorders associated with graft transplantation discussed above.

Another embodiment provides methods for inducing tolerance in a subject having immune disorders associated with graft transplantation by administering a therapeutic composition comprising soluble CTLA4 mutant molecules disclosed herein.

The soluble CTLA4 mutant molecules disclosed herein exhibit inhibitory properties in vivo. Under conditions where T-cell/B7-positive cell interactions, for example T cell/B cell interactions, are occurring as a result of contact between T cells and B7-positive cells, binding of introduced CTLA4 mutant molecules to react to B7-positive cells, for example B cells, may interfere, i.e., inhibit, the T cell/B7-positive cell interactions resulting in regulation of immune responses.

Another embodiment provides methods for regulating immune responses. Immune responses downregulated (reduced) by the soluble CTLA4 mutant molecules disclosed herein may be by way of inhibiting or blocking an immune response already in progress or may involve preventing the induction of an immune response. The soluble CTLA4 mutant molecules disclosed herein may inhibit the functions of activated T cells, such as T lymphocyte proliferation, cytokine secretion and/or cytokine production, by suppressing T cell responses or by inducing specific tolerance in T cells, or both. Further, the soluble CTLA4 mutant molecules disclosed herein, interfering with the CTLA4/CD28/B7 pathway may inhibit T-cell proliferation and/or cytokine secretion, and thus result in reduced tissue destruction and induction of T-cell unresponsiveness or anergy.

CTLA4 mutant molecules comprise at least the extracellular domain of CTLA4, or portions thereof that bind CD80 and/or CD86. The extracellular portion of a CTLA4 mutant molecule comprises an amino acid sequence starting with methionine at position +1 through aspartic acid at position +124 (FIG. 7,SEQ ID NOS: 3 and 4; or FIG. 8, SEQ ID NOS: 5 and 6). Alternatively, the extracellular portion of the CTLA4 can comprise an amino acid sequence starting with alanine at position −1 through aspartic acid at position +124 (FIG. 7, SEQ ID NOS: 3 and 4; or FIG. 8, SEQ ID NOS: 5 and 6).

In one embodiment, the soluble CTLA4 mutant molecule is a fusion protein comprising the extracellular domain of CTLA4 having one or more mutations in a region of an amino acid sequence beginning with serine at +25 and ending with arginine at +33 (S25-R33). For example, the alanine at position +29 of wild type CTLA4 can be substituted with tyrosine (codons: UAU, UAC). Alternatively, alanine can be substituted with leucine (codons: UUA, UUG, CUU, CUC, CUA, CUG), phenylalanine (codons: UUU, UUC), tryptophan (codon: UGG), or threonine (codons: ACU, ACC, ACA, ACG). As persons skilled in the art will readily understand, the uracil (U) nucleotide of the RNA sequence corresponds to the thymine (T) nucleotide of the DNA sequence.

In another embodiment, the soluble CTLA4 mutant molecule is a fusion protein comprising the extracellular domain of CTLA4 having one or more mutations in or near a region of an amino acid sequence beginning with methionine at +97 and ending with glycine at +107 (M97-G107). For example, leucine at position +104 of wild type CTLA4 can be substituted with glutamic acid (codons: GAA, GAG). A CTLA4 mutant molecule having this substitution is referred to herein as L104EIg (FIG. 8, SEQ ID NOS: 5 and 6).

In yet another embodiment, the soluble CTLA4 mutant molecule is a fusion protein comprising the extracellular domain of CTLA4 having one or more mutations in the S25-R33 and M97-G107 regions. For example, in one embodiment, a CTLA4 mutant molecule comprises tyrosine at position +29 instead of alanine; and glutamic acid at position +104 instead of leucine. A CTLA4 mutant molecule having these substitutions is referred to herein as L104EA29YIg (FIG. 7, SEQ ID NOS: 3 and 4). The nucleic acid molecule that encodes L104EA29YIg is contained in pD16 L104EA29YIg and was deposited on Jun. 19, 2000 with the American Type Culture Collection (ATCC), 10801 University Blvd., Manassas, Va. 20110-2209 (ATCC No. PTA-2104). The pD16 L104EA29YIg vector is a derivative of the pcDNA3 vector (INVITROGEN).

The invention further provides a soluble CTLA4 mutant molecule comprising an extracellular domain of a CTLA4 mutant as shown in FIG. 7(SEQ ID NOS: 3 and 4) or FIG. 8(SEQ ID NOS: 5 and 6) or portion(s) thereof, and a moiety that alters the solubility, affinity and/or valency of the CTLA4 mutant molecule.

In accordance with a practice of the invention, the moiety can be an immunoglobulin constant region or portion thereof, e.g., one or more of a CH1 domain, hinge, CH2 domain or CH3 domain. For in vivo use, it is preferred that the immunoglobulin constant region does not elicit a detrimental immune response in the subject. For example, in clinical protocols, it may be preferred that mutant molecules include human or monkey immunoglobulin constant regions or portion thereof. Examples of suitable immunoglobulin domains include, but are not limited to, IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCδ (IgCdelta) or IgCϵ (IgCepsilon). Other isotypes are possible. Further, other immunoglobulin constant regions or portion thereof are possible (preferably other weakly or non-immunogenic immunoglobulin constant regions or portion thereof ).

For clinical protocols, it is preferred that the immunoglobulin moiety does not elicit a detrimental immune response in a subject. The preferred moiety is the immunoglobulin constant region or portion thereof, including the human or monkey immunoglobulin constant regions or portion thereof. One example of a suitable immunoglobulin region is human Cγ1, including the hinge, CH2 and CH3 regions which can mediate effector functions such as binding to Fc receptors, mediating complement-dependent cytotoxicity (CDC), or mediate antibody-dependent cell-mediated cytotoxicity (ADCC). The immunoglobulin moiety may have one or more mutations therein, (e.g., in the CH2 domain, to reduce effector functions such as CDC or ADCC) where the mutation modulates the binding capability of the immunoglobulin to its ligand, by increasing or decreasing the binding capability of the immunoglobulin to Fc receptors. For example, mutations in the immunoglobulin moiety may include changes in any or all its cysteine residues within the hinge domain, for example, the cysteines at positions +130, +136, and +139 are substituted with serine (FIG. 9, SEQ ID NO: 8). The immunoglobulin moiety may also include the proline at position +148 substituted with a serine, as shown in FIG. 9 (SEQ ID NO: 8). Further, the mutations in the immunoglobulin moiety may include having the leucine at position +144 substituted with phenylalanine, leucine at position +145 substituted with glutamic acid, or glycine at position +147 substituted with alanine. Examples of immunoglobuling moieties include those described and disclosed in U.S. Patent Publications Nos. 2002/0114814 A1 and 2004/0151725 A1, U.S. Pat. Nos. 6,444,792 and 6,750,334, and WO 97/28267.

Other moieties include polypeptide tags. Examples of suitable tags include but are not limited to the p97 molecule, env gp120 molecule, E7 molecule, and ova molecule (Dash, B., et al. (1994) *J. Gen. Virol.* 75:1389-97; Ikeda, T., et al. (1994) *Gene* 138:193-6; Falk, K., et al. (1993) *Cell. Immunol.* 150: 447-52; Fujisaka, K. et al. (1994) *Virology* 204:789-93). Other molecules for use as tags are possible (Gerard, C. et al. (1994) *Neuroscience* 62:721-739; Byrn, R. et al. *J. Virol.* (1989) 63:4370-4375; Smith, D. et al., (1987) *Science* 238: 1704-1707; Lasky, L., (1996) *Science* 233:209-212).

The invention further provides soluble mutant CTLA4Ig fusion proteins preferentially more reactive with the CD80 and/or CD86 antigen compared to wild type CTLA4. One example is L104EA29YIg as shown in FIG. 7 (SEQ ID NOS: 3 and 4).

In another embodiment, the soluble CTLA4 mutant molecule includes a junction amino acid residue, which is located between the CTLA4 portion and the immunoglobulin portion. The junction amino acid can be any amino acid, including glutamine. The junction amino acid can be introduced by molecular or chemical synthesis methods known in the art.

In another embodiment, the soluble CTLA4 mutant molecule includes the immunoglobulin portion (e.g., hinge, CH2 and CH3 domains), where any or all of the cysteine residues, within the hinge domain of the immunoglobulin portion are substituted with serine, for example, the cysteines at positions +130, +136, or +139 (FIG. 7, SEQ ID NOS: 3 and 4; or FIG. 8, SEQ ID NOS: 5 and 6). The mutant molecule may also include the proline at position +148 substituted with a serine, as shown in FIG. 7 (SEQ ID NOS: 3 and 4) or FIG. 8 (SEQ ID NOS: 5 and 6).

The soluble CTLA4 mutant molecule can include a signal peptide sequence linked to the N-terminal end of the extracellular domain of the CTLA4 portion of the mutant molecule. The signal peptide can be any sequence that will permit secretion of the mutant molecule, including the signal peptide from oncostatin M (Malik, et al., (1989) *Molec. Cell. Biol* 9: 2847-2853), or CD5 (Jones, N. H. et al., (1986) *Nature* 323: 346-349), or the signal peptide from any extracellular protein.

The mutant molecule can include the oncostatin M signal peptide linked at the N-terminal end of the extracellular domain of CTLA4, and the human immunoglobulin molecule (e.g., hinge, CH2 and CH3) linked to the C-terminal end of the extracellular domain of CTLA4. This molecule includes the oncostatin M signal peptide encompassing an amino acid sequence having methionine at position −26 through alanine at position −1, the CTLA4 portion encompassing an amino acid sequence having methionine at position +1 through aspartic acid at position +124, a junction amino acid residue glutamine at position +125, and the immunoglobulin portion encompassing an amino acid sequence having glutamic acid at position +126 through lysine at position +357 or glycine at position +356.

The soluble CTLA4 mutant molecules of the invention can be obtained by molecular or chemical synthesis methods. The molecular methods may include the following steps: introducing a suitable host cell with a nucleic acid molecule that expresses and encodes the soluble CTLA4 mutant molecule; culturing the host cell so introduced under conditions that permit the host cell to express the mutant molecules; and isolating the expressed mutant molecules. The signal peptide portion of the mutant molecule permits the protein molecules to be expressed on the cell surface and to be secreted by the host cell. The translated mutant molecules can undergo post-translational modification, involving cleavage of the signal peptide to produce a mature protein having the CTLA4 and the immunoglobulin portions. The cleavage may occur after the alanine at position −1, resulting in a mature mutant molecule having methionine at position +1 as the first amino acid (FIG. 7, SEQ ID NOS: 3 and 4; or FIG. 8, SEQ ID NOS: 5 and 6). Alternatively, the cleavage may occur after the methionine at position −2, resulting in a mature mutant molecule having alanine at position −1 as the first amino acid.

One skilled in the art would be aware that expression of L104EA29YIg in mammalian cells can result in the production of N- and C-terminal variants, such that the proteins produced can have the amino acid sequence of residues: (i) +1 to +357, (ii) −1 to +357; (iii) +1 to +356 or (iv) −1 to 356 (FIG. 7, SEQ ID NOS: 3 and 4; or FIG. 8, SEQ ID NOS: 5 and 6).

A preferred embodiment is a soluble CTLA4 mutant molecule having the extracellular domain of human CTLA4 linked to all or a portion of a human immunoglobulin molecule (e.g., hinge, CH2 and CH3). This preferred molecule includes the CTLA4 portion of the soluble molecule encompassing an amino acid sequence having methionine at position +1 through aspartic acid at position +124, a junction amino acid residue glutamine at position +125, and the immunoglobulin portion encompassing glutamic acid at position +126 through lysine at position +357 or glycine at position +356. The portion having the extracellular domain of CTLA4 is mutated so that alanine at position +29 is substituted with tyrosine and leucine at position +104 is substituted with glutamic acid. The immunoglobulin portion of the mutant molecule can be mutated, so that the cysteines at positions +130, +136, and +139 are substituted with serine, and the proline at position +148 is substituted with serine. This mutant molecule is designated herein as L104EA29YIg (FIG. 7, SEQ ID NOS: 3 and 4).

Another embodiment of L104EA29YIg is a mutant molecule having an amino acid sequence having alanine at position −1 through aspartic acid at position +124, a junction amino acid residue glutamine at position +125, and the immunoglobulin portion encompassing glutamic acid at position +126 (e.g., +126 through lysine at position +357 or glycine at position +356). The portion having the extracellular domain of CTLA4 is mutated so that alanine at position +29 is replaced with tyrosine; and leucine at position +104 is replaced with glutamic acid. The immunoglobulin portion of the mutant molecule is mutated so that the cysteines at positions +130, +136, and +139 are replaced with serine, and the proline at position +148 is replaced with serine. This mutant molecule is designated herein as L104EA29YIg (FIG. 7, SEQ ID NOS: 3 and 4). After the signal sequence has been cleaved, L104EA29YIg can either begin with a methionine at position +1, or begin with alanine at position −1.

Another mutant molecule of the invention is a soluble CTLA4 mutant molecule having the extracellular domain of human CTLA4 linked to the human immunoglobulin molecule (e.g., hinge, CH2 and CH3). This molecule includes the portion of the amino acid sequence encoding CTLA4 starting with methionine at position +1 through aspartic acid at position +124, a junction amino acid residue glutamine at position +125, and the immunoglobulin portion encompassing an amino acid sequence having glutamic acid at position +126 through lysine at position +357 or glycine at position +356. The portion having the extracellular domain of CTLA4 is mutated so that leucine at position +104 is substituted with glutamic acid. The hinge portion of the mutant molecule is mutated so that the cysteines at positions +130, +136, and +139 are substituted with serine, and the proline at position +148 is substituted with serine. This mutant molecule is designated herein as L104EIg (FIG. 8, SEQ ID NOS: 5 and 6).

Alternatively, an embodiment of L104EIg is a soluble CTLA4 mutant molecule having an extracellular domain of human CTLA4 linked to a human immunoglobulin molecule (e.g., hinge, CH2 and CH3). This preferred molecule includes the CTLA4 portion encompassing an amino acid sequence beginning with alanine at position −1 through aspartic acid at position +124, a junction amino acid residue glutamine at position +125, and the immunoglobulin portion encompassing glutamic acid at position +126 through lysine at position +357 or glycine at position +356. The portion having the extracellular domain of CTLA4 is mutated so that leucine at position +104 is substituted with glutamic acid. The hinge portion of the mutant molecule is mutated so that the cysteines at positions +130, +136, and +139 are substituted with serine, and the proline at position +148 is substituted with serine. This mutant molecule is designated herein as L104EIg (FIG. 8, SEQ ID NOS: 5 and 6).

Further, the invention provides a soluble CTLA4 mutant molecule having: (a) a first amino acid sequence of a membrane glycoprotein, e.g., CD28, CD86, CD80, CD40, and gp39, which blocks T cell proliferation, fused to a second amino acid sequence; (b) the second amino acid sequence being a fragment of the extracellular domain of mutant CTLA4 which blocks T cell proliferation, such as, for example an amino acid molecule comprising methionine at position +1 through aspartic acid at position +124 (FIG. 7, SEQ ID NOS: 3 and 4; or FIG. 8, SEQ ID NOS: 5 and 6); and (c) a third amino acid sequence which acts as an identification tag or enhances solubility of the molecule. For example, the third amino acid sequence can consist essentially of amino acid residues of the hinge, CH2 and CH3 regions of a non-immunogenic immunoglobulin molecule. Examples of suitable immunoglobulin molecules include, but are not limited to, human or monkey immunoglobulin, e.g., IgCγ1. Other isotypes are also possible.

The present invention also provides a method for treating an immune disorder associated with graft transplantation by administering to a subject an effective dose of a CTLA4 mutant molecule with an extracellular domain of CTLA4 as shown in SEQ ID NO:8 beginning with alanine at position 26 or methionine at position 27 and ending with aspartic acid at position 150, or a portion thereof. Additionally, in the extracellular domain or portion thereof an alanine at position 55 is substituted with a tyrosine, and a leucine at position 130 is substituted with a glutamic acid. Further the administration regimen comprises an early phase regimen, wherein the early phase regimen may range from the first 3 to 6 months post-transplantation and involves administration that initially is more frequent than monthly.

Additionally, the present invention provides a method for treating an immune disorder associated with graft transplantation by administering to a subject an effective dose of a CTLA4 mutant molecule with an amino acid sequence beginning with methionine at position 27 and ending with aspartic acid at position 150 of SEQ ID NO:4, or with an amino acid sequence beginning with alanine at position 26 and ending with aspartic acid at position 150 of SEQ ID NO:4. Further the CTLA4 mutant molecule administration regimen comprises an early phase regimen, wherein the early phase regimen may range from the first 3 to 6 months post-transplantation and involves administration that initially is more frequent than monthly.

The invention further provides nucleic acid molecules comprising nucleotide sequences encoding the amino acid sequences corresponding to the soluble CTLA4 mutant molecules of the invention. In one embodiment, the nucleic acid molecule is a DNA (e.g., cDNA) or a hybrid thereof. Alternatively, the nucleic acid molecules are RNA or a hybrids thereof.

Additionally, the invention provides a vector, which comprises the nucleotide sequences of the invention. A host vector system is also provided. The host vector system comprises the vector of the invention in a suitable host cell. Examples of suitable host cells include, but are not limited to, prokaryotic and eukaryotic cells.

The invention includes pharmaceutical compositions for use in the treatment of immune disorders associated with graft transplantation comprising pharmaceutically effective doses of soluble CTLA4 mutant molecules. In certain embodiments, the immune disorders associated with graft transplantation are mediated by CD28- and/or CTLA4-positive cell interactions with CD80 and/or CD86 positive cells. The soluble CTLA4 mutant molecules are preferably CTLA4 molecules having one or more mutations in the extracellular domain of CTLA4. The pharmaceutical composition can include soluble CTLA4 mutant protein molecules and/or nucleic acid molecules, and/or vectors encoding the molecules. In preferred embodiments, the soluble CTLA4 mutant molecules have the amino acid sequence of the extracellular domain of CTLA4 as shown in either FIGS. 7 (SEQ ID NOS: 3 and 4)or 8 (SEQ ID NOS: 5 and 6), L104EA29Y or L104E, respectively. Even more preferably, the soluble CTLA4 mutant molecule is L104EA29YIg as disclosed herein. The compositions may additionally include other therapeutic agents, including, but not limited to, drug toxins, enzymes, antibodies, or conjugates.

The pharmaceutical compositions also preferably include suitable carriers and adjuvants which include any material which when combined with the molecule of the invention (e.g., a soluble CTLA4 mutant molecule, such as, L104EA29Y or L104E) retains the molecule's activity and is non-reactive with the subject's immune system. Examples of suitable carriers and adjuvants include, but are not limited to, human serum albumin; ion exchangers; alumina; lecithin; buffer substances, such as phosphates; glycine; sorbic acid; potassium sorbate; and salts or electrolytes, such as protamine sulfate. Other examples include any of the standard pharmaceutical carriers such as a phosphate buffered saline solution; water; emulsions, such as oil/water emulsion; and various types of wetting agents. Other carriers may also include sterile solutions; tablets, including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The pharmaceutical compositions of the invention can be administered using conventional modes of administration including, but not limited to, intravenous (i.v.) administration, intraperitoneal (i.p.) administration, intramuscular (i.m.) administration, subcutaneous administration, oral administration, administration as a suppository, or as a topical contact, or the implantation of a slow-release device such as a miniosmotic pump, to the subject.

The pharmaceutical compositions of the invention may be in a variety of dosage forms, which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

A typical pharmaceutical composition of the invention for intravenous (i.v.) administration is listed below.

| Composition of lyophilized L104EA29YIg 100 mg/vial drug product | |
|---|---|
| Component | Amount/Vial (mg)[a] |
| L104EA29YIg | 110[a] |
| Sucrose | 220 |
| Sodium Phosphate Monobasic Monohydrate | 15.18 |
| Sodium Chloride | 2.55 |
| 1N Sodium Hydroxide | Adjust to pH 7.5 |
| 1N Hydrochloric Acid | Adjust to pH 7.5 |

[a]Each vial contains 10% overfill for vial, needle and syringe holdup of the reconstituted solution.

The lyophilized drug product may be constituted with an aqueous carrier. The aqueous carrier of interest herein is one which is pharmaceutically acceptable (safe and non-toxic for administration to a human) and is useful for the preparation of a liquid formulation, after lyophilization. Typically, the lyophilized drug product is constituted to about 25 mg/ml with 10 ml of either Sterile Water for Injection, USP (SWFI) or 0.9% Sodium Chloride Injection, USP. The constituted solution is further diluted to drug product concentrations between 1 and 10 mg/ml with 0.9% Sodium Chloride Injection, USP. The diluted drug product for injection is isotonic and suitable for administration by intravenous infusion.

A surfactant may be added to the formulation in an amount sufficient to reduce or prevent the interaction of the constituted drug product with a siliconized syringe.

The most effective mode of administration and dosage regimen for the compositions of this invention depends upon the severity and course of the disease, the patient's health and response to treatment and the judgment of the treating physician. Accordingly, the dosages (also known as doses) of the compositions should be titrated to the individual patient.

The soluble CTLA4 mutant molecules may be administered to a subject in an amount, at a frequency over a period of a time (e.g., length of time and/or multiple times) sufficient to block endogenous B7 (e.g., CD80 and/or CD86) molecules from binding their respective ligands, in the subject. Blockage of endogenous B7/ligand binding thereby inhibits interactions between B7-positive cells (e.g., CD80- and/or CD86-positive cells) with CD28- and/or CTLA4-positive cells. Dosage of a therapeutic agent is dependant upon many factors including, but not limited to, the type of tissue affected, the type of immune disorder associated with graft transplantation being treated, the severity of the disease, a subject's health, and a subject's response to the treatment with the agents.

Doses of the molecules or the pharmaceutical compositions of the invention are based on body weight, and administration regimens may be dictated by the target serum trough profiles. Typically, target trough serum concentration of CTLA4 mutant molecules of the invention between about 3 µg/mL and about 30 µg/mL over the first 3 to 6 months post-transplant will be sufficient to maintain function of the allograft, preferably between about 5 µg/mL and about 20 µg/mL. Typically, target trough serum concentration of CTLA4 mutant molecules of the invention during the maintenance phase are between about 0.2 µg/mL and about 3 µg/mL, preferably between about 0.25 µg/mL and about 2.5 µg/mL.

The CTLA4 mutant molecules of the invention may be administered in an amount between about 0.1 to about 20.0 mg/kg weight of the patient, typically between about 1.0 to about 15.0 mg/kg. For example, L104EA29Y may be administered at 10 mg/kg weight of the patient during the early phase, high risk period that follows transplantation and decreased to 5 mg/kg weight of the patient for a maintenance dosage.

Administration of the molecules or pharmaceutical compositions of the invention can be performed over various times. Typically, administration regimens include an early phase, in which doses are higher and the frequency of administration is increased during the period of greatest immunologic risk, followed by a maintenance phase. The early phase regimen may range from the first 3 to 6 months post-transplantation and involves administration that initially is more frequent than monthly, preferably as frequently as daily, weekly or every two weeks depending on the immunologic risk and/or target trough serum concentration. The maintenance phase begins when the early phase ends and involves administration that is not more frequent than monthly, and lasts for as long as needed, typically for as long as the patient retains the transplant. As used herein, day 1 is defined as the day of the transplant or the first day of treatment with molecules or pharmaceutical compositions of the invention.

The dosage of CTLA4 mutant molecules of the invention in the early phase is about 8 to about 12 mg/kg weight of the patient, preferably about 10 mg/kg. The dosage of CTLA4 mutant molecules of the invention in the maintenance phase is about 3 to about 7 mg/kg weight of the patient, preferably about 5 mg/kg.

The early phase may range from the first 3 to 6 months post-transplantation. The administration regimen during early phase may vary depending on the status of the recipient and/or graft. For example, a more intensive early phase regimen would administer a higher dose of the molecules or the pharmaceutical compositions of the invention on day 1, day 5, week 2 visit (e.g., day 13-17), then every two weeks for the first 3 months (e.g., on week 4 visit, week 6 visit, week 8 visit, week 10 visit, and week 12 visit), followed by monthly administration through month 6 visit (e.g., on month 4 visit, month 5 visit, and month 6 visit). An example of a typical more intensive early phase regimen is administration of 10 mg/kg weight of the patient of L104EA29YIg at days 1, 5, 15, 29, 43, 57, 71, 85, 113, 141 and 169. A less intensive regimen, for example, would administer the molecules or the pharmaceutical compositions of the invention on day 1, week 2 visit, week 4 visit, then monthly through month 3 visit. An example of a typical less intensive early phase regimen is administration of 10 mg/kg weight of the patient of L104EA29YIg on days 1, 15, 29, 57 and 85.

Typically, an early phase is followed by a maintenance phase where lower doses of the molecules or pharmaceutical compositions of the invention are administered at one to two month intervals for as long as needed, typically for as long as the patient retains the transplant. An example of the maintenance phase for the more intensive regimen described above includes monthly administration of 5 mg/kg weight of the patient of L104EA29YIg starting at month 7 visit. While an example of the maintenance phase for the less intensive regimen above would include monthly administration of 5 mg/kg weight of the patient of L104EA29YIg starting at month 4 visit.

Alternatively, one knowledgeable in the art would be able to modify the administration regimen in response to the patients risk status and/or response to the therapy post transplantation. For example, the early phase of the less intensive regimen described above could be modified by adding administration day 5 to the regimen, thereby increasing the frequency of administration during the period of greatest immunologic risk.

As used herein, "four weeks," "month", "months" or "monthly" refers to a period of 28±5 days. As used herein, "two weeks" refers to a period of 14±3 days.

Flexibility in the administration regimens is required to facilitate administration scheduling in the lives of transplant recipients, while maintaining the target trough profile of the CTLA4 mutant molecules of the invention. Permitted windows for administering the doses may be as follows:

| Visit | Visit window |
| --- | --- |
| Day 1 and day 5 | 96 hours apart ± 6 hours |
| Week 2 | Target date ± 2 days |
| Week 4-Month 6 | Target date ± 3 days |
| from Month 7 thereafter | Target date ± 5 days |

The target date is a result of adding the desired duration to the previous actual visit date. The desired duration for the week 2 visit is 10 days. The desired duration is 14 days for a visit planned for two weeks from the previous visit, e.g., a week 6 visit following a week 4 visit. The desired duration is 28 days for a visit planned for a month or four week from the previous visit, e.g., a month 4 visit following a month 3 visit. The desired duration is 56 days for a visit planned for two months from the previous visit, e.g., a month 8 visit after a month 6 visit. For example, a day 15 actual visit date plus 14 days results in a week 4 target date of day 29. Based on the visit windows above, the administration may occur on day 29±3 days. Should the administration occur on day 26, that day becomes the actual visit date utilized for the calculation of the next target date.

Low risk of acute rejection recipients typically include those who receive transplants from living related donors and well matched recipient/donors. High risk of acute rejection recipients typically include those who receive transplants from marginal donors or re-transplants, have high panel reactive antibodies or are African American.

In addition to the immediate risk of acute transplant rejection, the use of maintenance drugs such as calcineurin inhibitors and steroids over the long term result in toxicities that negatively impact long-term outcomes and patient quality of life. For example, side effects of maintenance drugs include nephrotoxicity (CAN) resulting in declining renal function and/or graft loss, and cardiovascular and metabolic diseases such as hypertension, hyperlipidemia and diabetes which result in cardiovascular disease and death. Additional side effects include hirsuitism, alpecia, gingival hyperplasia, tremor, neurotoxicity and bone loss which result in non-compliance and reduced quality of life. The molecules or pharmaceutical compositions of the invention maybe used to avoid these outcomes, to reduce incidence, development and/or progression of these outcomes when treating immune disorders associated with graft transplantation, or to treat immune disorders associated with graft transplantation in subjects at risk of these outcomes. The molecules or pharmaceutical compositions of the invention maybe used to improve renal function such as measured by GFR.

The administration of the molecules or pharmaceutical compositions of the invention can be via a 30 minute to one or more hour intravenous infusion. Alternatively, single to multiple subcutaneous injections can deliver the required dosage. Typically, a 30 minute intravenous infusion is the administration route utilized during the early phase of treatment while the patient is in the hospital and/or making scheduled visits to the healthcare professional for monitoring. The subcutaneous injection is the typical administration mode utilized during the maintenance phase, thereby allowing the patient to return to their normal schedule by decreasing the visits to a healthcare professional for intravenous infusions.

An alternate embodiment of the invention provides a method for treating an immune disorder associated with graft transplantation in subjects that have received an alternate immunosuppressive therapy post transplantation. The subjects on an alternate pharmaceutical immunosuppressive therapy may change or switch or convert to a therapy including the molecules or pharmaceutical compositions of the present invention, thereby eliminating the alternate drug. Typically the pharmaceutical that is to be eliminated is ramped down over an appropriate period of time, based on the prescribing instructions of that specific drug, while at the same time the molecules or pharmaceutical composition of the instant invention is administered more frequently than monthly. Once the subject is completely off the alternate drug, the subject may return to a standard maintenance regimen utilizing the molecules or pharmaceutical compositions of the instant invention. For example, a subject receiving CsA/MMF±corticosteroid regimen may switch CsA with L104EA29YIg for a L104EA29YIg/MMF±corticosteroid regimen. The conversion administration schedule may include a ramping down of the dose of CsA over two months and the administration of 5 mg/kg of L104EA29YIg every two weeks during those two months. Once the CsA is eliminated, the subject would then enter the maintenance phase and continue to receive 5 mg/kg every 4 or 8 weeks for the duration of the treatment in the absence of CsA.

One embodiment provides appropriate dosages for a soluble CTLA4 mutant molecule disclosed herein that is effective for blocking B7 interactions with its ligand and/or treating an immune system disease. For example the dosage may be based on body weight, and administration regimens may be dictated by the target serum trough profiles. For example, the effective target trough serum concentrations of soluble CTLA4 mutant molecules disclosed herein to treat an immune system disease may be between about 0.2 µg/mL and about 30 µg/mL. Alternatively, the soluble CTLA4 mutant molecules disclosed herein may be administered in an amount between about 0.1 to about 20.0 mg/kg weight of the patient to treat immune system diseases.

The present invention further provides methods for treating immune disorders associated with graft transplantation. In particular embodiments, the immune disorders associated with graft transplantation are mediated by CD28- and/or CTLA4-positive cell interactions with CD80/CD86-positive cells. In a further embodiment, T cell interactions are inhibited. These methods comprise administering to a subject the soluble CTLA4 mutant molecules of the invention to regulate T cell interactions with the CD80- and/or CD86-positive cells. Examples of immune disorders associated with graft transplantation are discussed above.

The present invention further provides a method for prophylaxis of or inhibiting or preventing solid organ, tissue, cell and/or external anatomy transplant rejections by a subject, the subject being a recipient of transplant solid organ, tissue, cell and/or external anatomy. Typically, in transplants, rejection of the graft is initiated through its recognition as foreign by T cells, followed by an immune response that destroys the graft. The soluble CTLA4 mutant molecules of this invention, by inhibiting T lymphocyte proliferation and/or cytokine secretion, may result in reduced tissue destruction and induction of antigen-specific T cell unresponsiveness which may result in long-term graft acceptance.

The study described in Example 3 compared the efficacy and safety of L104EA29YIg as a maintenance immunosuppressant with cyclosporineA (CsA) over 12 months when used as part of a CNI-free combination regimen consisting of basiliximab(Simulect®; Novartis) induction, mycophenolate mofetil (MMF; CellCept®; Roche), and corticosteroids in renal transplant recipients. Objectives included assessment of the incidence of acute rejection (biopsy-confirmed or presumed) at 6 months and 1 year; measured glomerular filtration rate (GFR) via iohexol clearance at 1, 6, and 12 months; parameters of hypertension including serum cholesterol and triglycerides; and overall safety. Other pre-specified analyses included patient death or graft loss at 1 year; the severity of acute rejection; the incidence of post-transplant diabetes mellitus [defined as any therapy required for hyperglycemia for ≧4 weeks, or a hemoglobin AIC (HbAIc) >7%, in patients not previously known to be diabetic]; calculated GFR, using the Modification of Diet in Renal Disease (MDRD, Levey A S, Bosch J P, Lewis J P, Greene T, Rogers N, Roth D. A more accurate method to estimate glomerular filtration rate from serum creatinine: a new prediction equation. Modification of Diet in Renal Disease Study Group. Ann Intern Med 1999; 130:461-470), Jelliffe (R W. Creatinine clearance: Bedside estimate. Ann Inter Med. 1973;79:604-605), Cockcroft-Gault (Cockcroft D W, Gault M H. Prediction of creatinine clearance from serum creatinine. Nephron 1976;16:31-41), and Nankivell (Nankivell B J, Gruenewald S M, Allen R D, Chapman J R. Predicting glomerular filtration rate after kidney transplantation. Transplantation. 1995; 59(12):1683-1689)

formulas; pharmacokinetics and immunogenicity. Diagnosis and treatment of acute rejection (AR) was based on the Banff 97 criteria and grade (Racusen L C, Solez K, Colvin R B, et al. The Banff 97 working classification of renal allograft pathology. Kidney Int 1999;55(2):713-23.). Post hoc analysis was conducted of the incidence of chronic allograft nephropathy (CAN).

This 12-month study demonstrated that L104EA29YIg-based maintenance therapy conferred equivalent efficacy in preventing AR and similar patient and graft survival compared with CsA. In addition, L104EA29YIg demonstrated significant improvements in renal function and reductions in CAN compared with CsA-based maintenance immunosuppression. L104EA29YIg was safe and well tolerated and was not associated with typical CNI-related toxicities.

Improved renal function during the first post-transplant year has been shown to correlate with better long-term outcomes (Hariharan S, McBride M A, Cherikh W S, Tolleris C B, Bresnahan B A, Johnson C P. Post-transplant renal function in the first year predicts long-term kidney transplant survival. Kidney Int 2002;62(1):311-8) since the long-term use of CNIs is limited by their nephrotoxicity (Danovitch G M. Immunosuppressive medications for renal transplantation: a multiple choice question. Kidney Int 2001;59(1):388-402), which leads to reduced graft function and renal insufficiency with all its attendant problems. Thus, perhaps the most notable findings seen with L104EA29YIg treatment are the superior GFRs coupled with the 12-month renal histology showing reductions in development and/or progression of CAN compared with CsA. This was a surprising outcome and the first time that a finding of this sort has been shown in a randomized Phase II trial of an immunosuppressive therapy. Since preservation of the nephron mass, by prevention of immunologic, cardiovascular and/or metabolic insults contributes to beneficial effects on both patient and graft survival it is possible that L104EA29YIg may be associated with better long-term outcomes.

These issues are particularly important with the increasing use of organs from extended criteria donors or recipients since these are particularly susceptible to CNI-related toxicity. Decreasing the incidence of CV and metabolic events in patients who have undergone renal transplant is also central to improving long-term outcomes.

The molecules or pharmaceutical compositions of the invention maybe used to treat immune disorders associated with graft transplantation in subjects who are extended criteria recipients and/or who are receiving grafts from extended criteria donors. These criteria, which are based in part on criteria issued by the United Network of Organ Sharing (UNOS), may include one or more of the following: donor age less than 10 or greater than or equal to 60 years; donor after cardiac death; anticipated cold-ischemic time of donor organ greater than or equal to 24 hours; subjects undergoing first time transplant with a current PRA≧50%, or undergoing retransplantation with PRA≧30%; subjects with previous graft loss due to acute rejection during the first 6 months after transplant; subjects with positive T-cell lymphocytotoxic crossmatch using donor lymphocytes and recipient serum; subjects with HIV infection; subjects with active tuberculosis requiring treatment within the previous 3 years; or other criteria issued by the United Network of Organ Sharing (UNOS). An example of possible extended criteria for a donor and/or the donor kidney includes at least 1 of the following extended criteria for organ donation a) Donor age ≧60 years OR b) Donor age 50-59 years and 1 of the following: (i) Cerebrovascular accident (CVA)+hypertension+ SCr>1.5 mg/dL OR (ii) CVA+hypertension OR (iii)CVA+ SCr>1.5 mg/dL OR (iv) Hypertension+SCr>1.5 mg/dL OR c) CIT≧24 hours, donor age>10 years OR d) Donor with cardiac death (non-heart beating donor).

The present invention also provides methods for inhibiting graft versus host disease in a subject. This method comprises administering to the subject a soluble CTLA4 mutant molecule of the invention, alone or together, concomitantly or sequentially, with further additional ligands, reactive with IL-2, IL-2R, IL-4, or γ-interferon. For example, a soluble CTLA mutant molecule of this invention may be administered to a bone marrow transplant recipient to inhibit the alloreactivity of donor T cells. Alternatively, donor T cells within a bone marrow graft may be tolerized to a recipient's alloantigens ex vivo prior to transplantation.

The soluble CTLA4 mutant molecules of the invention, for example L104EA29Y, may be administered as the sole active ingredient or together, concomitantly or sequentially, with one or more other drugs in immunomodulating regimens, immunosuppressive agents and/or other anti-inflammatory agents e.g., for the treatment, prevention or inhibition or prophylaxis of allograft or xenograft acute or chronic rejection or to induce tolerance. For example, it may be used in combination with a calcineurin inhibitor (e.g., cyclosporin A or FK506); an immunosuppressive macrolide (e.g., tacrolimus, rapamycin, sirolimus) or a derivative thereof (e.g., 40-O-(2-hydroxy)ethyl-rapamycin, sirolimus, centican); a lymphocyte homing agent (e.g., FTY720) or an analog thereof (FK778, Jak-3), corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies (e.g., basiliximab, daclizumab), ligands, monoclonal antibodies or antibody fragments thereof to leukocyte receptors(e.g., MHC, CD2, CD3, CD4, CD 11a/CD18, CD7, CD25, CD 27, B7, CD40, CD45, CD58, CD 137, ICOS, CD150 (SLAM), OX40, 4-1BBor their ligands); or other immunomodulatory compounds(e.g., CTLA4/CD28-Ig), or other adhesion molecule inhibitors (e.g., mAbs) or low molecular weight inhibitors including LFA-1 antagonists, Selectin antagonists and VLA-4 antagonists. The compound is particularly useful in combination with a compound which interferes with CD40 and its ligand (e.g., antibodies to CD40 and antibodies to CD40-L), such as Chi220 (U.S. Pat. No. 6,051,228) e.g., in the above described indications, e.g the induction of tolerance.

Where the soluble CTLA4 mutant molecules of the invention are administered concomitantly or sequentially in conjunction with other immunosuppressive/immunomodulatory therapy, e.g as herein specified, dosages of the co-administered immunosuppressant, or immunomodulatory compound will of course vary depending on the type of co-drug employed, e.g., whether it is a steroid or a cyclosporine, on the specific drug employed, on the condition being treated and so forth.

In accordance with the foregoing, the present invention further provides therapeutic combinations, e.g., a kit, e.g., for use in any method as defined above, comprising a L104EA29YIg, in free form or in pharmaceutically acceptable salt form, to be used concomitantly or in sequence with at least one pharmaceutical composition comprising an immunosuppressant, immunomodulatory or anti-inflammatory drug. The kit may comprise instructions for its administration.

In accordance with the foregoing the present invention provides in a yet further aspect methods as defined above comprising co-administration, e.g., concomitantly or in sequence, of a therapeutically effective dose of soluble CTLA4 mutant molecule of the invention, with immunosuppressive agents. Immunosuppressive agents include soluble gp39 (also known as CD40 ligand (CD40L), CD154, T-BAM, TRAP), soluble CD29, soluble CD40, soluble CD80 (e.g., ATCC 68627), soluble CD86, soluble CD28 (e.g., 68628), soluble CD56, soluble Thy-1, soluble CD3, soluble TCR, soluble VLA-4, soluble VCAM-1, soluble LECAM-1, soluble ELAM-1, soluble CD44, ligands, antibodies or antibody fragments reactive with gp39 (e.g., ATCC HB-10916, ATCC HB-12055 and ATCC HB-12056), ligands, antibodies or antibody fragments reactive with CD40 (e.g., ATCC HB-9110), ligands, antibodies or antibody fragments reactive with B7 (e.g., ATCC HB-253, ATCC CRL-2223, ATCC CRL-2226, ATCC HB-301, ATCC HB-11341, etc), ligands, antibodies or antibody fragments reactive with CD28 (e.g., ATCC HB-11944 or mAb 9.3 as described by Martin et al (J. Clin. Immun. 4(1):18-22, 1980), ligands, antibodies or antibody fragments reactive with LFA-1 (e.g., ATCC HB-9579 and ATCC TIB-213), ligands, antibodies or antibody fragments reactive with LFA-2, ligands, antibodies or antibody fragments reactive with IL-2 or IL-2R, ligands, antibodies or antibody fragments reactive with IL-12, ligands, antibodies or antibody fragments reactive with IFN-gamma, ligands, antibodies or antibody fragments reactive with CD2, antibodies ligands, antibodies or antibody fragments reactive with CD48, ligands, antibodies or antibody fragments reactive with any ICAM (e.g., ICAM-1 (ATCC CRL-2252), ICAM-2 and ICAM-3), ligands, antibodies or antibody fragments reactive with CTLA4 (e.g., ATCC HB-304), ligands, antibodies or antibody fragments reactive with Thy-1, ligands, antibodies or antibody fragments reactive with CD56, ligands, antibodies or antibody fragments reactive with CD3, ligands, antibodies or antibody fragments reactive with CD29, ligands, antibodies or antibody fragments reactive with TCR, ligands, antibodies or antibody fragments reactive with VLA-4, ligands, antibodies or antibody fragments reactive with VCAM-1, ligands, antibodies or antibody fragments reactive with LECAM-1, ligands, antibodies or antibody fragments reactive with ELAM-1, ligands, antibodies or antibody fragments reactive with CD44. In certain embodiments, monoclonal antibodies are preferred. In other embodiments, antibody fragments are preferred. Antibody fragments include but are not limited to Fab, Fab', F(ab')$_2$, Fv, scFv and domain antibodies (dabs) including but not limited to those described in WO2006/030220. As persons skilled in the art will readily understand, the combination can include the soluble CTLA4 mutant molecules of the invention and one other immunosuppressive agent, the soluble CTLA4 mutant molecules with two other immunosuppressive agents, the soluble CTLA4 molecules with three other immunosuppressive agents, etc. The determination of the optimal combination and dosages can be determined and optimized using methods well known in the art.

A particularly useful combination is L104EA29YIg or pharmaceutical composition thereof with a compound that interferes with IL-2 and its ligand, specifically an antagonist targeted against IL-2R (alpha) which is selectively expressed on the surface of activated T-lymphocytes. A compound that binds to IL-2R(alpha) competitively inhibits IL-2 mediated activation of lymphocytes, which is a critical pathway in the cellular immune response involved in allograft rejection.

Some specific combinations include the following: L104EA29YIg and CD80 monoclonal antibodies (mAbs); L104EA29YIg and CD86 mabs; L104EA29YIg, CD80 mAbs, and CD86 mAbs; L104EA29YIg and gp39 mAbs; L104EA29YIg and CD40 mAbs; L104EA29YIg and CD28 mAbs; L104EA29YIg, CD80 and CD86 mAbs, and gp39 mAbs; L104EA29YIg, CD80 and CD86 mAbs and CD40 mAbs; and L104EA29YIg, anti-LFA1 mAb, and anti-gp39 mAb. A specific example of a gp39 mAb is MR1. Other combinations will be readily appreciated and understood by persons skilled in the art.

In accordance with the foregoing the present invention provides in a yet further aspect methods as defined above comprising co-administration, e.g., concomitantly or in sequence, of a therapeutically effective dose of soluble CTLA4 mutant molecule of the invention, with an adjunctive agent and/or a corticosteroid. The goal is to replace the toxic calcineurin inhibitors with the CTLA4 mutant molecules of the invention. However, the CTLA4 mutant molecules of the invention also may be co-administered concomitantly or sequentially with CNIs such as cyclosporine (Neoral®, Sandimmune® from Novartis) and tacrolimus (FK506, Prograf® from Fujisawa).

Examples of adjunctive agents include but are not limited to inhibitors of inosine monophosphate dehydrogenase (IMPDH), e.g., mycophenolate mofetil (MMF, Cellcept® from Roche Laboratories) and mycophenolic acid (Myfortic® from Novartis); rapamycin (sirolimus, Rapamune® from Wyeth/Ayerst); azathioprine (Azarsan® from Salix, Imurane, generic); a lymphocyte homing agent, e.g., FTY720(from Novartis); FK778(from Fujisawa); Jak-3 (from Pfizer); and Certican® (everolimus from Novartis).

Examples of corticosteroids include but are not limited to, betamethasone, budesonide, cortisol, cortisone, dexamethasone, hydrocritisone, methylprednisolone, prednisolone, prednisone and triamcinolone.

Typical co-administration combinations include but are not limited to L104EA29YIg and at least one adjunctive agent selected from the group listed above; L104EA29YIg and at least one corticosteroid selected from the group listed above; L104EA29YIg, MMF(Cellcept from Roche) and a corticosteroid selected from the group listed above; L104EA29YIg, rapamycin (sirolimus, Rapamune® from Wyeth/Ayerst) with or without a corticosteroid selected from the group listed above.

The co-administration combinations described above may be utilized with an induction agent such as immunosuppressive monoclonal antibodies, e.g., basiliximab (Simulect® from Novartis), muromonab (Orthoclone OKT3® from Ortho Biotech), rituximab (Rituxan® from Genentech) and daclizumab (Zenapax® from Roche Labs); or anti-thymocyte globulin (Thymoglobulin® from SangStat). For example, suitable combinations include but are not limited to basiliximab (Simulect® from Novartis) with L104EA29YIg, MMF (Cellcept from Roche) and prednisolone; or daclizumab (Zenapax® from Roche), L104EA29YIg and rapamycin (sirolimus, Rapamune® from Wyeth/Ayerst).

Typically, the standard dosages and administration regimen of the co-administered drugs described above are not influenced by the addition of the CTLA4 mutant molecules of the invention to the treatment regimen. However, one knowledgeable in the art may prescribe lower doses of the co-administered drugs, e.g., adjunctive agents and/or corticosteroids, due to the incorporation of the less toxic CTLA4 mutant molecules of the invention into the treatment regimen.

Prescribing information may be based on the package insert for each co-administered drug. A corticosteroid may be co-administered with the molecules or pharmaceutical composition of the invention. For example, subjects may be treated daily with corticosteroids. One steroid maintenance and taper strategy may include 500 mg i.v. methylprednisolone on arrival in the operating room (OR) 250 mg i.v. methylprednisolone on day 2, followed by prednisone (or prednisolone) 100 mg orally on day 3, followed by a taper of prednisone (or prednisolone) to 20-30 mg/day by the end of week 2, followed by a taper of prednisone (or prednisolone) to no lower than 2.5 mg/day through month 6. Subjects may remain on at least 2.5 mg/day throughout the course of their treatment.

Additional co-administered drugs may include mycophenolate mofetil (MMF). Typically MMF is administered in 2 divided doses on a consistent schedule in relation to time of day and meals. An example of an administration regimen for MMF includes 2 g daily. The first dose can be administered preoperatively. Subsequent doses may be administered p.o. as soon as the subject is able to tolerate medications by mouth. The dose and schedule may be adjusted on the basis of laboratory values (e.g., decreased WBCs) and subject tolerability. The package insert provides full prescribing information.

Another co-administered drug may include basiliximab. Reconstituted basiliximab (20 mg in 5 mL) may be diluted to a volume of 50 mL with normal saline or dextrose 5% and administered as an i.v. infusion over 20-30 minutes. The first 20 mg dose may be administered on Day 1 (the day of transplantation). The second 20 mg dose may be given on Day 5. The package insert provides full prescribing information Further provided are therapeutic combinations, e.g., a kit, e.g., for use in any method as defined above, comprising a L104EA29YIg, in free form or in pharmaceutically acceptable salt form, to be used concomitantly or in sequence with at least one pharmaceutical composition comprising an adjunctive agent and corticosteroids. The kit may comprise instructions for its administration.

The label and/or the instructions may indicate that the pharmaceutical composition can be used alone, or in combination, concomitantly or sequentially with a second agent to treat a condition of choice e.g., immune system diseases, autoimmune diseases, immunoproliferative diseases, immune disorders associated with graft transplantation as described above.

The label may indicate appropriate dosages for the molecules disclosed herein. For example, the label can indicate that dosages for a molecule that is effective for blocking B7 interactions with its ligand and/or treating an immune system disease may be based on body weight, and administration regimens may be dictated by the target serum trough profiles. For example, the label may indicate that the effective target trough serum concentrations of CTLA4 mutant molecules disclosed herein to treat an immune system disease may be between about 0.2 µg/mL and about 30 µg/mL. Alternatively, the label may indicate that the CTLA4 mutant molecules disclosed herein may be administered in an amount between about 0.1 to about 20.0 mg/kg weight of the patient to treat immune system diseases.

Methods for Producing the Molecules of the Invention

Expression of CTLA4 mutant molecules can be in prokaryotic cells. Prokaryotes most frequently are represented by various strains of bacteria. The bacteria may be a gram positive or a gram negative. Typically, gram-negative bacteria such as *E. coli* are preferred. Other microbial strains may also be used.

Sequences encoding CTLA4 mutant molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived PL promoter and N-gene ribosome binding site (Shimatake, et al., (1981) *Nature* 292:128).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to CaCl$_2$-shock (Cohen, (1972) *Proc. Natl. Acad. Sci. USA* 69:2110, and Sambrook et al. (eds.), "*Molecular Cloning: A Laboratory Manual*", 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Particular CHO cells include, but are not limited to, DG44 (Chasin, et la., 1986 *Som. Cell. Molec. Genet.* 12:555-556; Kolkekar 1997 *Biochemistry* 36:10901-10909), CHO-K1 (ATCC No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Exemplary plant cells include tobacco (whole plants, cell culture, or callus), corn, soybean, and rice cells. Corn, soybean, and rice seeds are also acceptable.

Nucleic acid sequences encoding the CTLA4 mutant molecules can also be inserted into a vector designed for expressing foreign sequences in a eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers, et al., (1973) *Nature* 273:113), or other viral promoters such as those derived from polyoma, Adenovirus 2, and bovine papilloma virus. An inducible promoter, such as hMTII (Karin, et al., (1982) *Nature* 299:797-802) may also be used.

Vectors for expressing CTLA4 mutant molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pCDNA-3 (Invitrogen) or modified forms thereof, adenoviral vectors; Adeno-associated virus vectors, baculovirus vectors, yeast vectors (e.g., pESC vectors (Stratagene)).

Nucleic acid sequences encoding CTLA4 mutant molecules can integrate into the genome of the eukaryotic host cell and replicate as the host genome replicates. Alternatively, the vector carrying CTLA4 mutant molecules can contain origins of replication allowing for extrachromosomal replication.

For expressing the nucleic acid sequences in *Saccharomyces cerevisiae*, the origin of replication from the endogenous yeast plasmid, the 2μ circle can be used. (Broach, (1983) *Meth. Enz.* 101:307). Alternatively, sequences from the yeast genome capable of promoting autonomous replication can be used (see, for example, Stinchcomb et al., (1979) *Nature* 282:39); Tschemper et al., (1980) *Gene* 10:157; and Clarke et al., (1983) *Meth. Enz.* 101:300).

Transcriptional control sequences for yeast vectors include promoters for the synthesis of glycolytic enzymes (Hess et al., (1968) *J. Adv. Enzyme Reg.* 7:149; Holland et al., (1978) *Biochemistry* 17:4900). Additional promoters known in the art include the CMV promoter provided in the CDM8 vector (Toyama and Okayama, (1990) *FEBS* 268:217-221); the promoter for 3-phosphoglycerate kinase (Hitzeman et al., (1980) *J. Biol. Chem.* 255:2073), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include, but are not limited to, Agrobacterium $T_i$ plasmids, cauliflower mosaic virus (CaMV), and tomato golden mosaic virus (TGMV).

General aspects of mammalian cell host system transformations have been described by Axel (U.S. Pat. No. 4,399,216 issued Aug. 16, 1983). Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

Expression of CTLA4 mutant molecules can be detected by methods known in the art. For example, the mutant molecules can be detected by Coomassie staining SDS-PAGE gels and immunoblotting using antibodies that bind CTLA4. Protein recovery can be performed using standard protein purification means, e.g., affinity chromatography or ion-exchange chromatography, to yield substantially pure product (R. Scopes in: "*Protein Purification, Principles and Practice*", Third Edition, Springer-Verlag (1994)).

US patent application US Publication Number 2005/0019859, 2005/0084933 and WO 04/058944 teach a processes for the production of proteins of the invention, specifically recombinant glycoprotein products, by animal or mammalian cell cultures and are herein incorporated by reference.

The invention further provides soluble CTLA4 mutant molecules produced above herein.

CTLA4IG Codon-Based Mutagenesis

In one embodiment, site-directed mutagenesis and a novel screening procedure were used to identify several mutations in the extracellular domain of CTLA4 that improve binding avidity for CD86. In this embodiment, mutations were carried out in residues in the regions of the extracellular domain of CTLA4 from serine 25 to arginine 33, the C' strand (alanine 49 and threonine 51), the F strand (lysine 93, glutamic acid 95 and leucine 96), and in the region from methionine 97 through tyrosine 102, tyrosine 103 through glycine 107 and in the G strand at positions glutamine 111, tyrosine 113 and isoleucine 115. These sites were chosen based on studies of chimeric CD28/CTLA4 fusion proteins (Peach et al., *J. Exp. Med.,* 1994, 180:2049-2058), and on a model predicting which amino acid residue side chains would be solvent exposed, and a lack of amino acid residue identity or homology at certain positions between CD28 and CTLA4. Also, any residue which is spatially in close proximity (5 to 20 Angstrom Units) to the identified residues is considered part of the present invention.

To synthesize and screen soluble CTLA4 mutant molecules with altered affinities for CD80 and/or CD86, a two-step strategy was adopted. The experiments entailed first generating a library of mutations at a specific codon of an extracellular portion of CTLA4 and then screening these by BIAcore analysis to identify mutants with altered reactivity to CD80 or CD86. The Biacore assay system (Pharmacia, Piscataway, N.J.) uses a surface plasmon resonance detector system that essentially involves covalent binding of either CD80Ig or CD86Ig to a dextran-coated sensor chip which is located in a detector. The test molecule can then be injected into the chamber containing the sensor chip and the amount of complementary protein that binds can be assessed based on the change in molecular mass which is physically associated with the dextran-coated side of the sensor chip; the change in molecular mass can be measured by the detector system.

Advantages of the Invention

Because CTLA4 binding to CD80 and CD86 is characterized by rapid "on" rates and rapid dissociation ("off") rates, and because CTLA4Ig-CD86 complexes dissociate approximately 5- to 8-fold more rapidly than CTLA4Ig-CD80 complexes, it was reasoned that slowing the rate of dissociation of CTLA4Ig from CD80 and/or CD86 would result in molecules with more potent immunosuppressive properties. Thus, soluble CTLA4 mutant molecules having a higher avidity for CD80- or CD86-positive cells compared to wild type CTLA4, or non-mutated forms of CTLA4Ig, are expected to block the priming of antigen specific activated cells with higher efficiency than wild type CTLA4 or non-mutated forms of CTLA4Ig.

EXAMPLES

The following examples are presented to illustrate the present invention and to assist one of ordinary skill in making and using the same. The examples are not intended in any way to otherwise limit the scope of the invention.

Example 1

This example provides a description of the methods used to generate the nucleotide sequences encoding the soluble CTLA4 mutant molecules of the invention. A single-site mutant L104EIg was generated and tested for binding kinetics for CD80 and/or CD86. The L104EIg nucleotide sequence was used as a template to generate the double-site mutant CTLA4 sequence, L104EA29YIg, which was tested for binding kinetics for CD80 and/or CD86.

CTLA4Ig Codon Based Mutagenesis

A mutagenesis and screening strategy was developed to identify mutant CTLA4Ig molecules that had slower rates of dissociation ("off" rates) from CD80 and/or CD86 molecules. Single-site mutant nucleotide sequences were generated using CTLA4Ig (U.S. Pat. Nos. 5,844,095; 5,851,795; and 5,885,796; ATCC Accession No. 68629) as a template. Mutagenic oligonucleotide PCR primers were designed for random mutagenesis of a specific cDNA codon by allowing any base at positions 1 and 2 of the codon, but only guanine or thymine at position 3 (XXG/T; also known as NNG/T). In this manner, a specific codon encoding an amino acid could be randomly mutated to code for each of the 20 amino acids. In that regard, XXG/T mutagenesis yields 32 potential codons encoding each of the 20 amino acids. PCR products encoding mutations in close proximity to -M97-G107 of CTLA4Ig (see FIG. 7, SEQ ID NOS: 3 and 4; or FIG. 8, SEQ ID NOS: 5 and 6), were digested with SacI/XbaI and subcloned into similarly cut CTLA4Ig nLN (also known as piLN) expression vector. This method was used to generate the single-site CTLA4 mutant molecule L104EIg (FIG. 8, SEQ ID NOS: 5 and 6).

Figure 12:
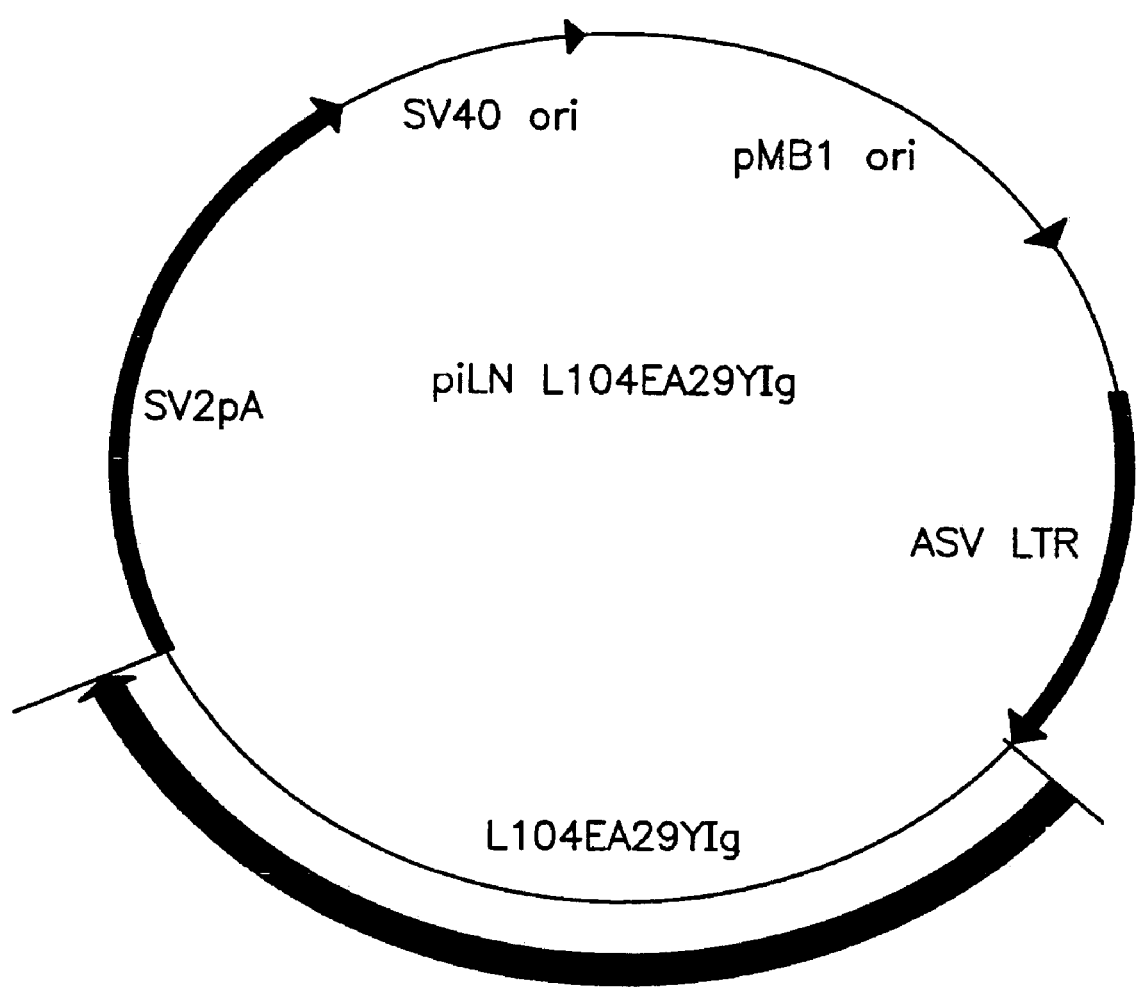
FIG. 12 depicts a schematic diagram of a vector, piLN-L104EA29Y, having the L104EA29YIg insert.

For mutagenesis in proximity to S25-R33 of CTLA4Ig, a silent NheI restriction site was first introduced 5' to this loop, by PCR primer-directed mutagenesis. PCR products were digested with NheI/XbaI and subcloned into similarly cut CTLA4Ig or L104EIg expression vectors. This method was used to generate the double-site CTLA4 mutant molecule L104EA29YIg (FIG. 7, SEQ ID NOS: 3 and 4). In particular, the nucleic acid molecule encoding the single-site CTLA4 mutant molecule, L104EIg, was used as a template to generate the double-site CTLA4 mutant molecule, L104EA29YIg. The piLN vector having the L104EA29YIg is shown in FIG. 12.

Example 2

The following provides a description of the screening methods used to identify the single- and double-site mutant CTLA4 polypeptides, expressed from the constructs described in Example 1, that exhibited a higher binding avidity for CD80 and CD86 antigens, compared to non-mutated CTLA4Ig molecules.

Current in vitro and in vivo studies indicate that CTLA4Ig by itself is unable to completely block the priming of antigen specific activated T cells. In vitro studies with CTLA4Ig and either monoclonal antibody specific for CD80 or CD86 measuring inhibition of T cell proliferation indicate that anti-CD80 monoclonal antibody did not augment CTLA4Ig inhibition. However, anti-CD86 monoclonal antibody did augment the inhibition, indicating that CTLA4Ig was not as effective at blocking CD86 interactions. These data support earlier findings by Linsley et al. (*Immunity*, (1994), 1:793-801) showing inhibition of CD80-mediated cellular responses required approximately 100 fold lower CTLA4Ig concentrations than for CD86-mediated responses. Based on these findings, it was surmised that soluble CTLA4 mutant molecules having a higher avidity for CD86 than wild type CTLA4 should be better able to block the priming of antigen specific activated cells than CTLA4Ig.

To this end, the soluble CTLA4 mutant molecules described in Example 1 above were screened using a novel screening procedure to identify several mutations in the extracellular domain of CTLA4 that improve binding avidity for CD80 and CD86. This screening strategy provided an effective method to directly identify mutants with apparently slower "off" rates without the need for protein purification or quantitation since "off" rate determination is concentration independent (O'Shannessy et al., (1993) *Anal. Biochem.*, 212:457-468).

COS cells were transfected with individual miniprep purified plasmid DNA and propagated for several days. Three day conditioned culture media was applied to BIAcore biosensor chips (Pharmacia Biotech AB, Uppsala, Sweden) coated with soluble CD80Ig or CD86Ig. The specific binding and dissociation of mutant proteins was measured by surface plasmon resonance (O'Shannessy, D. J., et al., (1993) *Anal. Biochem.* 212:457-468). All experiments were run on BIAcore™ or BIAcore™ 2000 biosensors at 25° C. Ligands were immobilized on research grade NCM5 sensor chips (Pharmacia) using standard N-ethyl-N'-(dimethylaminopropyl)carbodiimidN-hydroxysuccinimide coupling (Johnson, B., et al. (1991) *Anal. Biochem.* 198: 268-277; Khilko, S. N., et al. (1993) *J. Biol. Chem.* 268:5425-15434).

Screening Method

COS cells grown in 24 well tissue culture plates were transiently transfected with DNA encoding mutant CTLA4Ig. Culture media containing secreted soluble mutant CTLA4Ig was collected 3 days later.

Conditioned COS cell culture media was allowed to flow over BIAcore biosensor chips derivatized with CD86Ig or CD80Ig (as described in Greene et al., 1996 *J. Biol. Chem.* 271:26762-26771), and mutant molecules were identified with "off" rates slower than that observed for wild type CTLA4Ig. The cDNAs corresponding to selected media samples were sequenced and DNA was prepared to perform larger scale COS cell transient transfection, from which mutant CTLA4Ig protein was prepared following protein A purification of culture media.

BIAcore analysis conditions and equilibrium binding data analysis were performed as described in J. Greene et al. 1996 *J. Biol. Chem.* 271:26762-26771, and as described herein.

BIAcore Data Analysis

Senosorgram baselines were normalized to zero response units (RU) prior to analysis. Samples were run over mock-derivatized flow cells to determine background response unit (RU) values due to bulk refractive index differences between solutions. Equilibrium dissociation constants ($K_d$) were calculated from plots of $R_{eq}$ versus C, where $R_{eq}$ is the steady-state response minus the response on a mock-derivatized chip, and C is the molar concentration of analyte. Binding curves were analyzed using commercial nonlinear curve-fitting software (Prism, GraphPAD Software).

Experimental data were first fit to a model for a single ligand binding to a single receptor (1-site model, i.e., a simple langmuir system, $A+B \leftrightarrows AB$), and equilibrium association constants ($K_a=[A]\cdot[B]\backslash[AB]$) were calculated from the equation $R=R_{max} \cdot C/(K_d+C)$. Subsequently, data were fit to the simplest two-site model of ligand binding (i.e., to a receptor having two non-interacting independent binding sites as described by the equation $R=R_{max1} \cdot C\backslash(K_{d1}+C)+R_{max2} \cdot C\backslash(K_{d2}+C)$).

The goodness-of-fits of these two models were analyzed visually by comparison with experimental data and statistically by an F test of the sums-of-squares. The simpler one-site model was chosen as the best fit, unless the two-site model fit significantly better ($p<0.1$).

Association and disassociation analyses were performed using BIA evaluation 2.1 Software (Pharmacia). Association rate constants $k_{on}$ were calculated in two ways, assuming both homogenous single-site interactions and parallel two-site interactions. For single-site interactions, $k_{on}$ values were calculated according to the equation $R_t=R_{eq}(1-\exp^{-ks(t-t_0)})$, where $R_t$ is a response at a given time, t; $R_{eq}$ is the steady-state response; $t_0$ is the time at the start of the injection; and $k_s=dR/dt=k_{on} \cdot Ck_{off}$, and where C is a concentration of analyte, calculated in terms of monomeric binding sites. For two-site interactions $k_{on}$ values were calculated according to the equation $R_t=R_{eq1}(1-\exp^{-ks1(t-t_0)})+R_{eq2}(1-\exp^{ks2(t-t_0)})$. For each model, the values of $k_{on}$ were determined from the calculated slope (to about 70% maximal association) of plots of $k_s$ versus C.

Dissociation data were analyzed according to one site (AB=A+B) or two sites (AiBj=Ai+Bj) models, and rate constants ($k_{off}$) were calculated from best fit curves. The binding site model was used except when the residuals were greater than machine background (2-10 RU, according to machine), in which case the two-binding site model was employed. Half-times of receptor occupancy were calculated using the relationship $t_{1/2}=0.693/k_{off}$.

Flow Cytometry

Murine mAb L307.4 (anti-CD80) was purchased from Becton Dickinson (San Jose, Calif.) and IT2.2 (anti-B7-0 [also known as CD86]), from Pharmingen (San Diego, Calif.). For immunostaining, CD80-positive and/or CD86-positive CHO cells were removed from their culture vessels by incubation in phosphate-buffered saline (PBS) containing 10 mM EDTA. CHO cells ($1-10\times10^5$) were first incubated with InAbs or immunoglobulin fusion proteins in DMEM containing 10% fetal bovine serum (FBS), then washed and incubated with fluorescein isothiocyanate-conjugated goat anti-mouse or anti-human immunoglobulin second step reagents (Tago, Burlingame, Calif.). Cells were given a final wash and analyzed on a FACScan (Becton Dickinson).

SDS-PAGE and Size Exclusion Chromatography

SDS-PAGE was performed on Tris/glycine 4-20% acrylamide gels (Novex, San Diego, Calif.). Analytical gels were stained with Coomassie Blue, and images of wet gels were obtained by digital scanning. CTLA4Ig (25 µg) and L104EA29YIg (25 µg) were analyzed by size exclusion chromatography using a TSK-GEL G300 $SW_{XL}$ column (7.8× 300mm, Tosohaas, Montgomeryville, Pa.) equilibrated in phosphate buffered saline containing 0.02% $NAN_3$ at a flow rate of 1.0 ml/min.

CTLA4X$_{C120S}$ and L104EA29YX$_{C120S}$

Single chain CTLA4X$_{C120S}$ was prepared as previously described (Linsley et al., (1995) J. Biol. Chem., 270:15417-15424). Briefly, an oncostatin M CTLA4 (OMCTLA4) expression plasmid was used as a template, the forward primer,

GAGGTGATAAAGCTTCACCAATGGGTGTACTGCTCACACAG was chosen to match sequences in the vector; and the reverse primer,

GTGGTGTATTGGTCTAGATCAATCAGAATCTGGGCACGGTTC corresponded to the last seven amino acids (i.e. amino acids 118-124) in the extracellular domain of CTLA4, and contained a restriction enzyme site, and a stop codon (TGA). The reverse primer specified a C120S (cysteine to serine at position 120) mutation. In particular, the nucleotide sequence GCA (nucleotides 34-36) of the reverse primer shown above is replaced with one of the following nucleotide sequences: AGA, GGA, TGA, CGA, ACT, or GCT. As persons skilled in the art will understand, the nucleotide sequence GCA is a reversed complementary sequence of the codon TGC for cysteine. Similarly, the nucleotide sequences AGA, GGA, TGA, CGA, ACT, or GCT are the reversed complementary sequences of the codons for serine. Polymerase chain reaction products were digested with HindIII/XbaI and directionally subdloned into the expression vector πLN (Bristol-Myers Squibb Company, Princeton, N.J.). L104EA29YX$_{C120S}$ was prepared in an identical manner. Each construct was verified by DNA sequencing.

Identification and Biochemical Characterization of High Avidity Mutants

Twenty four amino acids were chosen for mutagenesis and the resulting ~2300 mutant proteins assayed for CD86Ig binding by surface plasmon resonance (SPR; as described, supra). The predominant effects of mutagenesis at each site are summarized in Table II. Random mutagenesis of some amino acids in the S25-R33 apparently did not alter ligand binding. Mutagenesis of E31 and R33 and residues M97-Y102 apparently resulted in reduced ligand binding. Mutagenesis of residues, S25, A29, and T30, K93, L96, Y103, L104, and G105, resulted in proteins with slow "on" and/or slow "off" rates. These results confirm previous findings that residues in the S25-R33 region, and residues in or near M97-Y102 influence ligand binding (Peach et al., (1994) J. Exp. Med., 180:2049-2058).

Mutagenesis of sites S25, T30, K93, L96, Y103, and G105 resulted in the identification of some mutant proteins that had slower "off" rates from CD86Ig. However, in these instances, the slow "off" rate was compromised by a slow "on" rate which resulted in mutant proteins with an overall avidity for CD86Ig that was apparently similar to that seen with wild type CTLA4Ig. In addition, mutagenesis of K93 resulted in significant aggregation which may have been responsible for the kinetic changes observed.

Random mutagenesis of L104 followed by COS cell transfection and screening by SPR of culture media samples over immobilized CD86Ig yielded six media samples containing mutant proteins with approximately 2-fold slower "off" rates than wild type CTLA4Ig. When the corresponding cDNA of these mutants were sequenced, each was found to encode a leucine to glutamic acid mutation (L104E). Apparently, substitution of leucine 104 to aspartic acid (L104D) did not affect CD86Ig binding.

Mutagenesis was then repeated at each site listed in Table II, this time using L104E as the PCR template instead of wild type CTLA4Ig, as described above. SPR analysis, again using immobilized CD86Ig, identified six culture media samples from mutagenesis of alanine 29 with proteins having approximately 4-fold slower "off" rates than wild type CTLA4Ig. The two slowest were tyrosine substitutions (L104EA29Y), two were leucine (L104EA29L), one was tryptophan (L104EA29W), and one was threonine (L104EA29T). Apparently, no slow "off" rate mutants were identified when alanine 29 was randomly mutated, alone, in wild type CTLA4Ig.

Figure 10A:
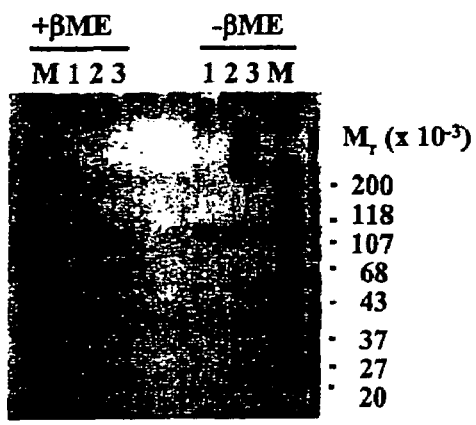
FIGS. 10A-C are an SDS gel (FIG. 10A) for CTLA4Ig (lane 1), L104EIg (lane 2), and L104EA29YIg (lane 3A); and size exclusion chromatographs of CTLA4Ig (FIG. 10B) and L104EA29YIg (FIG. 10C).
Figure 10B:
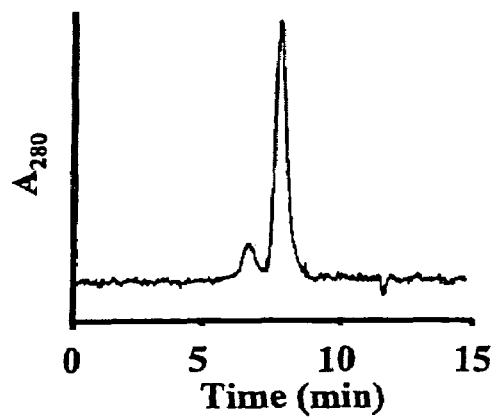
Figure 10C:
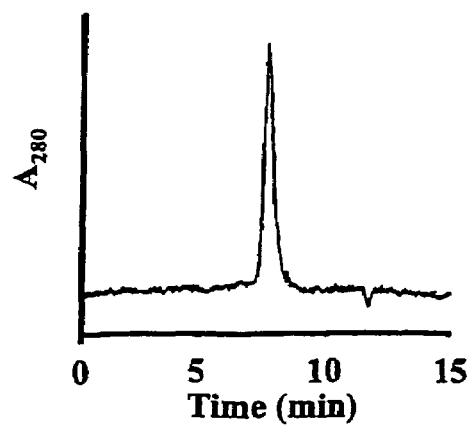

The relative molecular mass and state of aggregation of purified L104E and L104EA29YIg was assessed by SDS-PAGE and size exclusion chromatography. L104EA29YIg (~1 μg; lane 3) and L104EIg (~1 μg; lane 2) apparently had the same electrophoretic mobility as CTLA4Ig (~1 μg; lane 1) under reducing (~50 kDa; +βME; plus 2-mercaptoethanol) and non-reducing (~100 kDa; −βME) conditions (FIG. 10A). Size exclusion chromatography demonstrated that L104EA29YIg (FIG. 10C) apparently had the same mobility as dimeric CTLA4Ig (FIG. 10B). The major peaks represent protein dimer while the faster eluting minor peak in FIG. 10B represents higher molecular weight aggregates. Approximately 5.0% of CTLA4Ig was present as higher molecular weight aggregates but there was no evidence of aggregation of L104EA29YIg or L104EIg. Therefore, the stronger binding to CD86Ig seen with L104EIg and L104EA29YIg could not be attributed to aggregation induced by mutagenesis.

Equilibrium and Kinetic Binding Analysis

Equilibrium and kinetic binding analysis was performed on protein A purified CTLA4Ig, L104EIg, and L104EA29YIg using surface plasmon resonance (SPR). The results are shown in Table I.

CTLA4Ig. Since the introduction of these mutations did not significantly affect "on" rates, the increase in avidity for CD80Ig and CD86Ig observed with L104EA29YIg was likely primarily due to a decrease in "off" rates.

To determine whether the increase in avidity of L104EA29YIg for CD86Ig and CD80Ig was due to the mutations affecting the way each monomer associated as a dimer, or whether there were avidity enhancing structural changes introduced into each monomer, single chain constructs of CTLA4 and L104EA29Y extracellular domains were prepared following mutagenesis of cysteine 120 to serine as described supra, and by Linsley et al., (1995) J. Biol. Chem., 270:15417-15424. The purified proteins CTLA4$X_{C120S}$ and L104EA29Y$X_{C120S}$ were shown to be monomeric by gel permeation chromatography (Linsley et al., (1995), supra), before their ligand binding properties were analyzed by SPR. Results showed that binding affinity of both monomeric proteins for CD86Ig was approximately 35-80-fold less than that seen for their respective dimers (Table I). This supports previously published data establishing that dimerization of CTLA4 was required for high avidity ligand binding (Greene et al., (1996) J. Biol. Chem., 271:26762-26771).

L104EA29Y$X_{C120S}$ bound with approximately 2-fold higher affinity than CTLA4$X_{C120S}$ to both CD80Ig and CD86Ig. The increased affinity was due to approximately 3-fold slower rate of dissociation from both ligands. Therefore, stronger ligand binding by L104EA29Y was most likely due to avidity enhancing structural changes that had been introduced into each monomeric chain rather than alterations in which the molecule dimerized.

TABLE I

Equilibrium and Apparent Kinetic Constants

| Immobilized Protein | Analyte | $k_{on}$ (×10$^5$) M$^{-1}$ S$^{-1}$ | $k_{off}$ (×10$^{-3}$) S$^{-1}$ | $K_d$ nM |
|---|---|---|---|---|
| CD80Ig | CTLA4Ig | 3.44 ± 0.29 | 2.21 ± 0.18 | 6.51 ± 1.08 |
| CD80Ig | L104EIg | 3.02 ± 0.05 | 1.35 ± 0.08 | 4.47 ± 0.36 |
| CD80Ig | L104EA29YIg | 2.96 ± 0.20 | 1.08 ± 0.05 | 3.66 ± 0.41 |
| CD80Ig | CTLA4$X_{C120S}$ | 12.0 ± 1.0 | 230 ± 10 | 195 ± 25 |
| CD80Ig | L104EA29Y$X_{C120S}$ | 8.3 ± 0.26 | 71 ± 5 | 85.0 ± 2.5 |
| CD86Ig | CTLA4Ig | 5.95 ± 0.57 | 8.16 ± 0.52 | 13.9 ± 2.27 |
| CD86Ig | L104EIg | 7.03 ± 0.22 | 4.26 ± 0.11 | 6.06 ± 0.05 |
| CD86Ig | L104EA29YIg | 6.42 ± 0.40 | 2.06 ± 0.03 | 3.21 ± 0.23 |
| CD86Ig | CTLA4$X_{C120S}$ | 16.5 ± 0.5 | 840 ± 55 | 511 ± 17 |
| CD86Ig | L104EA29Y$X_{C120S}$ | 11.4 ± 1.6 | 300 ± 10 | 267 ± 29 |

(values are means ± standard deviation from three different experiments)

Observed equilibrium dissociation constants ($K_d$; Table I) were calculated from binding curves generated over a range of concentrations (5.0-200 nM). L104EA29YIg binds more strongly to CD86Ig than does L104EIg or CTLA4Ig. The lower $K_d$ of L104EA29YIg (3.21 nM) than L104EIg (6.06 nM) or CTLA4Ig (13.9 nM) indicates higher binding avidity of L104EA29YIg to CD86Ig. The lower $K_d$ of L104EA29YIg (3.66 nM) than L104EIg (4.47 nM) or CTLA4Jg (6.51 nM) indicates higher binding avidity of L104EA29YIg to CD80Ig.

Figures 11A, 11B:
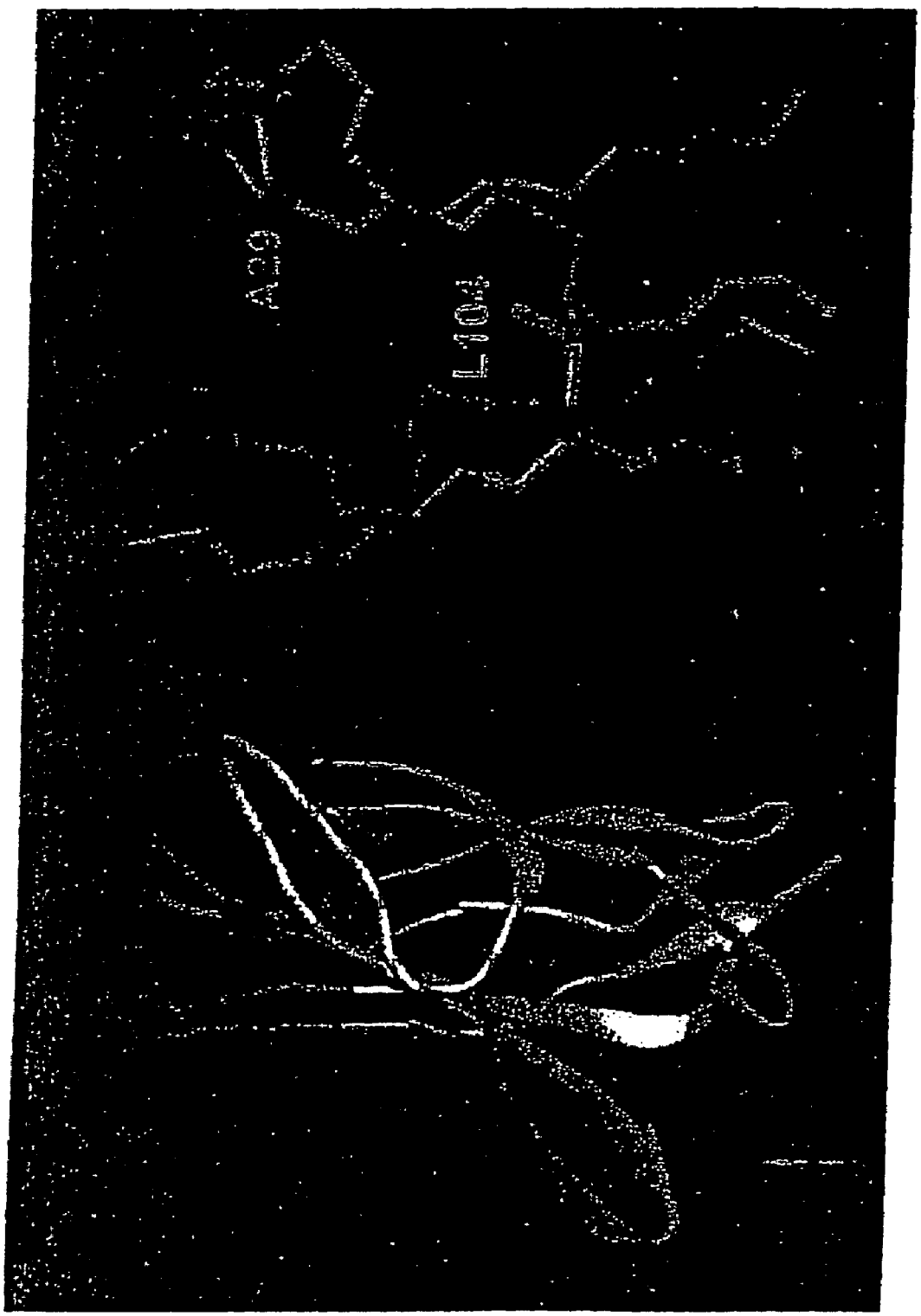
FIGS. 11A and 11B illustrate a ribbon diagram of the CTLA4 extracellular Ig V-like fold generated from the solution structure determined by NMR spectroscopy.

Kinetic binding analysis revealed that the comparative "on" rates for CTLA4Ig, L104EIg, and L104EA29YIg binding to CD80 were similar, as were the "on" rates for CD86Ig (Table I). However, "off" rates for these molecules were not equivalent (Table I). Compared to CTLA4Ig, L104EA29YIg had approximately 2-fold slower "off" rate from CD80Ig, and approximately 4-fold slower "off" rate from CD86Ig. L104E had "off" rates intermediate between L104EA29YIg and Location and Structural Analysis of Avidity Enhancing Mutations The solution structure of the extracellular IgV-like domain of CTLA4 has recently been determined by NMR spectroscopy (Metzler et al., (1997) Nature Struct. Biol., 4:527-531. This allowed accurate location of leucine 104 and alanine 29 in the three dimensional fold (FIG. 11A-B). Leucine 104 is situated near the highly conserved MYPPPY amino acid sequence. Alanine 29 is situated near the C-terminal end of the S25-R33 region, which is spatially adjacent to the MYPPPY region. While there is significant interaction between residues at the base of these two regions, there is apparently no direct interaction between L104 and A29 although they both comprise part of a contiguous hydrophobic core in the protein. The structural consequences of the two avidity enhancing mutants were assessed by modeling. The A29Y mutation can be easily accommodated in the cleft between the S25-R33 region and the MYPPPY region, and may serve to stabilize the conformation of the MYPPPY region. In wild type CTLA4, L104 forms extensive hydrophobic interactions with L96 and V94 near the MYPPPY region. It is highly unlikely that the glutamic acid mutation adopts a conformation similar to that of L104 for two reasons. First, there is insufficient space to accommodate the longer glutamic acid side chain in the structure without significant perturbation to the S25-R33 region. Second, the energetic costs of burying the negative charge of the glutamic acid side chain in the hydrophobic region would be large. Instead, modeling studies predict that the glutamic acid side chain flips out on to the surface where its charge can be stabilized by solvation. Such a conformational change can easily be accommodated by G105, with minimal distortion to other residues in the regions.

Binding of High Avidity Mutants to CHO Cells Expressing CD80 or CD86

FACS analysis (FIG. 2) of CTLA4Ig and mutant molecules binding to stably transfected CD80+ and CD86+CHO cells was performed as described herein. CD80-positive and CD86-positive CHO cells were incubated with increasing concentrations of CTLA4Ig, L104EA29YIg, or L104EIg, and then washed. Bound immunoglobulin fusion protein was detected using fluorescein isothiocyanate-conjugated goat anti-human immunoglobulin.

As shown in FIG. 2, CD80-positive or CD86-positive CHO cells ($1.5 \times 10^5$) were incubated with the indicated concentrations of CTLA4Ig (closed squares), L104EA29YIg (circles), or L104EIg (triangles) for 2 hr. at 23° C., washed, and incubated with fluorescein isothiocyanate-conjugated goat anti-human immunoglobulin antibody. Binding on a total of 5,000 viable cells was analyzed (single determination) on a FACScan, and mean fluorescence intensity (MFI) was determined from data histograms using PC-LYSYS. Data were corrected for background fluorescence measured on cells incubated with second step reagent only (MFI=7). Control L6 mAb (80 µg/ml) gave MFI<30. These results are representative of four independent experiments.

Figure 2A:
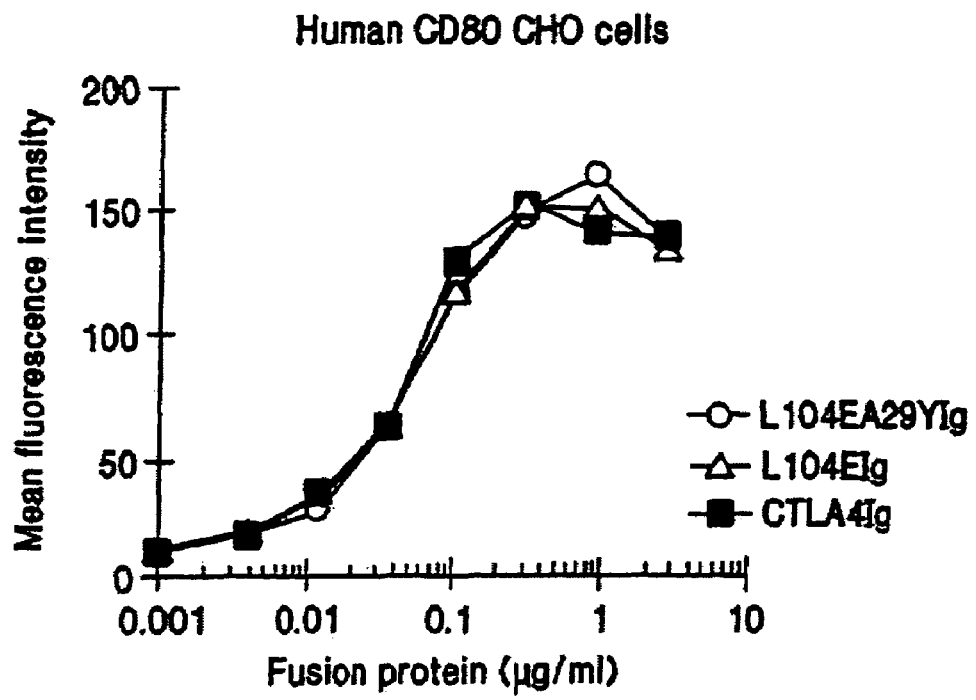
FIGS. 2A & 2B illustrate data from FACS assays showing binding of L104EA29YIg, L104EIg, and CTLA4Ig to human CD80- or CD86-transfected CHO cells as described in Example 2, infra.
Figure 2B:
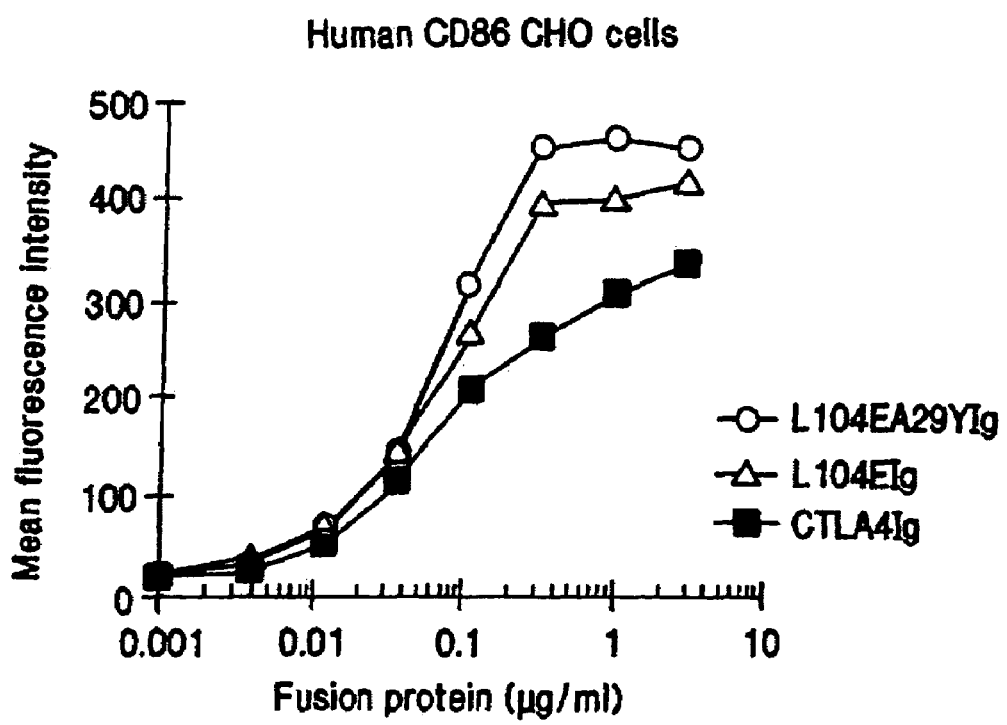

Binding of L104EA29YIg, L104EIg, and CTLA4Ig to human CD80-transfected CHO cells is approximately equivalent (FIG. 2A). L104EA29YIg and L104EIg bind more strongly to CHO cells stably transfected with human CD86 than does CTLA4Ig (FIG. 2B).

Functional Assays

Figure 3A:
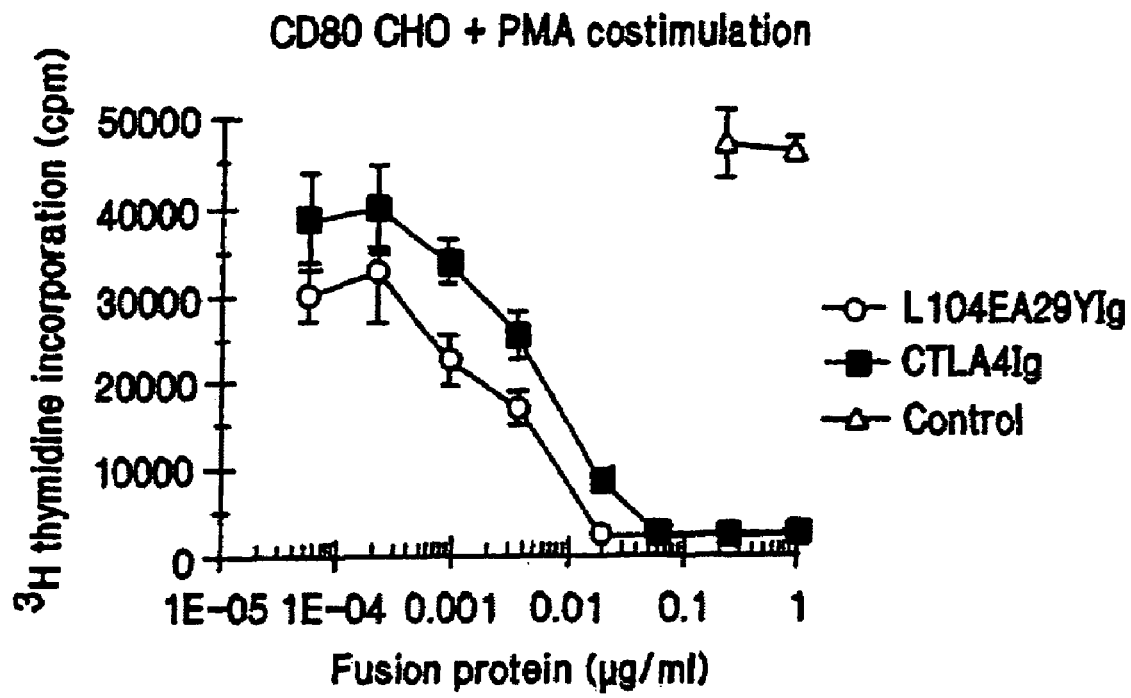
FIGS. 3A & 3B depicts inhibition of proliferation of CD80-positive and CD86-positive CHO cells as described in Example 2, infra.
Figure 3B:
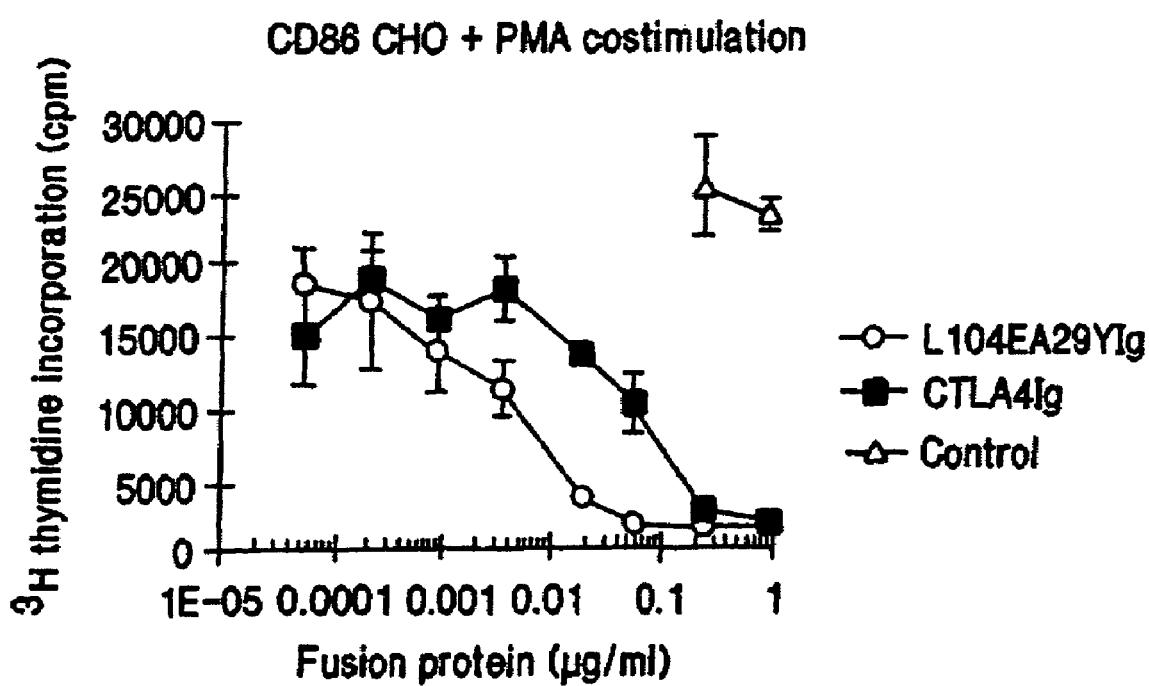

Human CD4-positive T cells were isolated by immunomagnetic negative selection (Linsley et al., (1992) J. Exp. Med. 176:1595-1604). Isolated CD4-positive T cells were stimulated with phorbal myristate acetate (PMA) plus CD80-positive or CD86-positive CHO cells in the presence of titrating concentrations of inhibitor. CD4-positive T cells ($8-10 \times 10^4$/well) were cultured in the presence of 1 nM PMA with or without irradiated CHO cell stimulators. Proliferative responses were measured by the addition of 1 µCi/well of [3H]thymidine during the final 7 hours of a 72 hour culture. Inhibition of PMA plus CD80-positive CHO, or CD86-positive CHO, stimulated T cells by L104EA29YIg and CTLA4Ig was performed. The results are shown in FIG. 3. L104EA29YIg inhibits proliferation of CD80-positive PMA treated CHO cells more than CTLA4Ig (FIG. 3A). L104EA29YIg is also more effective than CTLA4Ig at inhibiting proliferation of CD86-positive PMA treated CHO cells (FIG. 3B). Therefore, L104EA29YIg is a more potent inhibitor of both CD80- and CD86-mediated costimulation of T cells.

FIG. 4 shows inhibition by L104EA29YIg and CTLA4Ig of allostimulated human T cells prepared above, and further allostimulated with a human B lymphoblastoid cell line (LCL) called PM that expressed CD80 and CD86 (T cells at $3.0 \times 10^4$/well and PM at $8.0 \times 10^3$/well). Primary allostimulation occurred for 6 days, then the cells were pulsed with $^3$H-thymidine for 7 hours, before incorporation of radiolabel was determined.

Figure 4A:
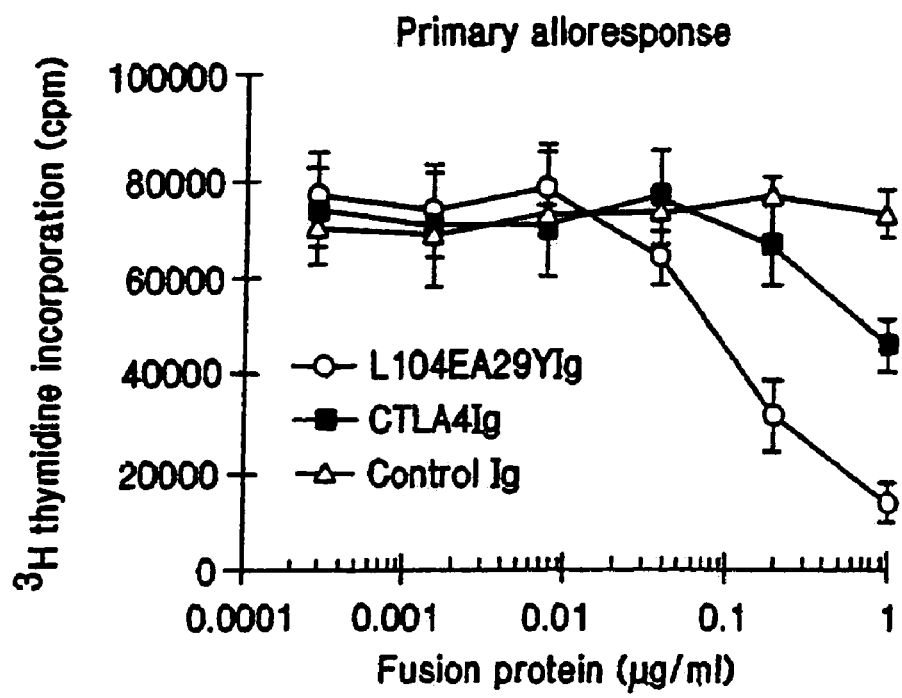
FIGS. 4A & 4B shows that L104EA29YIg is more effective than CTLA4Ig at inhibiting proliferation of primary and secondary allostimulated T cells as described in Example 2, infra.
Figure 4B:
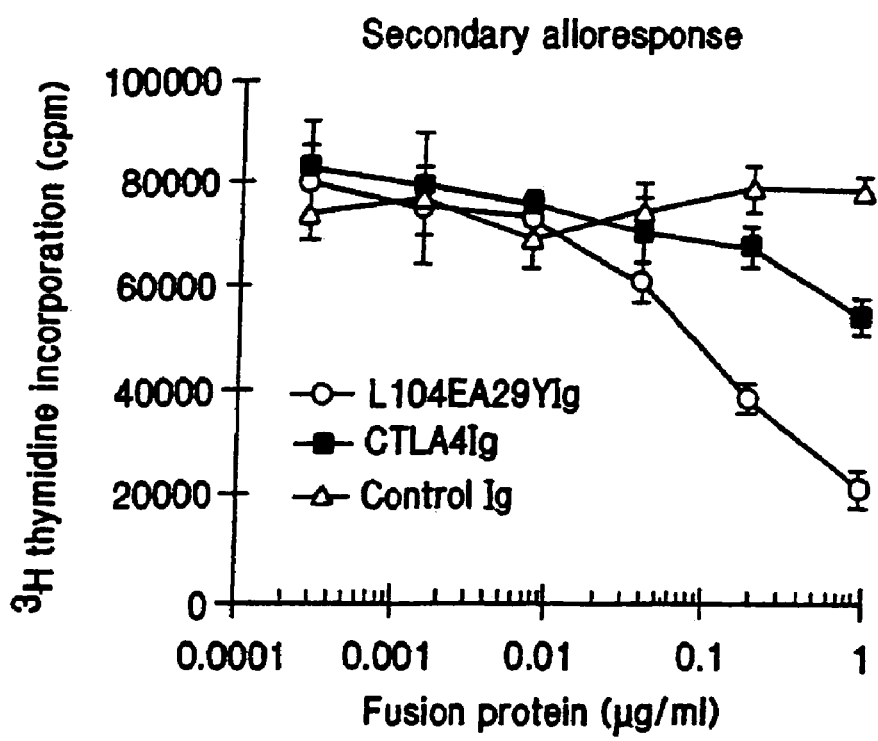

Secondary allostimulation was performed as follows. Seven day primary allostimulated T cells were harvested over lymphocyte separation medium (LSM) (ICN, Aurora, Ohio) and rested for 24 hours. T cells were then restimulated (secondary), in the presence of titrating amounts of CTLA4Ig or L104EA29YIg, by adding PM in the same ratio as above. Stimulation occurred for 3 days, then the cells were pulsed with radiolabel and harvested as above. The effect of L104EA29YIg on primary allostimulated T cells is shown in FIG. 4A. The effect of L104EA29YIg on secondary allostimulated T cells is shown in FIG. 4B. L104EA29YIg inhibits both primary and secondary T cell proliferative responses better than CTLA4Ig.

Figure 5A:
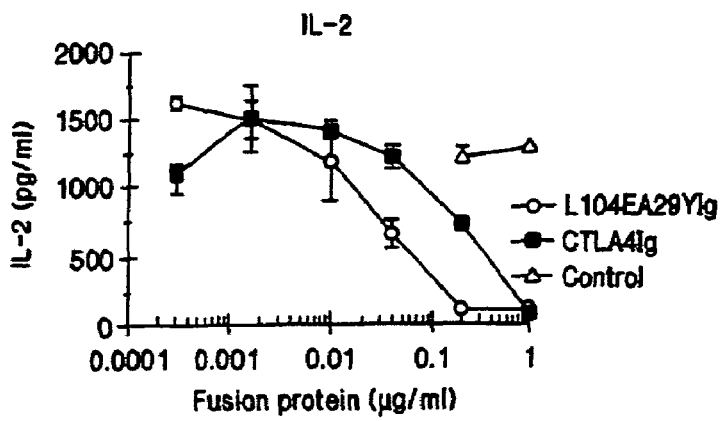
FIGS. 5A-C illustrate that L104EA29YIg is more effective than CTLA4Ig at inhibiting IL-2 (FIG. 5A), IL-4 (FIG. 5B), and γ-interferon (FIG. 5C) cytokine production of allostimulated human T cells as described in Example 2, infra.
Figure 5B:
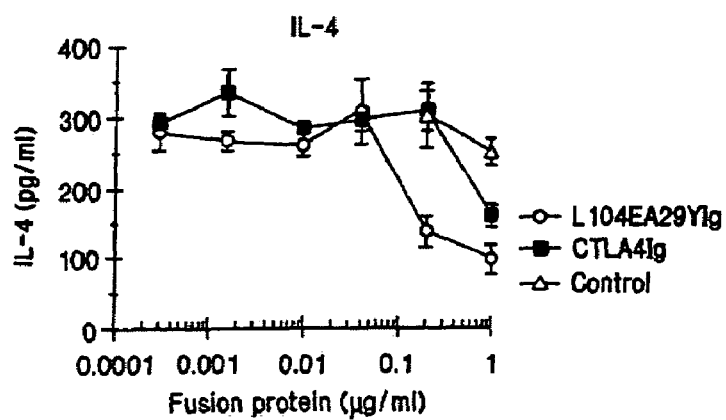
Figure 5C:
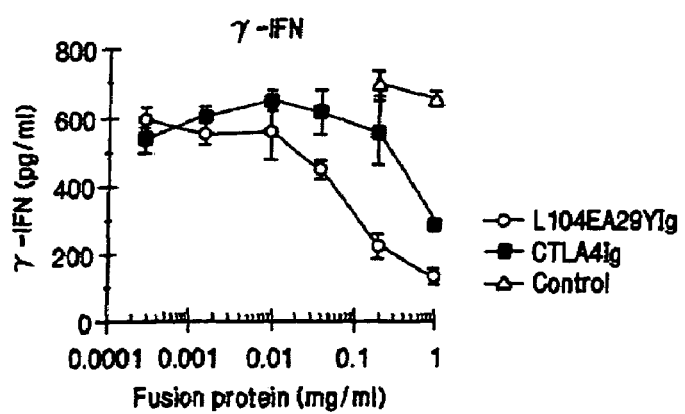

To measure cytokine production (FIG. 5), duplicate secondary allostimulation plates were set up. After 3 days, culture media was assayed using ELISA kits (Biosource, Camarillo, Calif.) using conditions recommended by the manufacturer. L104EA29YIg was found to be more potent than CTLA4Ig at blocking T cell IL-2, IL-4, and γ-IFN cytokine production following a secondary allogeneic stimulus (FIGS. 5A-C).

Figure 6:
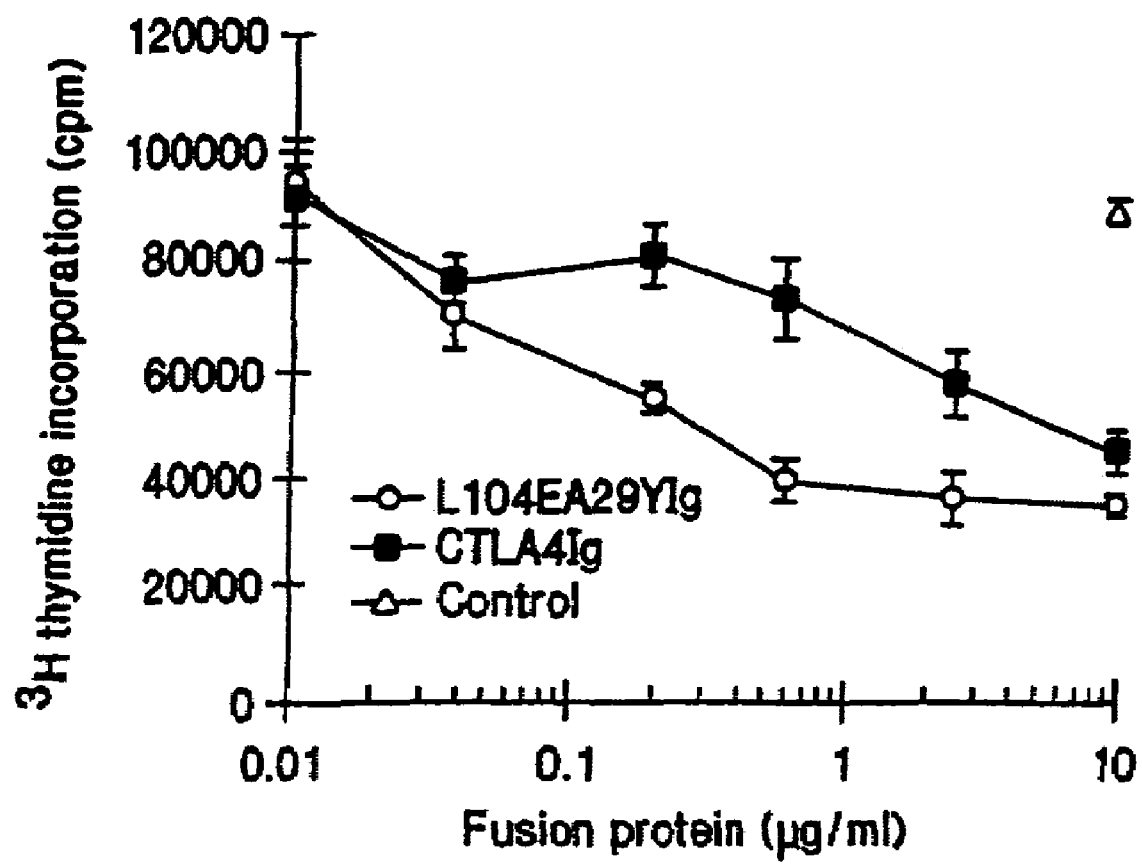
FIG. 6 demonstrates that L104EA29YIg is more effective than CTLA4Ig at inhibiting proliferation of phytohemaglutinin-(PHA) stimulated monkey T cells as described in Example 2, infra.

The effects of L104EA29YIg and CTLA4Ig on monkey mixed lymphocyte response (MLR) are shown in FIG. 6. Peripheral blood mononuclear cells (PBMC'S; $3.5 \times 10^4$ cells/well from each monkey) from 2 monkeys were purified over lymphocyte separation medium (LSM) and mixed with 2 µg/ml phytohemaglutinin (PHA). The cells were stimulated 3 days then pulsed with radiolabel 16 hours before harvesting. L104EA29YIg inhibited monkey T cell proliferation better than CTLA4Ig.

TABLE II

The effect on CD86Ig binding by mutagenesis of CTLA4Ig at the sites listed

| | Effects of Mutagenesis | | |
|---|---|---|---|
| Mutagenesis Site | No Apparent Effect | Slow "on" rate/slow "off rate | Reduced ligand binding |
| S25 | | + | |
| P26 | + | | |
| G27 | + | | |
| K28 | + | | |
| A29 | | + | |
| T30 | | + | |
| E31 | | | + |
| R33 | | | + |
| K93 | | + | |
| L96 | | + | |
| M97 | | | + |
| Y98 | | | + |
| P99 | | | + |
| P100 | | | + |
| P101 | | | + |
| Y102 | | | + |
| Y103 | | + | |
| L104 | | + | |
| G105 | | + | |
| I106 | + | | |
| G107 | + | | |
| Q111 | + | | |
| Y113 | + | | |
| I115 | + | | |

(The predominant effect is indicated with a "+" sign)

Example 3

This study compared the efficacy and safety of L104EA29YIg, described above, as a maintenance immunosuppressant with CsA over 12 months when used as part of a CNI-free combination regimen consisting of basiliximab (Simulect®; Novartis) induction, mycophenolate mofetil (MMF; CellCept®; Roche), and corticosteroids in renal transplant recipients.

Adult recipients of a non-HLA-identical renal allograft from a living or deceased donor were eligible. Subjects with a prior renal transplant, a history of panel-reactive antibodies of >20%, or those deemed by the investigator to be at higher risk of acute rejection were restricted to ≦10% of the study population. Exclusion criteria included underlying renal disease of focal and segmental glomerulosclerosis, Type I or II membranoproliferative glomerulonephritis, or hemolytic uremic syndrome/thrombotic thrombocytopenic purpura; active hepatitis B or C, or HIV; and donor age >60 or <6, donors with cardiac death, or donor kidney cold ischemia time of >36 hours.

This was an open-label, randomized, active-controlled, multiple-dose, multicenter study performed in the United States, Europe and Canada. Eligible patients of either sex aged ≧18 years undergoing a renal transplant (deceased or living donor, except when donor and recipient were HLA-identical) were randomized to treatment in a 1:1:1 ratio with an L104EA29YIg more-intensive (MI) treatment regimen, L104EA29YIg less-intensive (LI) treatment regimen, or Cyclosporine A (CsA); all in combination with induction therapy with basiliximab (Simulect®; Novartis), adjunctive maintenance therapy with mycophenolate mofetil (MMF; CellCept®; Roche), and corticosteroids. Both L104EA29YIg regimens included an early phase, in which L104EA29YIg was administered at 10 mg/kg, and a maintenance phase, in which L104EA29YIg was administered at 5 mg/kg at q4 week or q8 week intervals. Doses for each regimen were based on body weight. These doses were dictated by the target trough profiles shown to be effective during non-human primate studies. These profiles necessitated doses that were higher initially, during the period of greatest immunologic risk (Day 0-90). The early phase was longer in the MI regimen (6 vs. 3 months) and included more frequent dosing.

L104EA29YIg more intensive (MI) treatment regimen consisted administration of 10 mg/kg on days 1, 5, 15, 29, 43, 57, 71, 85, 113, 141 and 169, followed by 5 mg/kg every 4 or 8 weeks. L104EA29YIg less intensive (LI) treatment regimen consisted of 10 mg/kg on days 1, 15, 29, 57 and 85, followed by 5 mg/kg every 4 or 8 weeks. L104EA29YIg was administered in a 30-minute intravenous infusion. Patients randomized to CsA received twice-daily doses (7±3 mg/kg) to achieve the pre-specified range of target serum concentrations of 150-400 ng/ml during the first month and 150-300ng/ml during months 2-12, which is consistent with current medical practice. All patients received MMF 2 g daily and basiliximab 20 mg every 4 days. A corticosteroid tapering regimen was also given consisting of an iv bolus of methylprednisolone 500 mg on Day 1 and 250 mg on Day 2, followed by oral prednisone 100 mg on Day 3, 50 mg on Day 4, 25 mg on Days 5-30, 22.5 mg on Days 31-44, 20 mg on Days 45-58, 17.5 mg on Days 59-72, 15 mg on Day 73-86, 12.5 mg on Days 87-100, and 10 mg on Days 101-114. After Day 114, the prednisone dose could be decreased by 2.5 mg every other month but not to less than 5 mg per day.

The primary objective was to demonstrate that L104EA29YIg was not inferior to CsA in the prevention of acute rejection at 6 months. Secondary objectives included assessment of the incidence of acute rejection (biopsy-confirmed or presumed) at 6 months and 1 year; measured glomerular filtration rate (GFR) via iohexol clearance at 1, 6, and 12 months; parameters of hypertension; serum cholesterol and triglycerides; and overall safety. Other pre-specified analyses included patient death or graft loss at 1 year; the severity of acute rejection; the incidence of post-transplant diabetes mellitus [defined as any therapy required for hyperglycemia for ≧4 weeks, or a hemoglobin A1C (HbA1c) >7%, in patients not previously known to be diabetic]; calculated GFR, using the Modification of Diet in Renal Disease (MDRD, Levey A S, Bosch J P, Lewis J P, Greene T, Rogers N, Roth D. A more accurate method to estimate glomerular filtration rate from serum creatinine: a new prediction equation. Modification of Diet in Renal Disease Study Group. Ann Intern Med 1999;130:461-470), Jelliffe (R W. Creatinine clearance: Bedside estimate. Ann Inter Med. 1973;79:604-605), Cockcroft-Gault (Cockcroft D W, Gault M H. Prediction of creatinine clearance from serum creatinine. Nephron 1976; 16:31-41), and Nankivell (Nankivell B J, Gruenewald S M, Allen R D, Chapman J R. Predicting glomerular filtration rate after kidney transplantation. Transplantation. 1995; 59(12):1683-1689) formulas; pharmacokinetics and immunogenicity. Diagnosis and treatment of acute rejection (AR) was based on the Banff 97 criteria and grade (Racusen L C, Solez K, Colvin R B, et al. The Banff 97 working classification of renal allograft pathology. Kidney Int 1999;55(2):713-23.). A post-hoc analysis was conducted of the incidence of chronic allograft nephropathy (CAN).

Diagnosis and treatment of acute rejection (AR) was based on the Banff 97 criteria and grade (Racusen L C, Solez K, Colvin R B, et al. The Banff 97 working classification of renal allograft pathology. Kidney Int 1999;55(2):713-23.). Intraoperative renal allograft biopsies were performed to assess baseline histology. Biopsied tissue was stained and graded according to the Banff 97 working classification of kidney transplant pathology. Biopsies were evaluated by an independent pathologist blinded to treatment to confirm all episodes of clinically-suspected AR prior to treatment for AR.

Additional endpoints included: clinically suspected and biopsy proven acute rejection (CSBPAR) at 12 months; death or graft loss at 1 year; severity of AR episodes (measured using the Banff 97 scale); treatment failure (defined as investigator opinion; ≧grade IIB rejection; recurrent or steroid-resistant rejection); renal function at 1, 6 and 12 months (glomerular filtration rates [GFRs] assessed by Iohexol clearance) and evidence of chronic allograft nephropathy (CAN) (interstitial fibrosis and tubular atrophy); parameters of hypertension (diastolic blood pressure [BP]≧90 mm Hg and/or systolic BP≧140 mm Hg); serum lipids; safety, tolerability and adverse events (AEs) in patients treated with L104EA29YIg compared with CsA-treated patients.

For safety and tolerability assessments, AEs, laboratory measurements (hematology, biochemistry and urine analysis) and vital signs were recorded during regular scheduled clinic visits.

Results

A total of 218 patients underwent renal transplantation and were randomized to the MI group (N=74), LI group (N=71), or CsA (N=73). Baseline demographics and clinical characteristics were similar between the three treatment groups. A total of 164 patients completed 1 year of treatment. Of the patients who discontinued prior to 1 year (N=16 vs 16 vs 20; MI regimen versus LI regimen versus CsA), the most common reasons were AEs (N=5 versus 8 vs 9) and treatment failure (N=7 versus 5 versus 3).

The incidence of CSBPAR occurred infrequently in all treatment groups, and there was no statistically significant difference in the incidence of either CSBPAR or biopsy proven acute rejection (BPAR) between treatment groups. At 6 and 12 months, incidence of CSBPAR was 6.8%, 5.6% and 8.2% for MI, LI and CsA treatment, respectively.

Incidence of BPAR was also similar between groups at 6 and 12 months, although BPAR was slightly higher in the LI group than in the other two groups (18.9%, 29.6% and 17.8% for MI, LI and CsA treatment respectively). Biopsy-proven acute rejection was more frequent than CSBPAR in all treatment groups, and was most common in the LI group. However, many of these events were found to occur in patients with L104EA29YIg at below desired trough serum concentrations.

No statistically significant difference between treatment groups was seen in the severity of AR; however, numbers were small and did not result in graft loss.

This study was unblinded to study medication in order to permit standard of care with respect to CsA, which probably contributed to the increased number of biopsies taken in the L104EA29YIg groups (N=345) compared with the CsA group (N=144). Although this is not unexpected for a study designed in this way, it could have increased the rate of diagnosis of renal histological abnormalities in the L104EA29YIg treatment groups.

Death and/or graft loss was infrequent in all treatment groups, with 1 death reported in the MI group, 4 in the CsA group and none in the LI group. Most graft losses were not caused by immunologic events and only 3 grafts were lost in the MI and CsA groups versus 1 in the LI group.

Significant improvements in renal function were seen with L104EA29YIg-based treatment compared to CsA-based immunosuppression. Iohexol clearance was greater with L104EA29YIg treatment at all time-points, with a mean improvement of 11 ml/min/1.73m$^2$ (~20%) compared with CsA at 12 months.

At 12 months, chronic allograft nephropathy (CAN) was between 30 and 50% less common, in relative terms, in L104EA29YIg—than CsA-treated patients. Rates of new or worsening CAN at 12 months were 29%, 19% and 44% for MI, LI and CsA groups, respectively.

At 1 year, mean systolic blood pressure was 3-4 mmHg higher in patients treated with CsA (133 mmHg) versus patients in the MI (130 mmHg) and LI (129 mmHg) treatment groups. This was despite lower use of anti-hypertensive medication in the L104EA29YIg groups (MI: 87.5%; LI84.1%: CsA 92.2%). Total serum cholesterol was slightly lower with L104EA29YIg (MI: 198 mg/dL; LI: 201 mg/dL) versus CsA- (212 mg/dL) treated patients although lipid-lowering medication use was also lower with L104EA29YIg (MI: 36.1%; LI: 31.9%; CsA : 53.1%).

Four (5.5%) patients died in the CsA group compared with 1 in the L104EA29YIg treatment groups. Rates of adverse events (AEs) were comparable between treatment groups; however, related AEs were significantly lower following L104EA29YIg treatment than CsA treatment. Intravenous administration of L104EA29YIg was well tolerated with no infusion reactions. L104EA29YIg-treated patients did not exhibit typical CsA-related adverse events, such as anemia, leucopenia, hirsutism, tremor and gingival hyperplasia. L104EA29YIg-based therapy was not associated with any increased risk of infections or malignancies compared with CsA-based therapy.

Conclusion

This 12-month study demonstrates that L104EA29YIg-based maintenance therapy confers equivalent efficacy in preventing AR and similar patient and graft survival compared with CsA. In addition, L104EA29YIg demonstrated significant improvements in renal function and reductions in CAN compared with CsA-based maintenance immunosuppression. L104EA29YIg was safe and well tolerated and was not associated with typical CNI-related toxicities.

Rates of CSBPAR and BPAR were similar between the three treatment groups demonstrating that the low AR rates observed with CsA-based therapy are also achieved with L104EA29YIg. The majority of BPARs were classified as sub-clinical, suggesting that renal function was not impaired. The numerically lower rate of AR in the MI group, compared with the LI group, suggests a possible dose-dependent response with L104EA29YIg. More frequent biopsies in the L104EA29YIg groups could potentially have led to over-diagnosis of both acute and chronic rejection in these groups, suggesting that the benefits of L104EA29YIg therapy may be understated in this study.

The majority of BPAR events occurred within the first three post-transplant months, which is not unexpected since others have shown that higher doses of immunosuppressants are required during the early post-transplantation period (Wiecek A, Nowicki M, Kokot F, Ritz E. Acute failure of the transplanted kidney—pathophysiology, diagnosis and prevention. Ann Transplant 1996; 1 (4):5-9 and Bennett W M. Posttransplant acute renal failure. Ren Fail 1997;19(2):225-6). Since the majority of these events occurred at below desired trough values, consideration should be given to altering the regimen in the first month of treatment, prior to reaching a steady state. The majority of the BPARs seen during the maintenance phase occurred at very low or undetectable levels of L104EA29YIg, suggesting that the incidence of AR during those periods was related to insufficient immunosuppression, which may be avoided by alterations in the dose regimen.

This study demonstrates that L104EA29YIg is associated with similar overall AE rates compared with CsA, with fewer AEs related to study drug. No real differences in the number of viral-related AEs were identified between the three treatment groups.

In the presence of low AR rates, the new goal of maintenance immunosuppression is reduction in long-term health complications, including hypertension, hyperlipidemia, drug toxicity, and the prevention of scarring. As in autoimmune diseases, a new generation of immunoselective maintenance immunosuppressive agents is emerging. Inhibition of T-cell co-stimulation via immunoselective co-stimulation blockade with L104EA29YIg represents a new paradigm, offering the promise of more selective maintenance immunosuppression, reduced toxicities and improved long-term outcomes in renal transplantation.

Example 4

There exists substantial unmet medical need for new therapies in renal transplantation that can provide short-term subject and graft survival comparable to the CNIs without their long-term nephrotoxic, cardiovascular, and metabolic effects. The need is particularly great among recipients of ECD define renal allografts, whose long-term subject and graft survival rates are distinctly below those of recipients of allografts from donors meeting standard eligibility criteria. L104EA29YIg, an immunosuppressive agent with a novel mechanism of action, is a promising non-nephrotoxic candidate for use in renal transplant recipients of ECD allografts. Because L104EA29YIg can be administered at the time of engraftment rather than in a delayed fashion, as is frequently necessary with CNIs—especially in those allografts with initial impaired renal function—it affords immunosuppression in a timely manner and without the need for polyclonal antilymphocyte preparations. This may translate into comparable rates of acute rejection with a favorable safety profile. As L104EA29YIg is not anticipated to be nephrotoxic, additional benefits should be seen with respect to allograft structure (ie, CAN) and function (ie, GFR). Finally, unlike CNIs, the targeted mechanism of action of L104EA29YIg should provide immunosuppression without adversely affecting the cardiovascular/metabolic profile. An overall benefit-risk assessment for the use of L104EA29YIg in this subject population is provided below.

Two dose regimens (as described in Example 3, with a minor modification to the LI regimen and using the every 4-week maintenance infusion schedule) will be studied.

Primary Objectives

1.) Evaluate the effects of L104EA29YIg, relative to CsA, on the composite of subject and graft survival at 12 months.

2.) Evaluate the effects of L104EA29YIg, relative to CsA, on the composite of measured GFR<60 mL/min/1.73 m$^2$ at Month 12 or a decrease in measured GFR>10 mL/min/1.73 m$^2$ from Month 3 to Month 12.

Secondary Objectives

1.) Evaluate the effects of L104EA29YIg, relative to CsA, on measured GFR at 12 months.

2.) Evaluate the effects of L104EA29YIg, relative to CsA, on biopsy-proven CAN by 12 months.

3.) Assess the effects of L104EA29YIg, relative to CsA, on measured GFR at 3 months, and change from baseline (3 months) to 12 months.

4.) Assess the effects of L104EA29YIg, relative to CsA, on the proportion of subjects with a measured GFR <30 mL/min/1.73 m$^2$ at 12 months.

5.) Assess the effects of L104EA29YIg, relative to CsA, on calculated GFR at 3, 12, 24, and 36 months, and change from baseline (3 months) to 12, 24, and 36 months.

6.) Assess the effects of L104EA29YIg, relative to CsA, on PTDM at 12, 24, and 36 months.

7.) Assess the effects of L104EA29YIg, relative to CsA, on measures of hypertension at 12, 24, and 36 months, including SBP and DBP, incidence and prevalence of hypertension and controlled hypertension, and intensity of treatment regimen.

8.) Assess the effects of L104EA29YIg, relative to CsA, on measures of dyslipidemia, at 12, 24, and 36 months, including serum total, non-HDL, low-density lipoprotein (LDL), and HDL cholesterol, and TGs, incidence and prevalence of dyslipidemia and controlled dyslipidemia, and intensity of treatment regimen.

9.) Evaluate the effects of L104EA29YIg, relative to CsA, on subject and graft survival at 24 and 36 months.

10.) Assess the effects of L104EA29YIg, relative to CsA, on measures of acute rejection at 6 months, including the incidence and severity of acute rejection, the use of polyclonal antilymphocyte preparations for impaired renal function and anticipated DGF, the initial use of lymphocyte-depleting therapy for treatment of acute rejection, the incidence of steroid-resistant acute rejection, the incidence of complete recovery (SCr returning to baseline) following acute rejection, the incidence of subclinical rejection, and the incidence of all treated acute rejection episodes regardless of histological findings.

11.) Evaluate the effects of L104EA29YIg, relative to CsA, on QoL.

12.) Assess the overall safety of L104EA29YIg, relative to CsA.

Tertiary Objectives

1.) Assess the effects of L104EA29YIg, relative to CsA, on the slope and intercept of calculated GFR from baseline (3 months) to 12, 24, and 36 months.

2.) Assess the effects of L104EA29YIg, relative to CsA, on the proportion of subjects with a measured GFR<45 mL/min/1.73 m$^2$ at 12 months.

3.) Assess the effects of L104EA29YIg, relative to CsA, on the proportion of subjects with <75 mL/min/1.73 m$^2$ calculated GFR at Month 12 and subjects with a decrease in calculated GFR from Month 3 to Month 12 of at least 15 mL/min/1.73 m$^2$.

4.) Assess the effects of L104EA29YIg, relative to CsA, on the incidence of DGF.

5.) Assess the effects of L104EA29YIg, relative to CsA, on measures of acute rejection at 12, 24, and 36 months, including the incidence and severity of acute rejection, the use of polyclonal antilymphocyte preparations for impaired renal function and anticipated DGF, the initial use of lymphocyte-depleting therapy for treatment of acute rejection, and the incidence of steroid-resistant acute rejection, the incidence of complete recovery (SCr returning to baseline) following acute rejection, the incidence of subclinical rejection, and the incidence of all treated acute rejection episodes regardless of histological findings.

6.) Assess the effects of L104EA29YIg, relative to CsA, on a composite cardiovascular disease endpoint (adjudicated cardiovascular death, myocardial infarction, ischemic stroke, non-elective hospitalization for cardiovascular cause, and percutaneous coronary intervention) at 12, 24, and 36 months.

7.) Assess the effects of L104EA29YIg, relative to CsA, on a composite cardiorenal disease endpoint (death, graft loss, non-fatal myocardial infarction, and stroke) at 12, 24, and 36 months.

8.) Assess the effects of L104EA29YIg, relative to CsA, on the Framingham Risk Score at 12, 24, and 36 months.

9.) Assess the effects of L104EA29YIg, relative to CsA, on incidence of discontinuation of study drug.

10.) Assess the effects of L104EA29YIg, relative to CsA, on anti-donor human leukocyte antigen (HLA) antibodies.

11.) Assess the effects of L104EA29YIg, relative to CsA, on C4d positivity in biopsy specimens.

Study Design

The duration of the study is 3 years with a subsequent 8-week follow-up period for safety evaluations. At the end of the 3-year treatment period, subjects may be eligible for a long-term extension study.

This is a randomized, partially-blinded, active-controlled, parallel-group study. All subjects will receive a kidney from a donor with extended criteria as defined below. These criteria are based in part on those issued by the United Network of Organ Sharing (UNOS); they also include other features widely used to identify potentially compromised organs, such as those from donors with cardiac death (DCD, non-heart beating) or with prolonged cold ischemia time (CIT).

Approximately 540 subjects will be randomized in a 1:1:1 ratio to treatment with either L104EA29YIg (MI regimen), L104EA29YIg (LI regimen), or CsA. All subjects will also receive induction with basiliximab and a background maintenance immunosuppressive regimen of MMF and corticosteroids. Subjects randomized to the MI regimen will receive i.v. L104EA29YIg (10 mg/kg) on Days 1 and 5, then every 2 weeks through Month 3 (Weeks 2, 4, 6, 8, 10, and 12), and then every 4 weeks through 6 months (Weeks 16, 20, and 24). After 6 months, subjects in the MI treatment group will receive the maintenance dose of L104EA29YIg 5 mg/kg administered every 4 weeks until completion of the trial at 36 months. Subjects randomized to the LI regimen will receive i.v. L104EA29YIg (10 mg/kg) on Days 1 and 5, and then every 2 weeks through Month 1 (Weeks 2 and 4), and every 4 weeks through Month 3 (Weeks 8 and 12). After 3 months, subjects in the LI treatment group will receive the maintenance dose of L104EA29YIg 5 mg/kg administered every 4 weeks until completion of the trial at 36 months.

Blinding between the LI and MI groups will be preserved with the use of placebo infusions in the LI treatment group on Weeks 6 and 10. Subjects randomized to CsA will receive doses twice daily that are designed to achieve a specified trough serum concentration range consistent with current medical practice.

The use of polyclonal antilymphocyte preparations (Thymoglobulinr or ATGAM ) is permitted—but not required— for subjects randomized to CsA who experience impaired renal allograft function and anticipated DGF. These agents are widely utilized in this capacity to afford immunosuppression until graft function recovers for administration of CsA. The decision to use and dose a polyclonal antilymphocyte preparation in this clinical setting is at the investigator's discretion within the protocol guidelines. The safety and efficacy of L104EA29YIg will be assessed at 1, 2, and 3 years.

Primary Outcome Measures

Each L104EA29YIg-based regimen will be compared to the CsA-based regimen on the following primary efficacy outcome measures: (1) the composite of subject and graft survival at 12 months; (2) the composite of measured GFR<60 mL/min/1.73 m² at Month 12 or a decrease in measured GFR$\geq$10 mL/min/1.73 m² from Month 3 to Month 12. The intent is to demonstrate non-inferiority for death and graft loss and superiority for renal function. The endpoint of subject and graft survival was selected since these measures are the most important clinical outcomes for allograft recipients. Although allograft loss can be prevented by effective immunosuppressive therapy, the same therapy may increase the risk of death from infection, PTLD, malignancy, nephrotoxicity, or cardiovascular disease. Thus, it is appropriate to examine the composite endpoint of subject and graft survival as a summary measure of the net benefit of immunosuppressive therapy in allograft recipients. This composite endpoint has the further advantage of being assessable in all subjects without bias due to missing data or subject misclassification.

Renal function as an endpoint was selected since the relationship between post-transplant renal function and long-term renal outcome has been repeatedly demonstrated in various settings. The association is present whether renal function is measured a few days after transplant, at the time of discharge from the hospital, or at 6 and 12 months following transplant. It has been observed in recipients of kidneys from living and cadaveric donors, in recipients of kidneys from younger and older cadaveric donors, in second transplant recipients, and in adult and pediatric recipients.

Results from multicenter studies confirm the importance of SCr for predicting long-term graft survival. The relationship between renal function and long-term prognosis is strong and reproducible, but not strictly linear. In an analysis of adult renal transplant recipients, examination of the relationship between SCr at 1 year and projected median graft half-life revealed a pronounced inflection point at SCr>1.5 mg/dL.

Similarly, examination of the relationship between change in SCr from 6 months to 1 year ($\Delta$SCr) and projected median graft half-life revealed a pronounced inflection point at $\Delta$SCr$\geq$0.3 mg/dL. Thus, both the absolute level of renal function at 1 year and the change in renal function from 6 months (or a similar stable, early post-transplant time point) to 1 year is suitable for use as outcome measures. The presence of non-linearity in the relationship of renal function to long-term outcome suggests that categorical measures of renal function would be of greater clinical relevance than dimensional ones. Threshold values of >1.5 mg/dL at 1 year for renal function and change in SCr of $\geq$0.3 mg/dL from Month 6 to Year 1 appear appropriate.

In the studies referenced above, the prognostic importance of renal function was demonstrated using SCr as a marker. These studies were in general too large to use direct measures of glomerular filtration. The limitations of SCr as a marker of renal function are well known. SCr levels reflect primarily the balance between renal excretion of creatinine and endogenous generation of creatinine. The latter can be significantly affected by variations in muscle mass, infection, inflammation, and steroid use, which are all common in the transplant population. Moreover, the renal excretion of creatinine can occur by 2 routes—glomerular filtration and tubular secretion. The impact of loss of glomerular filtration on SCr is commonly masked by compensatory increases in tubular secretion, and the utility of increased SCr as a marker of renal impairment is thereby reduced. It has been estimated that 40% of subjects with reduced GFR will have normal or low SCr. Numerous formulae have been developed that seek to improve the correlation between SCr and GFR by accounting for the effect of demographic and biometric factors. The level of agreement between GFR estimated from various formulas and true GFR measured by inulin clearance was studied in 294 transplant recipients with stable renal function. The proportion of predicted GFR values differing from measured inulin clearance by at least 10 mL/min/1.73 m² ranged from 34% for the Jelliffe formula to 53% for the Nankivell formula. The formula proposed by Levey et al will be used to calculate GFR in this study. This formula has been shown to predict GFR more accurately in the transplant population, having the best correlation between predicted and measured value than other formulae, such as Nankivell. Given the substantial difference between true GFR and calculated GFR, clearance of a true glomerular filtration marker will be used to assess the primary endpoint of renal function (Appendix 1). A GFR of 60 mL/min/1.73 m², or change in GFR of at least 10 mL/min/1.73 m², will be used as the approximate equals of the threshold values of SCr of 1.5 mg/dL or change in SCr of at least 0.3 mg/dL established in large epidemiological studies. The change component of the composite endpoint will be assessed from Months 3 to 12, since post-transplant renal function is largely stable by Month 3.

Other Outcome Measures

The key secondary objectives are to evaluate the effects of L104EA29YIg, relative to CsA, on measured GFR at 12 months and on biopsy-proven CAN at 12 months. These endpoints are segregated from other secondary endpoints to emphasize their importance in the evaluation of L104EA29YIg. As discussed above, the functional nephron mass and renal reserve in ECD kidneys are likely to be reduced at the time of transplantation due to donor characteristics (e.g., older age, cardiovascular co-morbidities, procurement procedures, and CIT) with resultant subject and graft survival rates that are well below that observed with standard criteria donor organs. Since renal function is potentially diminished at time of engraftment, it is possible that a substantial proportion of subjects may meet criteria for the co-primary renal function endpoint at the time of study entry or determination of baseline renal allograft function. Accordingly, a key secondary objective of the protocol is to evaluate the effects of L104EA29YIg, relative to CsA, in the difference in measured GFR at 12 months. This key secondary endpoint allows for discernment of the effects of L104EA29YIg, as compared with CsA, irrespective of pre-existing donor variability in this ECD population. It also contributes to the evaluation of renal function in total, and strengthens further the conclusion that L104EA29YIg provides a significant medical benefit in renal transplant recipients. The remaining key secondary objective is the biopsy-proven CAN by 12 months. CAN is second only to death with a functioning graft as the leading cause of late renal allograft loss. Paradoxically, CNIs are thought to contribute to CAN through direct (ie, direct nephrotoxic effects) and indirect pathways (ie, adverse cardiovascular and metabolic effects). Due to its specific mechanism of action, L104EA29YIg is unlikely to be either directly nephrotoxic or adversely alter cardiovascular and metabolic parameters.

In the Example above, favorable effects were seen in the reduced incidence of CAN among L104EA29YIg-treated subjects. In the current study, establishing a decrease in the incidence of CAN, in conjunction with an improvement in renal function, would strengthen the conclusion that L104EA29YIg provides a significant medical benefit in renal transplant recipients. The efficacy of L104EA29YIg in the prevention of acute rejection will be assessed by a variety of outcome measures. These include its incidence, severity, responsiveness to therapy, and outcome. The interpretation of these measures, however, is complicated by intrinsic differences in L104EA29YIg and CsA. L104EA29YIg is administered at the time of transplant, while CsA is initiated once there is evidence of incipient renal function. It is anticipated that a some subjects randomized to CsA in this study will receive a polyclonal antilymphocyte preparation to provide immunosuppressive coverage if initial renal function is impaired and DGF is anticipated. This therapeutic action may prevent or mask the development of acute rejection in CsA-treated subjects and render the subject unevaluable for the outcome measures of acute rejection. Because it is unnecessary to take similar action in subjects randomized to L104EA29YIg—who are treated from the time of transplant—the comparative assessment of acute rejection is unequal. In order to more accurately assess the efficacy of L104EA29YIg in the prevention of acute rejection, the use of polyclonal lymphocyte preparations in this capacity will also be reported in conjunction with other measures of acute rejection.

Study Population

The study population includes recipients of renal allografts that are potentially suboptimal due to donor characteristics, procurement procedure, CIT, or other factors. The specific eligibility criteria are based upon the 'expanded criteria' for organ donation issued by UNOS. Recipients of kidneys from donors with prolonged CIT or from DCDs, will also be eligible. In general, immunological criteria will not play a major role in subject selection. Subjects at varying levels of immunological risk are eligible. The study will, however, exclude subjects of greatest immunological risk (positive cross-match, panel reactive antibodies [PRA] of $\geq$30%, or those previously transplanted). These subjects may require therapy to reduce their antibody load, such as plasmapheresis, which is beyond the scope of this protocol. Subjects will be enrolled at approximately 90 sites globally.

Primary Efficacy Outcome Measures

1.) Evaluate the effects of L104EA29YIg, relative to CsA, on the composite of subject and graft survival at 12 months.

2.) Evaluate the effects of L104EA29YIg, relative to CsA, on the composite of measured GFR<60 mL/min/1.73 $m^2$ at Month 12 or a decrease in measured GFR$\geq$10 mL/min/1.73 $m^2$ from Month 3 to Month 12.

Secondary Efficacy Outcome Measures

1.) Evaluate the effects of L104EA29YIg, relative to CsA, on measured GFR at 12 months.

2.) Evaluate the effects of L104EA29YIg, relative to CsA, on biopsy-proven CAN by 12 months.

3.) Assess the effects of L104EA29YIg, relative to CsA, on measured GFR at 3 months, and change from baseline (3 months) to 12 months.

4.) Assess the effects of L104EA29YIg, relative to CsA, on the proportion of subjects with a measured GFR<30 mL/min/ 1.73 $m^2$ at 12 months.

5.) Assess the effects of L104EA29YIg, relative to CsA, on calculated GFR at 3, 12, 24, and 36 months, and change from baseline (3 months) to 12, 24, and 36 months.

6.) Assess the effects of L104EA29YIg, relative to CsA, on PTDM at 12, 24, and 36 months.

7.) Assess the effects of L104EA29YIg, relative to CsA, on measures of hypertension at 12, 24, and 36 months, including SBP and DBP, incidence and prevalence of hypertension and controlled hypertension, and intensity of treatment regimen.

8.) Assess the effects of L104EA29YIg, relative to CsA, on measures of dyslipidemia, at 12, 24, and 36 months, including serum total, non-HDL, LDL, and HDL cholesterol, and TGs, incidence and prevalence of dyslipidemia and controlled dyslipidemia, and intensity of treatment regimen.

9.) Evaluate the effects of L104EA29YIg, relative to CsA, on subject and graft survival at 24 and 36 months.

10.) Assess the effects of L104EA29YIg, relative to CsA, on measures of acute rejection at 6 months, including the incidence and severity of acute rejection, the use of polyclonal antilymphocyte preparations for impaired renal function and anticipated DGF, the initial use of lymphocyte-depleting therapy for treatment of acute rejection, the incidence of steroid-resistant acute rejection, the incidence of complete recovery (SCr returning to baseline) following acute rejection, the incidence of subclinical rejection, and the incidence of all treated acute rejection episodes regardless of histological findings.

11.) Evaluate the effects of L104EA29YIg, relative to CsA, on QoL 10)Assess the overall safety of L104EA29YIg, relative to CsA.

Tertiary Outcome Measures

1.) Assess the effects of L104EA29YIg, relative to CsA, on the slope and intercept of calculated GFR from baseline (3 months) to 12, 24, and 36 months.

2.) Assess the effects of L104EA29YIg, relative to CsA, on the proportion of subjects with a measured GFR<45 mL/min/ 1.73 $m^2$ at 12 months.

3.) Assess the effects of L104EA29YIg, relative to CsA, on the proportion of subjects with <75 mL/min/1.73 $m^2$ calculated GFR at Month 12 and subjects with a decrease in calculated GFR from Month 3 to Month 12 of at least 15 mL/min/1.73 $m^2$.

4.) Assess the effects of L104EA29YIg, relative to CsA, on the incidence of DGF.

5.) Assess the effects of L104EA29YIg, relative to CsA, on measures of acute rejection at 12, 24, and 36 months, including the incidence and severity of acute rejection, the use of polyclonal antilymphocyte preparations for impaired renal function and anticipated DGF, the initial use of lymphocyte-depleting therapy for treatment of acute rejection, and the incidence of steroid-resistant acute rejection, the incidence of complete recovery (SCr returning to baseline) following acute rejection, the incidence of subclinical rejection, and the incidence of all treated acute rejection episodes regardless of histological findings.

6.) Assess the effects of L104EA29YIg, relative to CsA, on a composite cardiovascular disease endpoint (adjudicated cardiovascular death, myocardial infarction, ischemic stroke, non-elective hospitalization for cardiovascular cause, and percutaneous coronary intervention) at 12, 24, and 36 months.

7.) Assess the effects of L104EA29YIg, relative to CsA, on a composite cardiorenal disease endpoint (death, graft loss, non-fatal myocardial infarction, and stroke) at 12, 24, and 36 months.

8.) Assess the effects of L104EA29YIg, relative to CsA, on the Framingham Risk Score at 12, 24, and 36 months.

9.) Assess the effects of L104EA29YIg, relative to CsA, on incidence of discontinuation of study drug.

10.) Assess the effects of L1I04EA29YIg, relative to CsA, on anti-donor HLA antibodies.

11.) Assess the effects of L104EA29YIg, relative to CsA, on C4d positivity in biopsy specimens.

Definition of Graft Loss Graft loss is defined as either functional loss or physical loss. Functional loss will be defined as a sustained level of SCr≧6.0 mg/dL (530 (mol/L) as determined by the central laboratory for ≧4 weeks or ≧56 consecutive days of dialysis, or impairment of renal function to such a degree that the subject received a second transplant. All causes of graft loss will be adjudicated by an independent EAC.

Definition of Delayed Graft Function (DGF) DGF is defined as treatment with dialysis by study Day 8 (postoperative Day 7).

Definition of Chronic Allograft Nephropathy (CAN) Biopsy-proven CAN will be determined by a blinded central histopathologist using the Banff 97 working classification of kidney transplant pathology. The incidence of CAN will be determined by comparing all post-Day 1 biopsies to baseline biopsies obtained at the time of transplant. This comparison establishes the presence and severity of any preexisting histopathology that may be later interpreted as CAN.

Definition of Post-transplant Diabetes Mellitus PTDM will be defined according to the definition set forth by a recent international consensus guideline.20 These criteria are summarized as: a)Symptoms of diabetes plus casual plasma glucose (PG) concentration ≧200 mg/dL (11.1 mmol/L) OR b)fasting plasma glucose (FPG) ≧126 mg/dL (7.0 mmol/L) OR c)2-hour PG≧200 mg/dL (11.1 mmol/L) during an oral glucose tolerance test AND d) a confirmatory laboratory test based on measurements of venous PG must be done on another day in the absence of unequivocal hyperglycemia accompanied by acute metabolic decompensation. The study will utilize FPG for evaluation of PTDM, however, if subjects are evaluated using these other methods and found to meet the above criteria, they will be considered as having PTDM.

Definition of Measures of Hypertension Hypertension will be as defined in this study according to the Seventh Report of the Joint National Committee on the Prevention, Detection, Evaluation, and Treatment of High Blood Pressure21 for subjects with chronic kidney disease. This definition is based upon SBP≧130 mm Hg or DBP≧80 mm Hg. In addition, all subjects who have a SBP<130 mm Hg and a DBP<80 mm Hg who are receiving an antihypertensive medication(s) for the indication of hypertension or with a medical history of hypertension are included in this definition. The incidence of hypertension is defined as the proportion of subjects who develop hypertension after randomization and transplantation. The prevalence of hypertension is defined as the proportion of subjects at any given time who meet the above stated definition of hypertension. Controlled hypertension is defined as a SBP<130 mm Hg and a DBP<80 mm Hg while receiving an antihypertensive medication for the indication of hypertension or receiving an antihypertensive medication for another indication with a medical history of hypertension. Subjects with a SBP<130 mm Hg and a DBP<80 mm Hg who are prescribed an antihypertensive medication(s) for an indication(s) of other than hypertension (e.g., beta blockers for migraine prophylaxis) with no medical history of hypertension will not be considered to have either hypertension or controlled hypertension. Intensity of treatment regimen is defined as the total number of antihypertensive medications used to control hypertension. All antihypertensive medications will be counted for the indication of hypertension in subjects with hypertension or controlled hypertension since the antihypertensive effects are present irrespective of indication.

Definition of Measures of Dyslipidemia Dyslipidemia is defined in accordance with recent guidelines from the National Kidney Foundation Kidney Disease Outcomes Quality Initiative (NKF-K/DOQI).22 Dyslipidemia is defined as hypertriglyceridemia (TGs ∈500 mg/dL [5.65 mmol/L]), hypercholesterolemia (LDL ∈100 mg/dL [2.59 mmol/L]), or elevated non-HDL (non-HDL ∈130 mg/dL [3.36 mmol/L]) in the presence of high TGs (TGs ∈200 mg/dL [2.26 mmol/L Controlled dyslipidemia is defined in this study as subjects who are receiving pharmacological management for one of the above stated dyslipidemias that is successfully treated, and their lipid values fall below the thresholds described in the previous paragraph. Some of these agents have specific precautions and/or warnings regarding the starting dose or maximal recommended dose with concomitant use of CsA, dosing with renal insufficiency, or may cause alterations of CsA PK. Refer to the appropriate package insert for specific recommendations. Any other agent (ie, non-statin therapy) used as an antihyperlipidemic will be considered Level I treatment intensity. Concomitant use of a statin and an agent of another class (e.g., ezetimibe) will elevate the intensity level of the statin therapy by 1 level; therefore, more than 5 intensity levels are possible.

Acute rejection will be defined as a clinico-pathological event requiring clinical evidence and biopsy confirmation. Allograft biopsies will be evaluated for the presence and severity of acute rejection by a blinded central independent pathologist using Banff 97 working classification of kidney transplant pathology. In the analyses of acute rejection the biopsy interpretation and grading by the central pathologist will supersede local interpretation. Biopsies performed for suspected acute rejection that do not fully meet the criteria, but are interpreted by the central pathologist as acute rejection and result in treatment for acute rejection, will be counted as acute rejection. Subclinical rejection is defined as histological findings by the central pathologist consistent with acute rejection, but lacking its clinical correlate. Steroid-resistant acute rejection is defined as lack of improvement in the SCr and/or histological findings that necessitate the use of lymphocyte-depletion therapy following treatment with corticosteroids. Framingham Risk Score This risk score utilizes data from the Framingham Heart Study23 to estimate 10-year risk for 'hard' coronary heart disease (myocardial infarction and coronary death). The risk factors included in this calculation are age, gender, total cholesterol, HDL cholesterol, SBP, diabetes, treatment for hypertension, and any cigarette use in the prior month.

Sample Size Determination

The primary objective is to estimate the effect of L104EA29YIg on subject and graft survival rates and renal function at 12 months as compared to CsA. The 2 co-primary endpoints are: (1) the proportion of subjects with a surviving graft at 12 months post-transplantation and (2) the proportion of subjects whose measured GFR at 12 months is <60 mL/min/1.73 m$^2$, and/or whose measured GFR decreased $\geq$10 mL/min/1.73 m$^2$ from Month 3 to Month 12. A sample size of 180 subjects per treatment group will afford 83% power to ascertain that the upper bound of the 97.3% 2-sided CIs for the absolute difference (between each L104EA29YIg regimen and the CsA regimen) in the first co-primary endpoint (subject and graft survival) will not exceed 10%, if the true subject and graft survival rate at 12 months is 80% for the CsA regimen and 83% for each of the 2 L104EA29YIg regimens. For the renal function endpoint, the sample size of 180 subjects per group is powered to detect a decrease of 25% in the proportion of subjects meeting the measured GFR endpoint for each L104EA29YIg regimen as compared with the CsA regimen, assuming 75% of CsA subjects meet the renal function endpoint and 25% drop-outs per treatment group. Overall, 180 subjects per treatment group will afford at least 80% power to detect 1 L104EA29YIg regimen that meets both co-primary endpoints with overall Type I error controlled at the 0.05 significance level (Dunnett adjustment).

Inclusion Criteria

Target Population: 1) The subject is a first-time recipient of a deceased donor kidney transplant 2) The donor and/or donor kidney meet at least 1 of the following extended criteria for organ donation: a) Donor age$\geq$60 years OR b) Donor age 50-59 years and 1 of the following: (i) Cerebrovascular accident (CVA)+hypertension+SCr>1.5 mg/dL OR (ii) CVA+hypertension OR (iii)CVA+SCr>1.5 mg/dL OR (iv) Hypertension+SCr>1.5 mg/dL OR c) CIT$\geq$24 hours, donor age>10 years OR d) Donor with cardiac death (non-heart beating donor) 3) Men and women, ages 18 and older, inclusive 4) WOCBP must be using an adequate method of contraception to avoid pregnancy throughout the study and for up to 8 weeks after the study in such a manner that the risk of pregnancy is minimized WOCBP includes any female who has experienced menarche and who has not undergone successful surgical sterilization (hysterectomy, bilateral tubal ligation, or bilateral oophorectomy) or is not postmenopausal (defined as amenorrhea$\geq$12 consecutive months; or women on hormone replacement therapy with documented serum follicle stimulating hormone level>35 mIU/mL). Even women who are using oral, implanted, or injectable contraceptive hormones or mechanical products such as an intrauterine device or barrier methods (diaphragm, condoms, spermicides) to prevent pregnancy or practicing abstinence or where the partner is sterile (e.g., vasectomy), should be considered to be of child bearing potential. WOCBP must have a negative serum pregnancy test (minimum sensitivity 25 IU/L or equivalent units of human chorionic gonadotropin [HCG]) within 72 hours prior to the start of study medication. 5) Men must use an adequate method of contraception throughout the study, and for up to 8 weeks after the last infusion, so that the risk of pregnancy to their partners is minimized.

Exclusion Criteria

1) WOCBP who are unwilling or unable to use an acceptable method to avoid pregnancy for the entire study period and for up to 8 weeks after the last infusion. 2) Women who are pregnant or breastfeeding 3) Women with a positive pregnancy test on enrollment or prior to study drug administration 4) Males unwilling or unable to use an adequate method of contraception for the entire study period and for up to 8 weeks after the last infusion of study medication 5) Donor age<10 years 6) Subjects with underlying renal disease of: a) Focal segmental glomerulosclerosis (biopsy proven) b) Type I or II membranoproliferative glomerulonephritis c) Hemolytic uremic syndrome/thrombotic thrombocytopenic purpura syndrome 7) Subjects with current PRA$\geq$30% 8) Subjects with a positive T-cell lymphocytotoxic crossmatch 9) Subjects with any prior solid organ transplant (including kidney) 10) Subjects receiving a concurrent solid organ (heart, liver, pancreas) or cell (islet, bone marrow, stem cell) transplant 11) Subjects receiving paired kidneys from the extended criteria donor (dual kidney transplant) 12) Subjects who are hepatitis C antibody-positive or polymerase chain reaction (PCR)-positive for hepatitis C 13) Subjects who are hepatitis B surface antigen-positive or PCR-positive for hepatitis B 14) Subjects with known human immunodeficiency virus (HIV) infection 15) Subjects with active tuberculosis (TB) requiring treatment within the previous 3 years or any subject who previously required triple (or more) combination therapy for TB. Subjects with a known positive purified protein derivative (PPD) will not be eligible for the study unless they completed treatment for latent TB and have a negative chest x-ray at the time of enrollment. PPD testing done within the last 12 months is acceptable as long as there is documentation of the results. Subjects without a PPD in the last 12 months who have a previous negative result may be enrolled if they also have a negative chest x-ray at enrollment, no symptoms indicative of TB, no known TB contacts, not currently residing in, recently traveled to, or previously immigrated from an area endemic for TB. A PPD response that is $\geq$10 mm induration or a Heaf score of >1 in non-Bacille Calmette-Guérin (non-BCG) immunized subjects or >2 in BCG immunized subjects should be considered a positive test. More conservative criteria may be applied according to the published guidelines and/or local standards endorsed by the medical society 16) Subjects with any active infection or other contraindication that would normally exclude transplantation 17) Subjects whose life expectancy is severely limited by disease state or other underlying medical condition 18) Subjects with a history of cancer (other than non-melanoma skin cell cancers cured by local resection) within the last 5 years 19) Subjects with a history of substance abuse (drug or alcohol) within the past 5 years, or psychotic disorders that are not compatible with adequate study follow-up 20) Subjects with active peptic ulcer disease, chronic diarrhea, or gastrointestinal malabsorption 21) Subjects with local laboratory values that are Common Toxicity Criteria (CTC) Grade II or greater may not participate in the study. However, certain specified laboratory parameters that are exceptions to CTC Grade II will be allowed. The following allowances are noted: Hematology: Hemoglobin may be below CTC Grade II (but not below 8 g/dL) Platelets may be below CTC Grade II, but not below 80,000/mm3 (80×109/L) Total white cell blood (WBC) count may be below CTC Grade II, but not below 3000/mm3 (3×109/L) Granulocyte and lymphocyte counts may be any value Chemistry: SCr and blood urea nitrogen (BUN) values may be any value Blood glucose may be of any value Urinalysis. Urinalysis results may be any value 22) All women 40 years or older and women of any age who have first degree relatives with a history of breast carcinoma or who have other risk factors of breast carcinoma, must have a screening mammogram, or provide results of a screening mammogram performed within 6 months of enrollment. Subjects with a mammogram that is suspicious for malignancy and in whom the possibility of malignancy cannot be reasonably excluded following additional clinical, laboratory, or other diagnostic evaluations will be excluded. If the screening mammogram was not performed within 6 months of enrollment, but the subject is deemed a suitable transplant candidate by local criteria, the baseline mammogram may be obtained within 4 weeks after transplant 23) Subjects who have difficult i.v. access or other reasons that would likely preclude assessment of the co-primary endpoint of measured GFR or subjects that are unlikely (e.g., due to preexisting coagulation issues) or unwilling to undergo the protocol specified 12-month allograft biopsy 24) Subjects with a history of true allergy to i.v. iodinated x-ray contrast agents 25) Subjects who have used any investigational drug within 30 days prior to the Day 1 visit 26) Subjects previously treated with L104EA29YIg 27) Prisoners or subjects who are compulsorily detained (involuntarily incarcerated) for treatment of either a psychiatric or physical (e.g., infectious disease) illness must not be enrolled into this study.

Administration of L104EA29YIg

Day 1 is defined as the day of transplant (post-transplant Day 0). Infusion of the Day 1 dose should begin after the surgeon has made an initial intraoperative assessment, and has concluded that the subject remains a transplant candidate and the transplant will proceed, and before beginning the transplant vascular anastomoses. Infusion doses will be based on the subject's actual body weight at study Day 1, and will not be modified during the course of the study, unless there is a change of body weight±10%. Study drug should be administered to the subject at a relatively constant rate over 30 minutes. The Day 1 and Day 5 (post-transplant Day 4) doses should be administered approximately 96 hours apart (±6 hours). Subsequent visit and infusion windows are provided below. For subjects on dialysis, infusion of L104EA29YIg and determination of the subject's weight should occur after dialysis treatment.

L104EA29YIg MI Regimen: Subjects randomized to the MI regimen will receive i.v. L104EA29YIg (10 mg/kg) on Days 1 and 5, and then every other week for 2 months (Weeks 2, 4, 6, 8, 10, and 12), and then every 4 weeks until 6 months (Weeks 16, 20, and 24). After 6 months, subjects in the MI treatment group will receive L104EA29YIg at the maintenance dose of 5 mg/kg every 4 weeks until completion of the trial at 36 months.

L104EA29YIg LI Regimen: Subjects randomized to the LI regimen will receive i.v. L104EA29YIg (10 mg/kg) on Days 1 and 5, and then every other week for 2 weeks (Weeks 2 and 4), and then every 4 weeks for 2 months (Weeks 8 and 12). After 3 months, subjects in the LI treatment group will receive L104EA29YIg at the maintenance dose of 5 mg/kg every 4 weeks until completion of the trial at 36 months. Blinding between the LI and MI group will be preserved with the use of 2 placebo infusions in the LI treatment group. Therefore, subjects randomized to the LI regimen will be administered placebo (dextrose 5% in water for injection [D5W]) infusions on Weeks 6 and 10.

Administration of Cyclosporine (CsA)

The daily dose of CsA should be administered in 2 divided doses on a consistent schedule in relation to time of day and meals. On study visit days, the subject must withhold the morning CsA dose until after trough CsA blood level draws. On study visit days, when the subject is to have standardized BP monitoring and/or measured GFR assessments, these measures are to be completed prior to CsA dosing. The initial daily dose should be 7±3 mg/kg (ie, 4-10 mg/kg). Subsequent doses should be adjusted to maintain a predefined range of trough serum concentrations: 1st month: target level 150-300 ng/mL After 1st month: target level of 100-250 ng/mL. Monitoring of CsA levels using the plasma concentration 2 hours post-dose (C2) is not to be used in this study. While a recent international consensus statement on management of Neoral by C2 monitoring favored the use of C2 monitoring, it also clearly stated the lack of data regarding the long-term effects on renal function, incidence of CAN, and general safety profile associated with C2 monitoring.24 Furthermore, not all subjects are suitable for C2 monitoring, including subjects with diabetes, slow gastric emptying, or subjects using concomitant medication that alters CsA clearance. Moreover, low C2 levels may result from either true low absorption (in which the CsA dose should be increased) or from slow absorption (in which there is a delayed maximum plasma concentration and an increase in dose may produce toxicity). Finally, this practice is not universal, and prospectively validating this practice is beyond the scope of the current protocol. For additional prescribing information, see the package insert. CsA should be initiated in all subjects by Day 7. For subjects in whom the investigator believes that it is not in the best interest of the subject to initiate CsA at all (e.g., due to impaired renal function), and elects to use a non-study medication (e.g., sirolimus) instead, this action will be considered a discontinuation of study medication.

For Subjects with Immediate Allograft Function: For subjects randomized to treatment with CsA, the first dose of CsA should be administered as soon as, but not until, there is evidence of adequate allograft function. Adequate allograft function is defined as a decrease in the SCr of at least 1 mg/dL compared to the initial post-transplant value or urine output ≧250 mL in a 12 hour (or less) period post-transplant.

For Subjects with Impaired Renal Allograft Function and Anticipated DGF: Subjects with postoperative impaired allograft function and anticipated DGF are eligible—but not required—to receive a polyclonal antilymphocyte preparation. Whether a subject receives a polyclonal lymphocyte preparation or not, CsA should be initiated when there is evidence of recovery of allograft function (as defined above) or by Day 7.

Corticosteroids

All subjects in this study will be treated with daily corticosteroids.

Steroid Maintenance—Taper Day of transplant (Day 1): methylprednisolone (as sodium succinate) 500 mg i.v. on arrival in the operating room (OR)

Day 2: methylprednisolone (as sodium succinate) 250 mg i.v:

Day 3: prednisone (or prednisolone) 100 mg orally (p.o.)

Day 4 through Day 14 (ie, end of Week 2): taper prednisone (or prednisolone) to 20-30 mg p.o. daily Day 15 through Month 6: taper prednisone (or prednisolone) no lower than 2.5 mg p.o. daily Subjects must remain on at least 2.5 mg p.o. daily through Year 3.

The first 2 doses (study Day 1, day of transplant and study Day 2, post-operative Day 1) are to be administered i.v. The remaining doses are to be administered p.o. However, i.v. dosing of an equivalent dose of methylprednisolone is permitted at times when oral dosing is not possible. Such reasons for i.v. rather than p.o. dosing are intercurrent illness, postoperative ileus, or other causes at the investigator's discretion. If methylprednisolone is not available, the use of another i.v. corticosteroid agent dose-equivalent to methylprednisolone is permitted.

Mycophenolate Mofetil Dosing

All subjects in this study will be treated with MMF. Daily MMF should be administered in 2 divided doses on a consistent schedule in relation to time of day and meals. The dose should be 2 g daily; however, in African Americans, 3 g daily may be administered at the investigator's discretion.25 MMF should be administered p.o. Intravenous dosing is permitted, if needed due to intercurrent illness, postoperative ileus, or other causes at the investigator's discretion. The first dose should be administered preoperatively. Subsequent doses should be administered p.o. as soon as the subject is able to tolerate medications by mouth. The dose and schedule may be adjusted determined on the basis of laboratory values (e.g., decreased WBCs) and subject tolerability (see below). For full prescribing information, see the package insert.

For subjects who develop nausea, diarrhea, or other MMF-related gastrointestinal adverse effects (e.g., symptoms fully assessed and deemed not to have an etiology other than intolerability to MMF), the MMF dose may be decreased to the maximally tolerated dose. For subjects who develop neutropenia (absolute neutrophil count $<1.3\times103/\text{fL}$), dosing with MMF should be interrupted or dose reduced as per the package insert.

Basiliximab Dosing

All subjects in this study will be treated with the recommended dosing regimen of basiliximab. Basiliximab should be administered through a peripheral or central vein only. Reconstituted basiliximab (20 mg in 5 mL) should be diluted to a volume of 50 mL with normal saline or dextrose 5% and administered as an i.v. infusion over 20-30 minutes. The first 20 mg dose should be administered on Day 1 (the day of transplantation; post-operative Day 0). For subjects randomized to L104EA29YIg, this first basiliximab infusion should occur as soon as possible after completion of the L104EA29YIg infusion. The second 20 mg dose should be given on Day 5 (post-operative Day 4). The second basiliximab dose should not be administered to subjects if they have received or are expected to receive a lymphocyte-depleting treatment. For additional information, see the package insert.

Polyclonal Antilymphocyte Preparations for Impaired Renal Allograft Function and Anticipated DGF The use of polyclonal antilymphocyte preparations (Thymoglobulin or ATGAM) is permitted—but not required—for subjects randomized to CsA who experience impaired renal allograft function and anticipated DGF following transplantation. Use of other polyclonal antilymphocyte preparations or polyclonal antithymocyte globulins is permitted in regions where market authorization exists, and if they are indicated for the treatment of acute rejection in renal transplantation. Of note, OKT3 is not to be used for this purpose, but may be used for treatment of Banff 97 Grade IIb or greater acute rejection or steroid-resistant acute rejection. Use of Campath 1-H® (alemtuzumab) is not permitted in this protocol, as it is not indicated for use in kidney transplantation. These agents are widely utilized in this capacity to afford immunosuppression until graft function allows for administration of CsA . Therefore, polyclonal antilymphocyte preparations may be used in this clinical setting, at the investigator's discretion, in subjects who meet $\geq$ of the following criteria that are observed in the presence of a patent transplant artery and vein and no evidence of hydronephrosis by sonogram: a)Urine output <250 cc/12 hours b)No significant improvement (<1 mg/dL) in SCr from baseline value over the first 24-72 hours post-transplant c)Dialysis treatment. Use of these agents for impaired renal allograft function and anticipated DGF is not permitted in L104EA29YIg-treated subjects.

Sulfamethoxazole/Trimethoprim Dosing

All subjects who participate in this study who have no contraindications should receive sulfamethoxazole/trimethoprim prophylaxis to prevent urinary tract and *Pneumocystis carinii* infections. Dosing and administration are to be determined by the level of renal function consistent with the package insert. Subjects with a contraindication or intolerance to sulfa drugs. or trimethoprim may receive prophylactic therapy with inhaled pentamidine at the investigator's discretion. For full prescribing information, see the package inserts.

Valganciclovir/Ganciclovir, Acyclovir/Valacyclovir Dosing

All recipients who have no contraindications to valganciclovir, ganciclovir, acyclovir, and valacyclovir should be prophylactically treated with these drugs to prevent infections due to CMV and Herpes simplex. The following are guidelines for dosing and duration of prophylactic treatment:

Prophylaxis for the First 10 Days Post-transplant or During T-cell-depleting Therapy: All transplant subjects will receive valganciclovir or ganciclovir per protocol for 10 days after surgery. If treated with T-cell-depleting therapy for induction therapy or treatment for acute rejection, the subject will receive valganciclovir or ganciclovir for the duration of the T-cell-depleting therapy. If the subject is discharged prior to 10 days, either oral valganciclovir, ganciclovir, valacyclovir, or acyclovir will begin based on CMV immune status as described below.

Valganciclovir for Prophylaxis: Creatinine Clearance $\geq$60 mL/min, dose 900 mg daily; Creatinine Clearance 40-59 mL/min, dose 450 mg daily; Creatinine Clearance <40 mL/min, dose 450 mg every other day.

Ganciclovir for Prophylaxis: If the subject is unable to tolerate oral medications, or valganciclovir is not available for use, ganciclovir suspension or capsules may be substituted. Creatinine Clearance $\geq$70 mL/min, dose 1 g 3 times daily; Creatinine Clearance 50-69 mL/min, dose 500 mg 3 times daily; Creatinine Clearance 25-49 mL/min, dose 500 mg twice daily; Creatinine Clearance 10-24 mL/min, dose 500 mg daily; Creatinine Clearance <10 mL/min, dose 500 mg after hemodialysis 3 times/week. If i.v. ganciclovir is needed, see the package insert for dosing.

Prophylaxis After 10 Days Post-transplant Through at Least 3 Months: CMV Antibody Seropositive Donor to a CMV Antibody Seronegative Recipient: Continue valganciclovir or ganciclovir protocol listed above for $\geq$3 months.

CMV Antibody Seropositive or Seronegative Donor to a CMV Antibody Seropositive Recipient: Oral acyclovir for $\geq$3 months post-transplantation: Serum Creatinine $\geq$50 mL/min, dose 800 mg orally 4 times daily; Serum Creatinine 25-49 mL/min, dose 800 mg orally 3 times daily; Serum Creatinine 11-24 mL/min, dose 800 mg orally twice daily; Serum Creatinine <10 mL/min, dose 800 mg orally daily; On hemodialysis, dose 800 mg daily after hemodialysis Valacyclovir may be substituted for acyclovir at the time of discharge for subject convenience. Serum Creatinine$\geq$50 mL/min, dose 500 mg orally 2 times daily; Serum Creatinine 25-49 mL/min, dose 500 mg orally daily; Serum Creatinine 11-24 mL/min, dose 250 mg orally daily; Serum Creatinine <10 mL/min, dose 250 mg orally daily; On hemodialysis, dose 250 mg daily after hemodialysis CMV Antibody Seronegative Donor to a CMV Antibody Seronegative Recipient: Oral Acyclovir Protocol Needed for Herpes Prophylaxis Only: continue for ≧3 months post-transplantation. Acyclovir 400 mg p.o. twice daily or valacyclovir may be substituted for acyclovir at the time of discharge for subject convenience. For full prescribing information, refer to the package inserts.

Infusion-only Visit Procedures a) For subjects randomized to L104EA29YIg treatment: A negative pregnancy test is required prior to L104EA29YIg administration. The dose is to be based on the subject's weight at the most recent previous study visit. Subjects should be monitored for vital signs (pre- and post-infusion), and AEs should be assessed. PK samples may be required at some visits.

b) For subjects randomized to CsA treatment: Subjects shall be contacted to assess for AEs only. This visit can be a telephone contact, and should occur within the prescribed visit window for the specified visit.

Visit Windows a) For subjects randomized to L104EA29YIg treatment: the Days 1 and 5 doses should be administered approximately 96 hours apart(±6 hours). To facilitate scheduling the infusion-only visits, the following windows are permitted for subsequent doses: Visit Week 2, Visit Window target date±2 days; Visit Week 4-Month 6 Visit Window target date±3 days, Visit Month 7-Month 36, Visit Window target date±5 days; Visit follow-up 8 weeks, Visit Window target date±5 days.

b) For subjects randomized to CsA treatment: After Day 5, subjects are only required to attend clinic visits at Weeks 2, 4, 8, and 12; then at every 3-month interval visit. At the non-3-month interval visits (ie, Weeks 6, 10, 16, 20, 28, 32, etc), a telephone contact will be conducted to collect AE information. Clinic and contact visits shall occur within the same visit windows as specified above for subjects randomized to L104EA29YIg. The target dates for the 3- and 12-month GFR assessments are Week 12±14 days and Week 52±14 days. Under certain circumstances, and with the prior approval of the medical monitor, the measured GFR assessments at Month 3 and Month 12 may be conducted through Month 6 and Month 15, respectively. Such reasons that may warrant extension of a measured GFR assessment include the presence of a concurrent acute rejection episode or the need to repeat an assessment for technical reasons.

The target date for the 12-month allograft biopsy is Week 52±14 days. Similarly, under certain circumstances and with the prior approval of the medical monitor, the allograft biopsy may be obtained through Month 15. Such reasons that may warrant extension of an allograft biopsy include temporary need for anticoagulation.

Example 5

One knowledgeable in the art could utilize the administration schedule described in Example 4 above to design a study comprising a different study population, donor criteria and/or objectives. For example, this transplant study will evaluate subjects receiving a kidney transplant from a living donor or deceased donor with anticipated cold-ischemic time <24 hours. Subjects at varying levels of immunological risk will be eligible. However, the study will exclude subjects of greatest immunological risk. Subjects will be randomized to the MI, LI or CsA arms as described above in Example 4.

Primary Objectives

Evaluate the effects of L104EA29YIg, relative to CsA, on the composite of subject and graft survival by 12 months. Evaluate the effects of L104EA29YIg, relative to CsA, on the composite of measured GFR<60 mL/min/1.73 m$^2$ at Month 12 or a decrease in measured GFR≧10 mL/min/1.73 m$^2$ from Month 3 to Month 12. Evaluate the effects of L104EA29YIg, relative to CsA, on the incidence of acute rejection by 12 months.

Secondary Objectives

Evaluate the effects of L104EA29YIg, relative to CsA, on measured GFR at 12 months. Evaluate the effects of L104EA29YIg, relative to CsA, on biopsy-proven CAN at 12 months. Assess the effects of L104EA29YIg, relative to CsA, on the individual components of the primary composite endpoint of measured GFR<60 mL/min/1.73 m$^2$ at Month 12 or a decrease in measured GFR≧10 mL/min/1.73 m$^2$ from Month 3 to Month 12. Assess the effects of L104EA29YIg, relative to CsA, on the triple composite endpoint of death, graft loss, and acute rejection by 12, 24, and 36 months. Assess the effects of L104EA29YIg, relative to CsA, on the proportion of subjects with a measured GFR<60 mL/min/1.73 m$^2$ at 24 months Assess the effects of L104EA29YIg, relative to CsA, on measured GFR at 3 and 24 months, and change from baseline (3 months) to 12 months and to 24 months. Assess the effects of L104EA29YIg, relative to CsA, on the proportion of subjects with a measured GFR<30 mL/min/1.73 m$^2$ at 12 and 24 months. Assess the effects of L104EA29YIg, relative to CsA, on calculated GFR at 6, 12, 24, and 36 months, and change from 6 months to 12, 24, and 36 months. Assess the effects of L104EA29YIg, relative to CsA, on PTDM by 12, 24, and 36 months. Assess the effects of L104EA29YIg, relative to CsA, on measures of hypertension at 12, 24, and 36 months, including SBP and DBP, incidence and prevalence of hypertension and controlled hypertension, and intensity of treatment regimen. Assess the effects of L104EA29YIg, relative to CsA, on measures of dyslipidemia, at 12, 24, and 36 months, including serum total, non-HDL, low-density lipoprotein (LDL), and HDL cholesterol, and TGs, incidence and prevalence of dyslipidemia and controlled dyslipidemia, and intensity of treatment regimen. Evaluate the effects of L104EA29YIg, relative to CsA, on subject and graft survival by 24 and 36 months. Assess the effects of L10$^4$EA29YIg, relative to CsA, on the proportion of subjects with a calculated GFR<60 mL/min/1.73 m$^2$ at 24 and 36 months. Assess the effects of L104EA29YIg, relative to CsA, on measures of acute rejection by 6, 12, 24, and 36 months, including the incidence and severity of acute rejection, the use of polyclonal antilymphocyte preparations for impaired renal function and anticipated delayed graft function (DGF), the initial use of lymphocyte-depleting therapy for treatment of acute rejection, the incidence of steroid-resistant acute rejection, the incidence of complete recovery (SCr returning to baseline) following acute rejection, the incidence of subclinical rejection, the incidence of all treated acute rejection episodes regardless of histological findings, and the time to onset of acute rejection. Evaluate the effects of L104EA29YIg, relative to CsA, on QoL. Assess the overall safety of L104EA29YIg, relative to CsA. Assess the effects of L104EA29YIg, relative to CsA, on the slope and intercept of calculated GFR from 3 months to 12, 24, and 36 months. Assess the effects of L104EA29YIg, relative to CsA, on the proportion of subjects with <60 mL/min/1.73 m$^2$ calculated GFR at Month 12 or subjects with a decrease in calculated GFR from Month 3 to Month 12 of at least 10 mL/min/1.73 m$^2$. Assess the effects of L104EA29YIg, relative to CsA, on the incidence of DGF. Assess the effects of L104EA29YIg, relative to CsA, on the proportion of subjects with Stage 1 through Stage 5 chronic kidney disease at 12 and 24 months as assessed by measured GFR. Assess the effects of L104EA29YIg, relative to CsA, on the proportion of subjects with Stage 1 through Stage 5 chronic kidney disease at 36 months as assessed by calculated GFR. Assess the effects of L104EA29YIg, relative to CsA, on a composite cardiovascular disease endpoint (adjudicated cardiovascular death, myocardial infarction, ischemic stroke, and revascularization [surgical or percutaneous] procedures) by 12, 24, and 36 months. Assess the effects of L104EA29YIg, relative to CsA, on a composite cardiorenal disease endpoint (death, graft loss, non-fatal myocardial infarction, and stroke) by 12, 24, and 36 months. Assess the effects of L104EA29YIg, relative to CsA, on the Framingham Risk Score at 12, 24, and 36 months. Assess the effects of L104EA29YIg, relative to CsA, on incidence of discontinuation of study drug. Assess the effects of L104EA29YIg, relative to CsA, on anti-donor human leukocyte antigen (HLA) antibodies. Assess the effects of L104EA29YIg, relative to CsA, on angiotensin II type 1 (ATI1)-receptor antibodies Assess the effects of L104EA29YIg, relative to CsA, on C4d positivity in biopsy specimens Study Design The duration of the study is 3 years with a subsequent 8-week follow-up period for safety evaluations. This is a randomized, partially-blinded, active-controlled, parallel-group study. All subjects will receive a kidney transplant from a living donor or a deceased donor with an anticipated CIT <24 hours.

Approximately 660 subjects will be randomized in a 1:1:1 ratio to treatment with either L104EA29YIg (MI regimen), L104EA29YIg (LI regimen), or CsA. All subjects will also receive induction with basiliximab and a background maintenance immunosuppressive regimen of MMF and corticosteroids. Subjects randomized to the MI regimen will receive i.v. L104EA29YIg (10 mg/kg) on Days 1 and 5, then every 2 weeks through Month 3 (Weeks 2, 4, 6, 8, 10, and 12), and then every 4 weeks through 6 months (Weeks 16, 20, and 24). After 6 months, subjects in the MI treatment group will receive the maintenance dose of L104EA29YIg 5 mg/kg administered every 4 weeks until completion of the trial at 36 months. Subjects randomized to the LI regimen will receive i.v. L104EA29YIg (10 mg/kg) on Days l and 5, and then every 2 weeks through Month 1 (Weeks 2 and 4), and every 4 weeks through Month 3 (Weeks 8 and 12). After 3 months, subjects in the LI treatment group will receive the maintenance dose of L104EA29YIg 5 mg/kg administered every 4 weeks until completion of the trial at 36 months. Blinding between the LI and MI groups will be preserved with the use of placebo infusions in the LI treatment group on Weeks 6 and 10. Subjects randomized to CsA will receive doses twice daily that are designed to achieve a specified trough serum concentration range consistent with current medical practice. The safety and efficacy of L104EA29YIg will be assessed at 1, 2, and 3 years. An independent DSMB will review data from the study on an ongoing basis, and make recommendations for altering the conduct of the trial, if necessary.

Study Population

The study population includes recipients of renal allografts from living donors or deceased donors with an anticipated CIT<24 hours. In general, immunological criteria will not play a major role in subject selection. Subjects at varying levels of immunological risk are eligible. The study will, however, exclude subjects of greatest immunological risk (positive cross match, current panel reactive antibodies [PRA] of 250%, or those previously transplanted with a current PRA ≧30%). These subjects may require therapy to reduce their antibody load, such as plasmapheresis, which is beyond the scope of this protocol. Subjects will be enrolled at approximately 100 sites globally.

Inclusion Criteria

Target Population: 1) The subject is a recipient of a living donor or deceased donor kidney transplant with an anticipated CIT<24 hours 2) Men and women, ages 18 and older, inclusive 3) WOCBP must be using an adequate method of contraception to avoid pregnancy throughout the study and for up to 8 weeks after the study in such a manner that the risk of pregnancy is minimized WOCBP includes any female who has experienced menarche and who has not undergone successful surgical sterilization (hysterectomy, bilateral tubal ligation, or bilateral oophorectomy) or is not postmenopausal (defined as amenorrhea for 12 consecutive months; or women on hormone replacement therapy [HRT] with documented serum follicle stimulating hormone [FSH] level>35 mIU/mL). Even women who are using oral, implanted, or injectable contraceptive hormones or mechanical products such as an intrauterine device or barrier methods (diaphragm, condoms, spermicides) to prevent pregnancy or practicing abstinence or where the partner is sterile (e.g., vasectomy), should be considered to be of childbearing potential. WOCBP must have a negative serum pregnancy test (minimum sensitivity 25 IU/L or equivalent units of human chorionic gonadotropin [HCG]) within 72 hours prior to the start of study medication.

Exclusion Criteria

1) WOCBP who are unwilling or unable to use an acceptable method to avoid pregnancy for the entire study period and for up to 8 weeks after the last infusion. 2) Women who are pregnant or breastfeeding. 3) Women with a positive pregnancy test on enrollment or prior to study drug administration. 4) Genetically-identical donor recipient pairs (ie, identical twins). 5) Donor age<10 years. 6) Subjects receiving and extended criteria donor organ as defined by: a) Donor age≧60 years OR b) Donor age 50-59 years and 1 of the following: (i) Cerebrovascular accident (CVA)+hypertension+SCr>1.5 mg/dL OR (ii) CVA+hypertension OR (iii) CVA+SCr>1.5 mg/dL OR (iv) Hypertension+SCr>1.5 mg/dL OR c) Anticipated CIT>24 hours OR d) Donor with cardiac death (non-heart beating donor). 7) Subjects with underlying renal disease of: a) Primary focal segmental glomerulosclerosis b) Type I or II membranoproliferative glomerulonephritis c) Hemolytic uremic syndrome (HUS)/thrombotic thrombocytopenic purpura syndrome If a subject has ESRD of unknown etiology and/or has no histologically-confirmed diagnosis, the subject may be enrolled into the study as long as there are no clinical signs or symptoms consistent with the clinical diagnosis of primary focal segmental glomerulosclerosis, Type I or II membranoproliferative glomerulonephritis, or HUS, as deemed by the investigator. 8) Subjects undergoing primary (first-time) transplant with a current PRA ≧50%, or subjects undergoing retransplantation with a PRA ∈30%. 9) Subjects with previous graft loss due to acute rejection. 10) Subjects with a positive T-cell lymphocytotoxic cross match. 11) Subjects with prior non-renal solid organ transplant (subjects undergoing kidney retransplantation are eligible pending other study criteria being met), or subjects undergoing multi-organ transplants (e.g., kidney-pancreas) or subjects deemed likely to have a second solid organ or cell transplant (e.g., pancreas or islet transplant) in the next 3 years by the investigator. 12) Subjects receiving a concurrent solid organ (heart, liver, pancreas) or cell (islet, bone marrow, stem cell) transplant. 13) Subjects receiving paired kidneys (dual or en bloc kidney transplants).

14) Subjects who are known hepatitis C antibody-positive or polymerase chain reaction (PCR)-positive for hepatitis C. 15) Subjects who are known hepatitis B surface antigen-positive or PCR-positive for hepatitis B. 16) Subjects with known human immunodeficiency virus (HIV) infection. 17) Subjects with active tuberculosis (TB) requiring treatment within the previous 3 years or any subject who previously required triple (or more) combination therapy for TB. Subjects with a known positive purified protein derivative (PPD) will not be eligible for the study unless they completed treatment for latent TB and have a negative chest x-ray at the time of enrollment. PPD testing done within the last 12 months is acceptable as long as there is documentation of the results. Subjects without a PPD in the last 12 months who have a previous negative result may be enrolled if they also have a negative chest x-ray at enrollment, no symptoms indicative of TB, no known TB contacts, is not currently residing in, recently traveled to, or previously immigrated from an area endemic for TB. A PPD response that is $\leq$10 mm induration or a Heaf score of >1 in non-Bacille Calmette-Guerin (non-BCG) immunized subjects or >2 in BCG immunized subjects should be considered a positive test. More conservative criteria may be applied according to the published guidelines and/or local standards endorsed by the medical society. 18) Subjects with any active infection or other contraindication that would normally exclude transplantation. 19) Subjects whose life expectancy is severely limited by disease state or other underlying medical condition. 20) Subjects with a history of cancer (other than non-melanoma skin cell cancers cured by local resection) within the last 5 years. 21) Subjects with a history of substance abuse (drug or alcohol) within the past 5 years, or psychotic disorders that are not compatible with adequate study followup. 22) Subjects with active peptic ulcer disease, chronic diarrhea, or gastrointestinal malabsorption.

Administration of and visit windows for L104EA29YIg MI and LI and CsA regimens, including list as required, will be as described above and in Example 4.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

What is claimed is:

1. A method for treating an immune disorder associated with graft transplantation comprising administering to a subject an effective dose of a CTLA4 mutant molecule comprising an extracellular domain of CTLA4 as shown in SEQ ID NO:8 beginning with alanine at position 26 or methionine at position 27 and ending with aspartic acid at position 150, or a portion thereof, wherein in the extracellular domain or portion thereof an alanine at position 55 is substituted with a tyrosine, and a leucine at position 130 is substituted with a glutamic acid and wherein the administration regimen comprises an early phase regimen, wherein the early phase regimen ranges from the first 3 to 6 months post-transplantation and involves administration on day 1, week 2 visit, week 4 visit, week 8 visit and week 12 visit, and wherein the administration regimen further comprises a maintenance phase regimen wherein the maintenance phase regimen begins after the early phase regimen ends and involves administration of CTLA4 mutant molecule that is not more frequent than monthly.

2. A method for treating an immune disorder associated with graft transplantation comprising administering to a subject an effective dose of a CTLA4 mutant molecule comprising:
  (a) an amino acid sequence beginning with methionine at position 27 and ending with aspartic acid at position 150 of SEQ ID NO:4, or
  (b) an amino acid sequence beginning with alanine at position 26 and ending with aspartic acid at position 150 of SEQ ID NO:4 and wherein the CTLA4 mutant molecule administration regimen comprises an early phase regimen, wherein the early phase regimen ranges from the first 3 to 6 months post-transplantation and involves administration on day 1, week 2 visit, week 4 visit, week 8 visit and week 12 visit, and wherein the administration regimen further comprises a maintenance phase regimen wherein the maintenance phase regimen begins after the early phase regimen ends and involves administration of CTLA4 mutant molecule that is not more frequent than monthly.

3. The method according to claim 1 or 2 wherein the early phase administration regimen comprises administration of CTLA4 mutant molecule on day 5.

4. The method according to claim 3 wherein the early phase administration regimen comprises administration of CTLA4 mutant molecule on week 6 visit, week 10 visit, month 4 visit, month 5 visit and month 6 visit.

5. The method according to claim 3 or 4 wherein the effective dose of CTLA4 mutant molecule during the early phase is about 10 mg/kg weight of the subject.

6. The method according to claim 1 or 2 wherein the effective dose of CTLA4 mutant molecule during the maintenance phase is about 5 mg/kg weight.

7. The method according to claim 1 or 2 wherein the effective dose of the CTLA4 mutant molecule is about 10 mg/kg weight of the subject with an administration regimen comprising administration on days 1, 15, 29, 57, 85 and 5 gm/kg monthly thereafter.

8. The method according to claim 1 or 2 wherein the effective dose of the CTLA4 mutant molecule is about 10 mg/kg weight of the subject with an administration regimen comprising administration on days 1, 5, 15, 29, 57, 85 and 5 mg/kg monthly thereafter.

9. The method according to claim 1 or 2 wherein the effective dose of the CTLA4 mutant molecule is about 10 mg/kg weight of the subject with an administration regimen
  comprising administration on days 1, 5, 15, 29, 43, 57, 71, 85, 113, 141, 169 and 5 mg/kg monthly thereafter.

10. The method according to claim 1 or 2 wherein the immune disorders associated wit graft transplantation comprises solid organ, tissue and/or cell transplant rejection.

11. The method according to claim 10 wherein the immune disorders associated with graft transplantation comprises kidney transplant rejection.

12. The method according to claim 1 or 2 wherein the CTLA4 mutant molecules further comprise an amino acid sequence which alters the solubility, affinity and/or valency of the soluble CTLA4 mutant molecule.

13. The method according to claim 12, wherein the amino acid sequence which alters the solubility, affinity and/or valency comprises an immunoglobulin moiety.

14. The method according to claim 13, wherein the immunoglobulin moiety is an immunoglobulin constant region or portion thereof 15. The method according to claim 14, wherein the immunoglobulin constant region or portion thereof is mutated to reduce effector function.

16. The method according to claim 14 wherein the immunoglobulin constant region or portion thereof comprises a hinge, CH2 and CH3 regions of a human or monkey immunoglobulin molecule.

17. The method according to claim 15 wherein the immunoglobulin constant region or portion thereof comprises a hinge, CH2 and CH3 regions of a human or monkey immunoglobulin molecule.

18. The method according to claim 13, wherein the immunoglobulin comprises an amino acid sequence which begins with glutamic acid at position +152 and ends with lysine at position +383, as shown in SEQ ID NO:4.

19. The method according to claims 1 or 2 further comprising a junction amino acid residue and an immunoglobulin, where the junction amino acid residue is located between the amino acid sequence which ends with aspartic acid at position +150 and the immunoglobulin.

20. The method according to claim 1 or 2 wherein said CTLA4 mutant molecule is co-administered with at least one of the agents selected from the group consisting of basiliximab, daclizumab, anti-thymocyte globulin, cyclosporine, tacrolimus, mycophenolate mofetil (MMF), mycophenolic acid, azathioprine, muromonab, rituximab, sirolimus, everolimus, fingolimod, Jak-3, betamethasone, budesonide, cortisol, cortisone, dexamethasone, hydrocritisone, methyiprednisolone, prednisolone, prednisone and triameinolone.

21. A method according to claim 1 or 2 wherein development and/or progression of an outcome selected from the group consisting of chronic allograft neuropathy (CAN), hyperlipidemia, hypertension, diabetes, hirsuitism, alopecia, gingival hyperplasia, tremor, neurotoxicity and bone loss is reduced.

22. The method according to claim 1 or 2 further comprising a target trough serum concentration of the CTLA4 mutant molecule between about 3 μg/ml and about 30 μg/ml.

23. A method for treating an immune disorder associated with graft transplantation comprising administering to a subject an effective dose of a CTLA4 mutant molecule comprising:
   (a) an amino acid sequence beginning with methionine at position 27 and ending with lysine at position +357 or glycine at position +356 of FIG. 7, or
   (b) an amino acid sequence beginning with alanine at position 26 and ending with lysine at position +357 or glycine at position +356 of FIG. 7 and
wherein the CTLA4 mutant molecule administration regimen comprises an early phase regimen, wherein the early phase regimen ranges from the first 3 to 6 months post-transplantation and involves administration on day 1, week 2 visit, week 4 visit, week 8 visit and week 12 visit,, and wherein the administration regimen further comprises a maintenance phase regimen wherein the maintenance phase regimen begins after the early phase regimen ends and involves administration of CTLA4 mutant molecule that is not more frequent than monthly.

24. The method according to claim 1, 2 or 23 wherein the CTLA4 mutant molecule is co-administered concomitantly or sequentially with agents comprising basiliximab and MMF.

25. The method according to claim 1, 2 or 23 wherein the CTLA4 mutant molecule is co-administered concomitantly or sequentially with agents comprising daclizumab and sirolimus.

* * * * *

UNITED STATES PATENT AND TRADEMARK OFFICE
CERTIFICATE OF CORRECTION

PATENT NO. : 7,482,327 B2
APPLICATION NO. : 11/399666
DATED : January 27, 2009
INVENTOR(S) : David Hagerty and James Rusnak It is certified that error appears in the above-identified patent and that said Letters Patent is hereby corrected as shown below:

Column 2
Line 10 subcutaneous should be "subcutanous"

Column 3
Line 8 rom should be "from"

Column 12
Line 32 immunoglobuling should be "immunoglobulin"

Column 22
Line 29 azathioprene should be "azathioprine"

Column 32
Line 25 subdloned should be "subcloned"

In the Claims:
Column 74: lines 25-27;
Claim 5 should read "The method according to claim 1 or 2 wherein the effective dose of CTLA4 mutant molecule during the early phase is about 10 mg/kg weight of the subject."

UNITED STATES PATENT AND TRADEMARK OFFICE
CERTIFICATE OF CORRECTION

PATENT NO. : 7,482,327 B2
APPLICATION NO. : 11/399666
DATED : January 27, 2009
INVENTOR(S) : David Hagerty and James Rusnak It is certified that error appears in the above-identified patent and that said Letters Patent is hereby corrected as shown below:

Column 75
Claim 20
Line 25 methyiprednisolone should be "methylprednisolone"
Line 26 triameinolone should be "triamcinolone"
Line 30 hirsuitism should be "hirsutism"

Signed and Sealed this

Fifth Day of May, 2009

JOHN DOLL
*Acting Director of the United States Patent and Trademark Office*

```
                            SEQUENCE LISTING

<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: Oncostatin M CTLA4 (OMCTLA4) Forward Primer

<400> SEQUENCE: 1
gaggtgataa agcttcacca atgggtgtac tgctcacaca g                    41

<210> SEQ ID NO 2
<211> LENGTH: 42
<212> TYPE: DNA
<213> ORGANISM: Artificial Sequence
<220> FEATURE:
<223> OTHER INFORMATION: Oncostatin M CTLA4 (OMCTLA4) Reverse Primer

<400> SEQUENCE: 2
gtggtgtatt ggtctagatc aatcagaatc tgggcacggt tc                   42

<210> SEQ ID NO 3
<211> LENGTH: 1152
<212> TYPE: DNA
<213> ORGANISM: Artificial Sequence
<220> FEATURE:
<223> OTHER INFORMATION: L104EA29YIg

<400> SEQUENCE: 3
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aatatactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
```

-continued

```
gtgaacctca ctatccaagg actgagggcc atggacacgg gactctacat ctgcaaggtg      360
gagctcatgt acccaccgcc atactacgag ggcataggca acggaaccca gatttatgta      420
attgatccag aaccgtgccc agattctgat caggagccca atcttctga caaaactcac       480 acatccccac cgtccccagc acctgaactc ctggggggat cgtcagtctt cctcttcccc      540
ccaaaaccca aggacaccct catgatctcc cggacccctg aggtcacatg cgtggtggtg      600
gacgtgagcc acgaagaccc tgaggtcaag ttcaactggt acgtggacgg cgtggaggtg      660
cataatgcca agacaaagcc gcgggaggag cagtacaaca gcacgtaccg tgtggtcagc      720
gtcctcaccg tcctgcacca ggactggctg aatggcaagg agtacaagtg caaggtctcc      780
aacaaagccc tcccagcccc catcgagaaa accatctcca aagccaaagg cagccccga      840 gaaccacagg tgtacaccct gcccccatcc cgggatgagc tgaccaagaa ccaggtcagc      900
ctgacctgcc tggtcaaagg cttctatccc agcgacatcg ccgtggagtg ggagagcaat      960
gggcagccgg agaacaacta caagaccacg cctcccgtgc tggactccga cggctccttc     1020
ttcctctaca gcaagctcac cgtggacaag agcaggtggc agcaggggaa cgtcttctca     1080
tgctccgtga tgcatgaggc tctgcacaac cactacacgc agaagagcct ctccctgtct     1140
ccgggtaaat ga                                                         1152
```

<210> SEQ ID NO 4
<211> LENGTH: 383
<212> TYPE: PRT
<213> ORGANISM: Artificial Sequence
<220> FEATURE:
<223> OTHER INFORMATION: L104EA29YIg

<400> SEQUENCE: 4

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205
```

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
            275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
    370                 375                 380

<210> SEQ ID NO 5
<211> LENGTH: 1152
<212> TYPE: DNA
<213> ORGANISM: Artificial Sequence
<220> FEATURE:
<223> OTHER INFORMATION: L104EIg

<400> SEQUENCE: 5

| | | |
|---|---|---|
| atgggtgtac tgctcacaca gaggacgctg ctcagtctgg tccttgcact cctgtttcca | 60 |
| agcatggcga gcatggcaat gcacgtggcc cagcctgctg tggtactggc cagcagccga | 120 |
| ggcatcgcta gctttgtgtg tgagtatgca tctccaggca agccactgaa ggtccgggtg | 180 |
| acagtgcttc ggcaggctga cagccaggtg actgaagtct gtgcggcaac ctacatgatg | 240 |
| gggaatgagt tgaccttcct agatgattcc atctgcacgg gcacctccag tggaaatcaa | 300 |
| gtgaacctca ctatccaagg actgagggcc atggacacgg actctacatc tgcaaggtg | 360 |
| gagctcatgt acccaccgcc atactacgag ggcataggca cggaacccca gatttatgta | 420 |
| attgatccag aaccgtgccc agattctgat caggagccca atcttctga caaaactcac | 480 |
| acatccccac cgtccccagc acctgaactc ctggggggat cgtcagtctt cctcttcccc | 540 |
| ccaaaaccca aggacaccct catgatctcc cggacccctg aggtcacatg cgtggtggtg | 600 |
| gacgtgagcc acgaagaccc tgaggtcaag ttcaactggt acgtggacgg cgtggaggtg | 660 |
| cataatgcca agacaaagcc gcgggaggag cagtacaaca gcacgtaccg tgtggtcagc | 720 |
| gtcctcaccg tcctgcacca ggactggctg aatggcaagg agtacaagtg caaggtctcc | 780 |
| aacaaagccc tcccagcccc catcgagaaa accatctcca aagccaaagg gcagccccga | 840 |
| gaaccacagg tgtacaccct gcccccatcc cgggatgagc tgaccaagaa ccaggtcagc | 900 |
| ctgacctgcc tggtcaaagg cttctatccc agcgacatcg ccgtggagtg ggagagcaat | 960 |
| gggcagccgg agaacaacta caagaccacg cctcccgtgc tggactccga cggctccttc | 1020 |
| ttcctctaca gcaagctcac cgtggacaag agcaggtggc agcaggggaa cgtcttctca | 1080 | tgctccgtga tgcatgaggc tctgcacaac cactacacgc agaagagcct ctccctgtct    1140 ccgggtaaat ga                                                         1152

<210> SEQ ID NO 6
<211> LENGTH: 383
<212> TYPE: PRT
<213> ORGANISM: Artificial Sequence
<220> FEATURE:
<223> OTHER INFORMATION: L104EIg

<400> SEQUENCE: 6

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350
```

```
Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
            370                 375                 380

<210> SEQ ID NO 7
<211> LENGTH: 1152
<212> TYPE: DNA
<213> ORGANISM: Artificial Sequence
<220> FEATURE:
<223> OTHER INFORMATION: CTLA4Ig

<400> SEQUENCE: 7
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacctg ggcataggca acggaaccca gatttatgta     420
attgatccag aaccgtgccc agattctgat caggagccca atcttctga caaaactcac      480
acatccccac cgtccccagc acctgaactc ctggggtgga cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg ggtggtcagc     720
gtcctcaccg tcctgcacca ggactggctg aatggcaagg agtacaagtg caaggtctcc     780
aacaaagccc tcccagcccc catcgagaaa accatctcca agccaaagg gcagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152

<210> SEQ ID NO 8
<211> LENGTH: 383
<212> TYPE: PRT
<213> ORGANISM: Artificial Sequence
<220> FEATURE:
<223> OTHER INFORMATION: CTLA4Ig

<400> SEQUENCE: 8

Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Ala Thr Glu Val Arg Val Thr Val Leu Arg
        50                  55                  60
```

```
Gln Ala Asp Ser Gln Val Thr Glu Val Cys Ala Ala Thr Tyr Met Met
 65              70                  75                  80
Gly Asn Glu Leu Thr Phe Leu Asp Asp Ser Ile Cys Thr Gly Thr Ser
                 85                  90                  95
Ser Gly Asn Gln Val Asn Leu Thr Ile Gln Gly Leu Arg Ala Met Asp
            100                 105                 110
Thr Gly Leu Tyr Ile Cys Lys Val Glu Leu Met Tyr Pro Pro Pro Tyr
        115                 120                 125
Tyr Leu Gly Ile Gly Asn Gly Thr Gln Ile Tyr Val Ile Asp Pro Glu
    130                 135                 140
Pro Cys Pro Asp Ser Asp Gln Glu Pro Lys Ser Ser Asp Lys Thr His
145                 150                 155                 160
Thr Ser Pro Pro Ser Pro Ala Pro Glu Leu Leu Gly Gly Ser Ser Val
                165                 170                 175
Phe Leu Phe Pro Pro Lys Pro Lys Asp Thr Leu Met Ile Ser Arg Thr
            180                 185                 190
Pro Glu Val Thr Cys Val Val Val Asp Val Ser His Glu Asp Pro Glu
        195                 200                 205
Val Lys Phe Asn Trp Tyr Val Asp Gly Val Glu Val His Asn Ala Lys
    210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
    290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys
    370                 375                 380

<210> SEQ ID NO 9
<211> LENGTH: 636
<212> TYPE: DNA
<213> ORGANISM: Homo Sapiens
<220> FEATURE:
<221> NAME/KEY: CDS
<222> LOCATION: (1)..(636)
<220> FEATURE:
<221> NAME/KEY: mat_peptide
<222> LOCATION: (79)..()

<400> SEQUENCE: 9 atg ggt gta ctg ctc aca cag agg acg ctg ctc agt ctg gtc ctt gca      48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct      96
```

```
Leu Leu Phe Pro Ser Met Ala Ser Met Ala Met His Val Ala Gln Pro
-10              -5               -1   1                 5 gct gtg gta ctg gcc agc agc cga ggc atc gcc agc ttt gtg tgt gag    144
Ala Val Val Leu Ala Ser Ser Arg Gly Ile Ala Ser Phe Val Cys Glu
             10              15              20 tat gca tct cca ggc aaa gcc act gag gtc cgg gtg aca gtg ctt cgg    192
Tyr Ala Ser Pro Gly Lys Ala Thr Glu Val Arg Val Thr Val Leu Arg
         25              30              35 cag gct gac agc cag gtg act gaa gtc tgt gcg gca acc tac atg atg    240
Gln Ala Asp Ser Gln Val Thr Glu Val Cys Ala Ala Thr Tyr Met Met
     40              45              50 ggg aat gag ttg acc ttc cta gat gat tcc atc tgc acg ggc acc tcc    288
Gly Asn Glu Leu Thr Phe Leu Asp Asp Ser Ile Cys Thr Gly Thr Ser
55              60              65              70 agt gga aat caa gtg aac ctc act atc caa gga ctg agg gcc atg gac    336
Ser Gly Asn Gln Val Asn Leu Thr Ile Gln Gly Leu Arg Ala Met Asp
             75              80              85 acg gga ctc tac atc tgc aag gtg gag ctc atg tac cca ccg cca tac    384
Thr Gly Leu Tyr Ile Cys Lys Val Glu Leu Met Tyr Pro Pro Pro Tyr
         90              95             100 tac ctg ggc ata ggc aac gga acc cag att tat gta att gat cca gaa    432
Tyr Leu Gly Ile Gly Asn Gly Thr Gln Ile Tyr Val Ile Asp Pro Glu
    105             110             115 ccg tgc cca gat tct gac ttc ctc ctc tgg atc ctt gca gca gtt agt    480
Pro Cys Pro Asp Ser Asp Phe Leu Leu Trp Ile Leu Ala Ala Val Ser
120             125             130 tcg ggg ttg ttt ttt tat agc ttt ctc ctc aca gct gtt tct ttg agc    528
Ser Gly Leu Phe Phe Tyr Ser Phe Leu Leu Thr Ala Val Ser Leu Ser
135             140             145             150 aaa atg cta aag aaa aga agc cct ctt aca aca ggg gtc tat gtg aaa    576
Lys Met Leu Lys Lys Arg Ser Pro Leu Thr Thr Gly Val Tyr Val Lys
                155             160             165 atg ccc cca aca gag cca gaa tgt gaa aag caa ttt cag cct tat ttt    624
Met Pro Pro Thr Glu Pro Glu Cys Glu Lys Gln Phe Gln Pro Tyr Phe
            170             175             180 att ccc atc aat                                                    636
Ile Pro Ile Asn
        185

<210> SEQ ID NO 10
<211> LENGTH: 212
<212> TYPE: PRT
<213> ORGANISM: Homo Sapiens

<400> SEQUENCE: 10

Met Gly Val Leu Leu Thr Gln Arg Thr Leu Leu Ser Leu Val Leu Ala
    -25             -20             -15

Leu Leu Phe Pro Ser Met Ala Ser Met Ala Met His Val Ala Gln Pro
-10              -5               -1   1                 5

Ala Val Val Leu Ala Ser Ser Arg Gly Ile Ala Ser Phe Val Cys Glu
             10              15              20

Tyr Ala Ser Pro Gly Lys Ala Thr Glu Val Arg Val Thr Val Leu Arg
         25              30              35

Gln Ala Asp Ser Gln Val Thr Glu Val Cys Ala Ala Thr Tyr Met Met
     40              45              50

Gly Asn Glu Leu Thr Phe Leu Asp Asp Ser Ile Cys Thr Gly Thr Ser
55              60              65              70

Ser Gly Asn Gln Val Asn Leu Thr Ile Gln Gly Leu Arg Ala Met Asp
             75              80              85
```

-continued

```
Thr Gly Leu Tyr Ile Cys Lys Val Glu Leu Met Tyr Pro Pro Pro Tyr
            90              95                  100

Tyr Leu Gly Ile Gly Asn Gly Thr Gln Ile Tyr Val Ile Asp Pro Glu
        105              110                  115

Pro Cys Pro Asp Ser Asp Phe Leu Leu Trp Ile Leu Ala Ala Val Ser
    120              125              130

Ser Gly Leu Phe Phe Tyr Ser Phe Leu Leu Thr Ala Val Ser Leu Ser
135              140              145              150

Lys Met Leu Lys Lys Arg Ser Pro Leu Thr Thr Gly Val Tyr Val Lys
            155              160              165

Met Pro Pro Thr Glu Pro Glu Cys Glu Lys Gln Phe Gln Pro Tyr Phe
            170              175              180

Ile Pro Ile Asn
        185
```